(12) United States Patent
Jarrett et al.

(10) Patent No.: US 11,938,223 B2
(45) Date of Patent: Mar. 26, 2024

(54) SHAPE CHANGING DRUG DELIVERY DEVICES AND METHODS

(71) Applicant: Incept, LLC, Lexington, MA (US)

(72) Inventors: Peter Jarrett, Lexington, MA (US); Michael J. McGrath, Upton, MA (US); Timothy S. Jarrett, Boston, MA (US); Rami El-Hayek, Norwood, MA (US); Andrew C. Vanslette, Medford, MA (US); Courtney A Rosales, Ipswich, MA (US); Charles D. Blizzard, Nashua, NH (US); Amarpreet S. Sawhney, Lexington, MA (US)

(73) Assignee: Incept, LLC, Lexington, MA (US)

(*) Notice: Subject to any disclaimer, the term of this patent is extended or adjusted under 35 U.S.C. 154(b) by 96 days.

(21) Appl. No.: 17/859,820

(22) Filed: Jul. 7, 2022

(65) Prior Publication Data
US 2022/0339108 A1    Oct. 27, 2022

Related U.S. Application Data

(63) Continuation of application No. 16/999,504, filed on Aug. 21, 2020, now Pat. No. 11,413,250, which is a continuation of application No. 16/533,331, filed on Aug. 6, 2019, now Pat. No. 10,786,462, which is a
(Continued)

(51) Int. Cl.
| | |
|---|---|
| *A61K 47/10* | (2017.01) |
| *A61K 9/00* | (2006.01) |
| *A61K 9/20* | (2006.01) |
| *A61K 31/4439* | (2006.01) |
| *A61P 27/02* | (2006.01) |

(52) U.S. Cl.
CPC .......... *A61K 9/2072* (2013.01); *A61K 9/0051* (2013.01); *A61K 9/2031* (2013.01); *A61K 31/4439* (2013.01); *A61K 47/10* (2013.01)

(58) Field of Classification Search
None
See application file for complete search history.

(56) References Cited

U.S. PATENT DOCUMENTS

| | | |
|---|---|---|
| 3,640,741 A | 2/1972 | Etes |
| 3,865,108 A | 2/1975 | Hartop |
| 3,992,562 A | 11/1976 | Denzinger et al. |

(Continued)

FOREIGN PATENT DOCUMENTS

| | | |
|---|---|---|
| CN | 102395401 | 3/2012 |
| JP | H07216101 | 8/1995 |

(Continued)

OTHER PUBLICATIONS

Fusco et al., "Self-Folding Mobile Microrobots For Biomedical Applications", International Conference on Robotics & Automation (ICRA) Hong Kong Convention and Exhibition Center, 6 Pages, p. 3777-3782 (May 31-Jun. 7, 2014).

(Continued)

*Primary Examiner* — Ernst V Arnold
(74) *Attorney, Agent, or Firm* — Christensen, Fonder, Dardi; Diane E. Bennett; Peter S. Dardi

(57) ABSTRACT

Drug delivery using bio-affecting drugs, particularly with shape changing drug delivery devices. Embodiments are included for depots for delivery of a therapeutic agent that change from an elongated state ex vivo to a coil in vivo where the agent is released.

20 Claims, 22 Drawing Sheets

Related U.S. Application Data continuation of application No. 15/360,430, filed on Nov. 23, 2016, now Pat. No. 10,420,724.

(60) Provisional application No. 62/260,068, filed on Nov. 25, 2015, provisional application No. 62/319,033, filed on Apr. 6, 2016.

(56) References Cited

U.S. PATENT DOCUMENTS

| | | | |
|---|---|---|---|
| 4,002,173 | A | 1/1977 | Manning et al. |
| 4,014,335 | A | 3/1977 | Arnold |
| 4,207,893 | A | 6/1980 | Michaels |
| 4,484,922 | A | 11/1984 | Rosenwald |
| 4,741,872 | A | 5/1988 | De Luca et al. |
| 4,826,945 | A | 5/1989 | Cohn et al. |
| 4,938,763 | A | 7/1990 | Dunn et al. |
| 5,100,992 | A | 3/1992 | Cohn et al. |
| 5,160,745 | A | 11/1992 | De Luca et al. |
| 5,304,595 | A | 4/1994 | Rhee et al. |
| 5,324,775 | A | 6/1994 | Rhee et al. |
| 5,410,016 | A | 4/1995 | Hubbell et al. |
| 6,149,931 | A | 11/2000 | Schwartz et al. |
| 6,371,975 | B2 | 4/2002 | Cruise et al. |
| 6,379,373 | B1 | 4/2002 | Sawhney et al. |
| 6,514,534 | B1 | 2/2003 | Sawhney |
| 6,566,406 | B1 | 5/2003 | Pathak et al. |
| 6,632,457 | B1 | 10/2003 | Sawhney |
| 6,958,212 | B1 | 10/2005 | Hubbell et al. |
| 7,129,210 | B2 | 10/2006 | Lowinger et al. |
| 7,648,713 | B2 | 1/2010 | Sawhney |
| 8,409,606 | B2 | 4/2013 | Sawhney et al. |
| 8,715,712 | B2 | 5/2014 | de Juan et al. |
| 8,795,709 | B2 | 8/2014 | Sawhney et al. |
| 8,961,501 | B2 | 2/2015 | Jarrett et al. |
| 9,125,807 | B2 | 9/2015 | Sawhney et al. |
| 9,205,150 | B2 | 12/2015 | Jarrett et al. |
| 10,420,724 | B2 | 9/2019 | Jarrett et al. |
| 2002/0026176 | A1 | 2/2002 | Varner et al. |
| 2004/0086479 | A1 | 5/2004 | Grinstaff et al. |
| 2004/0131582 | A1 | 7/2004 | Grinstaff et al. |
| 2008/0220047 | A1 | 9/2008 | Sawhney et al. |
| 2008/0287633 | A1 | 11/2008 | Drumheller |
| 2009/0017097 | A1 | 1/2009 | Sawhney et al. |
| 2009/0252781 | A1 | 10/2009 | Sawhney et al. |
| 2010/0209478 | A1 | 8/2010 | Sawhney et al. |
| 2011/0142936 | A1 | 6/2011 | Campbell et al. |
| 2012/0071865 | A1 | 3/2012 | Jarrett et al. |
| 2013/0071462 | A1 | 3/2013 | Jarrett et al. |
| 2013/0156725 | A1 | 6/2013 | Marom et al. |
| 2014/0121612 | A1 | 5/2014 | Rubin et al. |
| 2014/0179802 | A1 | 6/2014 | Franken et al. |
| 2016/0166504 | A1 | 6/2016 | Jarrett et al. |
| 2016/0331738 | A1 | 11/2016 | Jarrett et al. |
| 2017/0020729 | A1 | 1/2017 | Jarrett et al. |

FOREIGN PATENT DOCUMENTS

| | | |
|---|---|---|
| WO | 2006031358 | 3/2006 |
| WO | 2006031388 | 3/2006 |
| WO | 2007001926 | 1/2007 |
| WO | 2007005249 | 4/2009 |

OTHER PUBLICATIONS

Yoshida et al., "Functionalized Core-Shell Hydrogel Microsprings by Anisotropic Gelation With Bevel-Tip Capillary", Scientific Reports, 9 Pages (Apr. 5, 2017).

Zhao et al., "Reactive Macromolecular Micelle Crosslinked Highly Elastic Hydrogel With Water-Triggered Shape-Memory Behaviour", Polymer Chemistry, vol. 5:4965-4973 (2014).

Zhang et al., "Synthesis of Poly(ethylene glycol)-Based Hydrogels via Amine-Michael Type Addition With Tunable Stiffness and Postgelation Chemical Functionality", Chemistry of Materials, vol. 26:3624-3630 (2014).

International Search Report and Written Opinion from corresponding PCT Application No. PCT/US2016/063633, 13 pages, dated Feb. 24, 2017.

t=0 SECONDS t=3 SECONDS t=8 SECONDS t=0 SECONDS t=6 SECONDS t=10 SECONDS

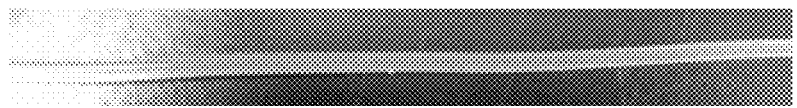
FIG. 15A
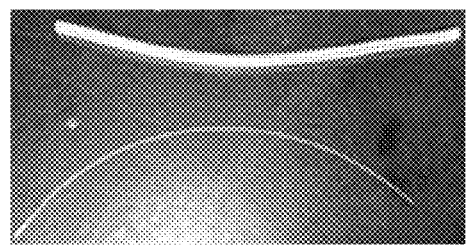
FIG. 15B
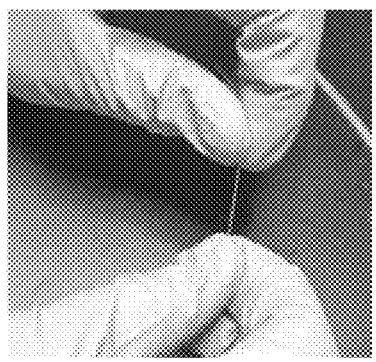 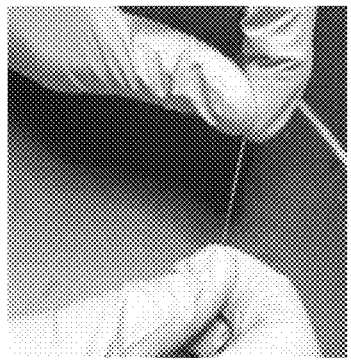 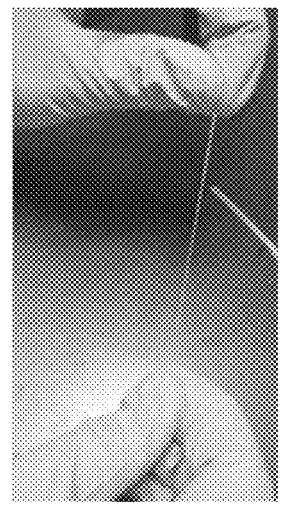
FIG. 15C  FIG. 15D  FIG. 15E
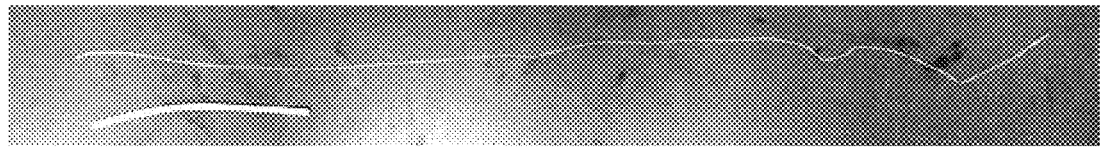
FIG. 15F Dry: 25mm x 0.2mm fiber fiber in 27G TW needle

| Lot # | # of Fiber's | Avg. Diameter (mm) | Avg. Loose Coil Time(s) |
|---|---|---|---|
| TP-245-100-A | 1 | 0.32 | 20.3 |
| TP-245-100-B | 3 | 0.33 | 10.0 |
| TP-245-100-C | 5 | 0.31 | 8.3 |
| TP-245-108-A | 7 | 0.35 | 4.5 |
| TP-245-108-B | 9 | 0.34 | 4 |

| | 0 Sec | 5 Sec | 10 Sec | 15 Sec | 20 Sec |
|---|---|---|---|---|---|
| TP-245-100-A | | | | | |
| TP-245-100-B | | | | N/A | N/A |
| TP-245-100-C | | | | N/A | N/A |
| TP-245-108-A | | | N/A | N/A | N/A |
| TP-245-108-B | | | N/A | N/A | N/A |

FIG. 19

| Lot # | Segment Configuration | Deployed Image | Notes on Fiber Distance |
|---|---|---|---|
| MD-300-018 | 1 x 60 mm | 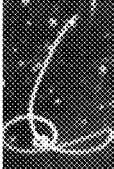 | Longer than length of fiber injection distance evaluation chamber |
| MD-300-018 | 2 x 30 mm |  | Also longer than length of fiber injection distance evaluation chamber |
| TP-245-157-(1-3) | 4 x 15 mm | 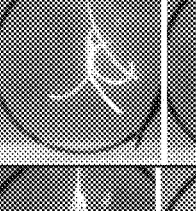 | Almost reached (80%) the hoop of wire representing the OD of a human eye |
| Tp-245-157-(6-9) | 5 x 12 mm | 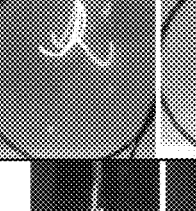 | Was not at risk (60%) of reached the bounds of the hoop of wire representing the OD of a human eye |
| TP-245-157-(12-16) | 6 x 10 mm |  | Not shown with hoop of wire but went the shortest distance from the needle |

FIG. 21

| Lot # | Segment Configuration | Fiber cut angle | Injectable (Y/N) | Deployed Image | Observation rate of fiber training |
|---|---|---|---|---|---|
| TP-245-157-(1-3) | 4 x 15 mm | 45° | Y | | Slight to Moderate |
| TP-245-157-4 | 4 x 15 mm | 30° | Y | | Moderate to Extreme |
| TP-245-157-11 | 4 x 15 mm | 60° | N | N/A | N/A |
| Tp-245-157-(6-9) | 5 x 12 mm | 45° | Y | | Slight |
| TP-245-157-(12-16) | 5 x 12 mm | 52.5° | Y | | None to Slight |

FIG. 22

NECKING A DRY FIBER BY DRAWING

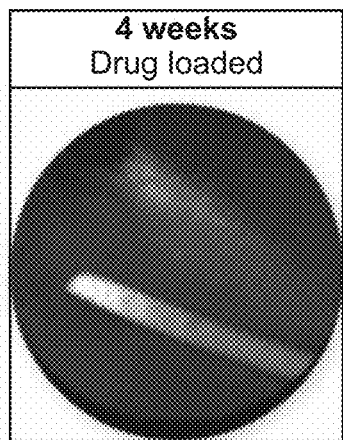
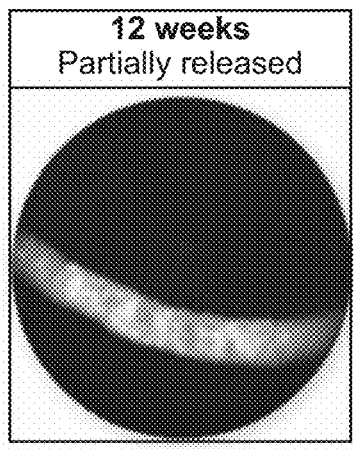
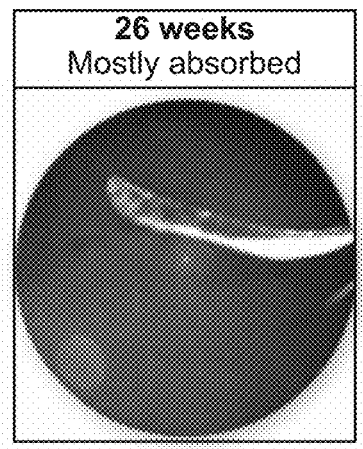
FIG. 25A  FIG. 25B  FIG. 25C
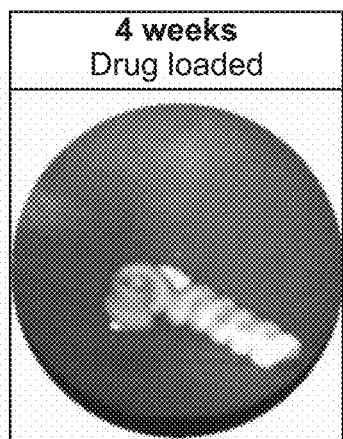
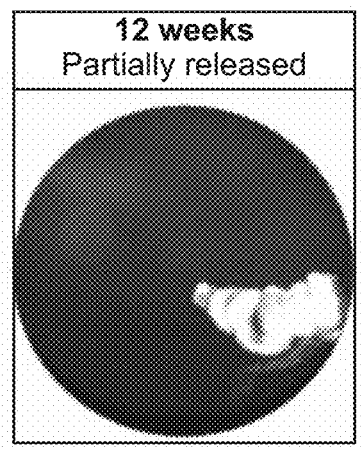
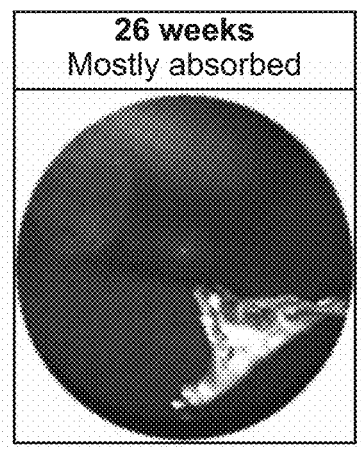
FIG. 26A  FIG. 26B  FIG. 26C

SHAPE CHANGING DRUG DELIVERY DEVICES AND METHODS

CROSS REFERENCE TO RELATED APPLICATIONS

This patent application is a continuation of U.S. patent application Ser. No. 16/999,504 to Jarrett et al., filed on Aug. 21, 2020, entitled "Shape Changing Drug Delivery Devices and Methods"; which is a continuation of U.S. patent application Ser. No. 16/533,331 to Jarrett et al. (now U.S. Pat. No. 10,786,462), filed on Aug. 6, 2019, entitled "Shape Changing Drug Delivery Devices and Methods"; which is a continuation of U.S. patent application Ser. No. 15/360,430 to Jarrett et al. (now U.S. Pat. No. 10,420,724), filed on Nov. 23, 2016, entitled "Shape Changing Drug Delivery Devices and Methods"; which claims priority to U.S. Provisional Application No. 62/260,068 to Jarrett et al., filed Nov. 25, 2015 and U.S. Provisional Application No. 62/319,033 to Jarrett et al., filed Apr. 6, 2016, which are all hereby incorporated by reference herein.

TECHNICAL FIELD

The technical field is related to drug delivery using bio-affecting drugs.

BACKGROUND

Drug delivery is the art of making and using formulations, technologies, and systems for transporting a therapeutic agent in the body as needed to safely achieve its desired therapeutic effect. Drug delivery is an active field involving many scientists and scientific disciplines. There is an ongoing need to find new and better ways to deliver therapeutic agents.

SUMMARY OF THE INVENTION

Placement and successful use of a drug delivery device in an eye is challenging because the interior of the eye is very sensitive to foreign bodies, has a limited volume, and tissue trauma from surgical implantation procedures can have important sequellae. Depots that have a slim profile to facilitate placement and a different, compact space-saving shape after placement are described herein for delivery of TKIs or other therapeutic agents, e.g., proteins, antibodies, or antibody fragments. An embodiment of the vehicle component of drug depots is a highly biocompatible material shaped as a thin rod ex vivo but transforms into a curved, coiled, or even helical, hydrogel in vivo. The hydrogel matrix and the TKI or other agent can be chosen to provide conditions suitable for controlled drug delivery, even over a time period of many months. Materials and methods of drug delivery are set forth herein that are useful in the eye and are generally useful in the body. Hydrogels that curl into complex shapes are described herein that have various advantages as vehicles for delivery of agents.

BRIEF DESCRIPTION OF DRAWINGS

FIGS. 15A-15F are photographs of a process of making a fiber depot as set forth in Example 10;

FIG. 19 provides results of an experiment set forth in Example 13, with multiple fibers coated by an outer hydrogel containing bovine IgG spray dried particles, showing a time required to form the coil shape;

FIG. 21 provides results of a first series of experiment set forth in Example 15 for multiple fibers being introduced serially in the depot, in consideration of the volume and working area of an eye;

FIG. 22 provides results of a second series of experiments set forth in Example 16 for multiple fibers being introduced serially into the depot, in consideration of the volume and working area of an eye;

FIGS. 25A-25C are photomicrographs of an in vivo drug delivery test of necked vehicles as set forth in Example 17; and FIGS. 26A-26C are photomicrographs of an in vivo drug delivery test of coiled bipolymer as set forth in Example 17.

DETAILED DESCRIPTION

Figure 1:
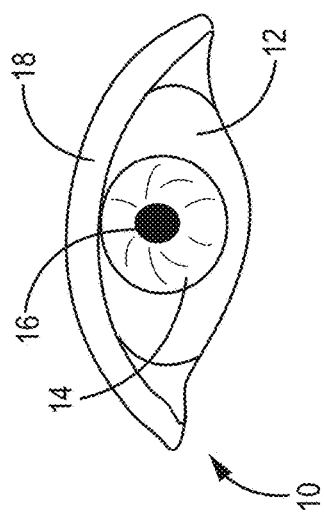
FIG. 1 is a perspective view of a human eye.
Figure 2:
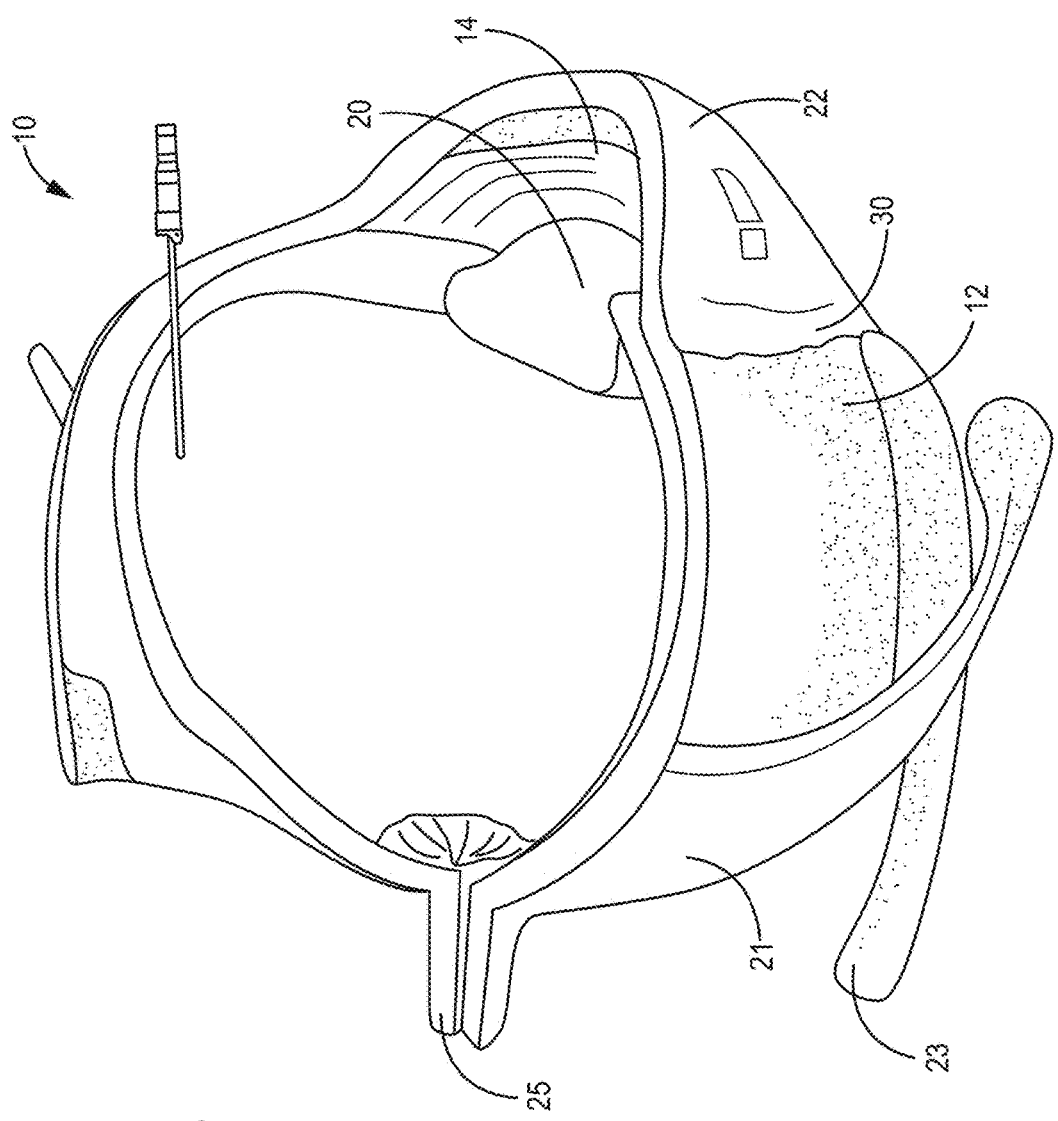
FIG. 2 is a partial cut-away perspective view of a human eye, depicting a hypodermic needle penetrating into the intraocular space for placement of a drug delivery device.
Figure 3:
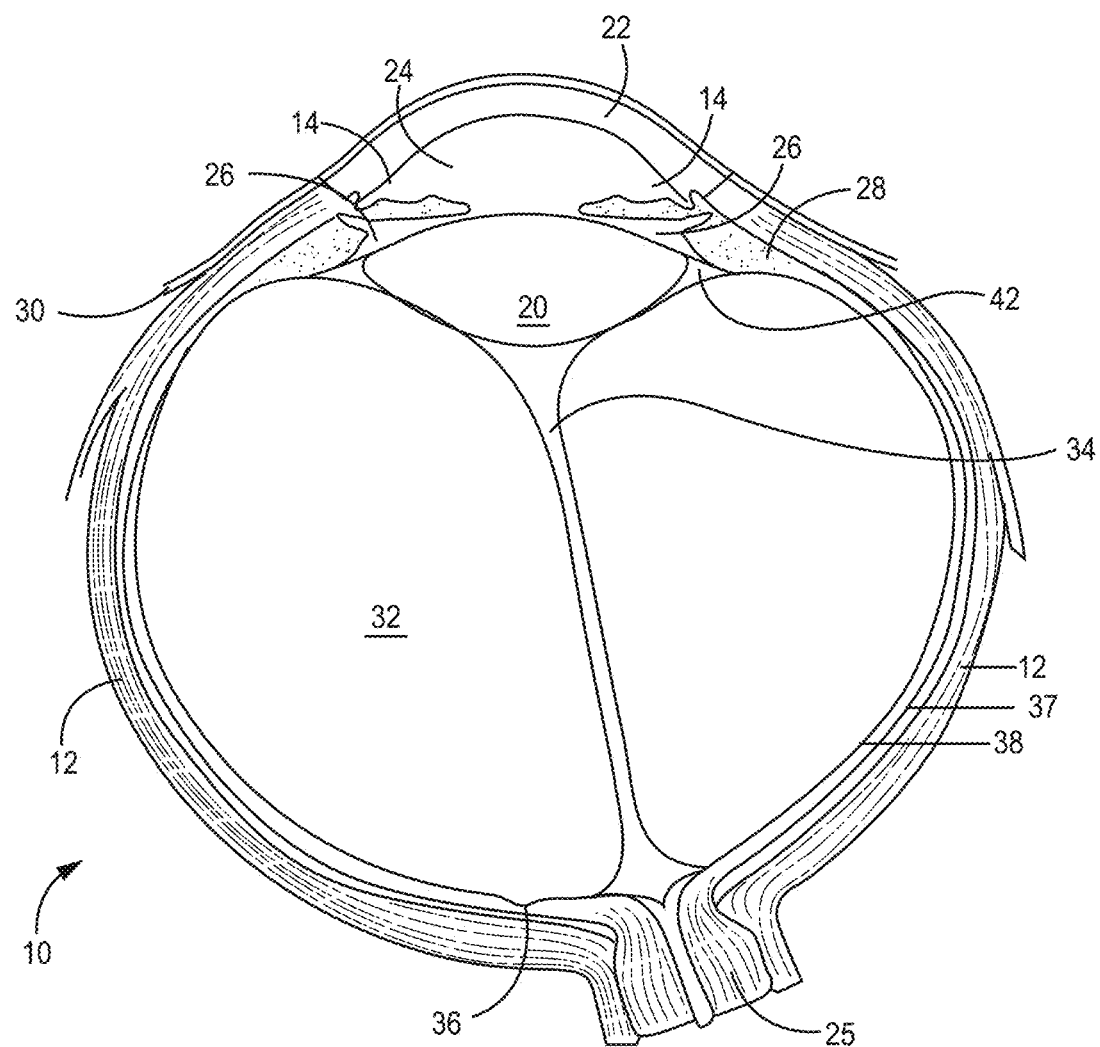
FIG. 3 is a cross-sectional view of a human eye.

Drug delivery to the eye is an active field. Improvements in drugs for treatment of eye diseases have created new options for patients, including controlled release devices. Some ocular drug delivery devices were like traditional drug delivery devices, for instance, a drug was released from a chamber through a membrane or by osmotic pumping. These have certain limitations, however, including a limited volume that can be tolerated by the eye. Another approach to ocular extended release was to put drugs into degradable particles that were injected into the eye. There were sometimes problems, however, with the particles settling onto the retina and causing contact toxicity. Innovators in this field then created small drug delivery devices that are biodegradable rods of poly(lactic-co-glycolic acid) copolymers (PLA/PGA) that are impregnated with drugs and inserted into the eye. As they erode, the drug is able to move out of the PLA/PGA matrix, so that the degradation controls the rate of release. These devices are effective to provide extended release as they are eroded by the aqueous solution in the eye. Another approach has involved the use of certain hydrogels that are formed in situ or that use various controlled release techniques, as in US 2009/0252781, US 2013/0071462, U.S. Pat. No. 8,961,501, or US 2013/0156725. However, there are further techniques that can be used to increase the range of clinical treatments that can be made with controlled release devices for the eye. FIGS. 1-3, discussed below, show the eye's anatomy. These same techniques can be extended to other tissues.

Figure 4:
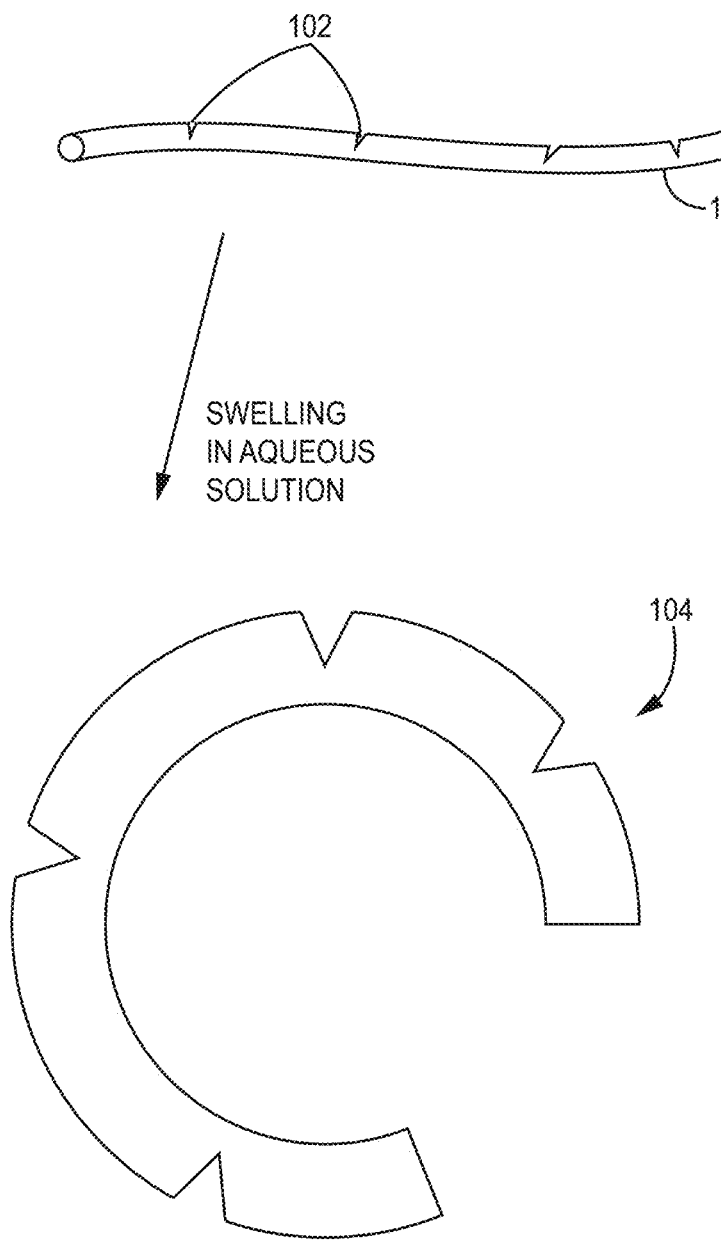
FIG. 4 is an illustration of a rod-shaped depot with a plurality of scores or weakened areas that facilitate a change of the rod's shape in aqueous solution to a curved shaped depot
Figure 5:
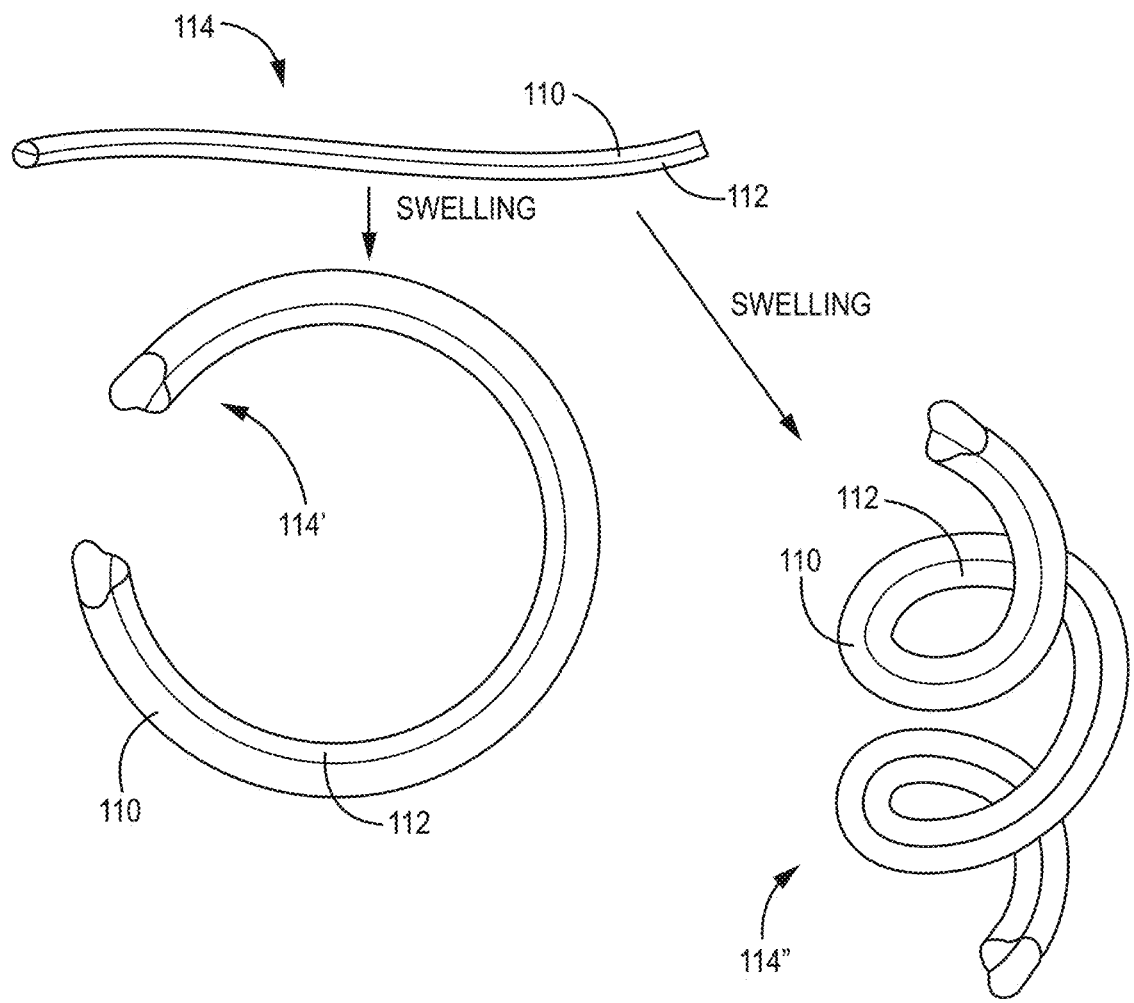
FIG. 5 is an illustration of a rod-shaped depot made of two layers of different vehicle materials, with the vehicle materials having different coefficients of swelling or elongation, so that the depot changes shape after exposure to aqueous solution.

FIG. 4 depicts one technique to make a hydrogel with a precise curve. A swellable hydrogel or a xerogel 100 that forms a hydrogel in aqueous solution is prepared with a plurality of weakened areas 102. The term xerogel, as used herein, refers to a material that forms a hydrogel in aqueous solution, regardless of whether it was created as an organogel or hydrogel. When swellable vehicle 100 swells in aqueous solution, it adopts a curved shape 104. The weakened area may be, e.g., a tear, crack, or void, (collectively referred to as notches). The notch can be performed with a tool applied directly to a site of the intended notch or other weakened area or indirectly by stretching the fiber to form necks and/or notches. FIG. 5 depicts another technique wherein two hydrogels 110, 112 are joined together to form a biopolymer hydrogel or xerogel 114. In aqueous solution, hydrogel 110 elongates more than hydrogel 112 and the material 114 forms a more complex shape, e.g., a ring 114' or a coiled 114" shape. This bipolymer technique may be combined with notching or weakening. A pairing of two hydrogels herein is referred to as bipolymeric although they may be formed from the same or from different precursors; the processing conditions and details of structure of the hydrogels can be manipulated to give them different properties. Moreover, besides using two hydrogels, a plurality of hydrogels may be used to make a multipolymeric material and the term bipolymer is not limited to two hydrogels.

Figure 6:
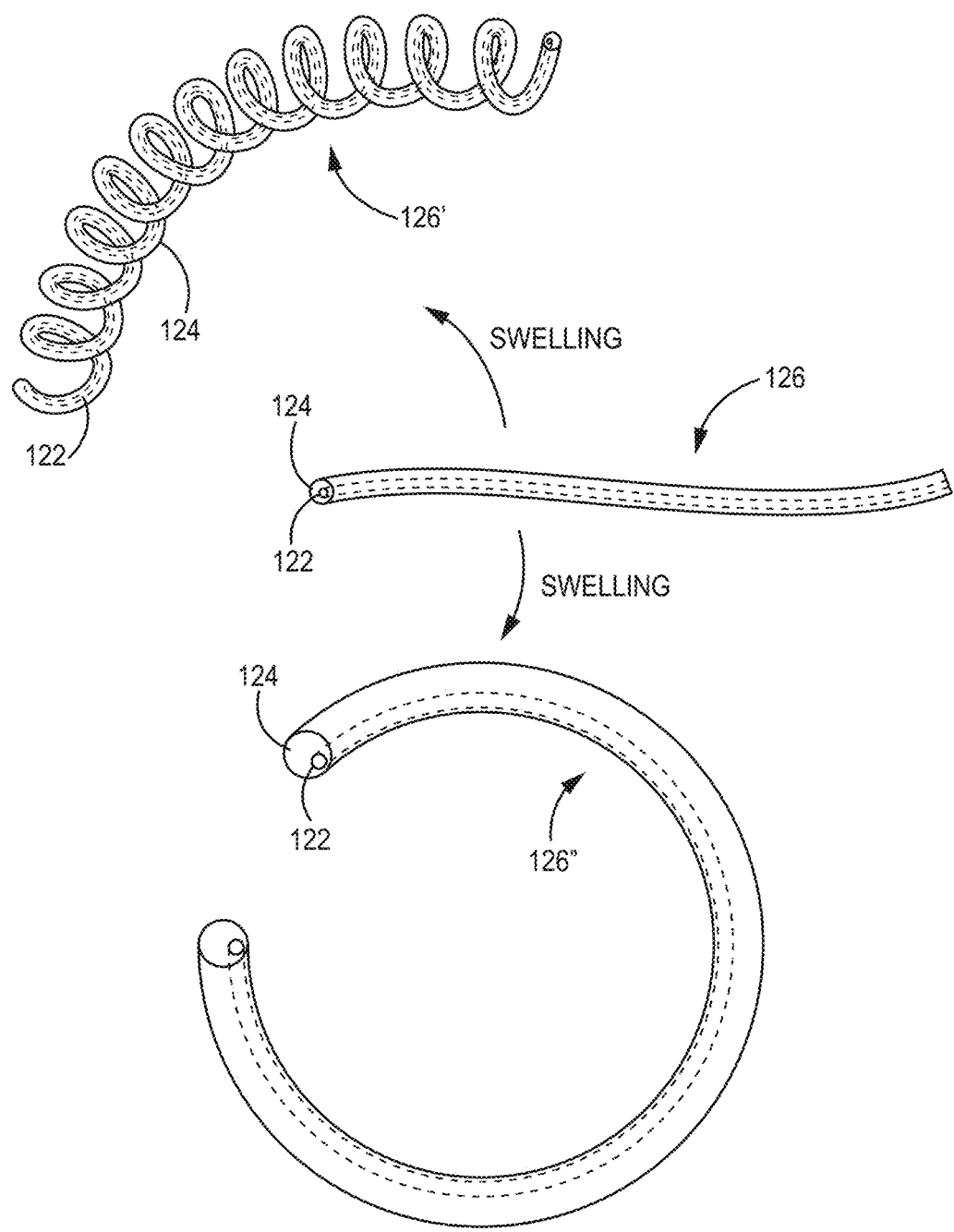
FIG. 6 is an illustration of a rod-shaped depot made with one material making a layer around another material, with the materials having different coefficients of swelling or elongation, so that the depot changes shape after exposure to aqueous solution.

FIG. 6 depicts an embedded biopolymer technique, wherein a first hydrogel 122 is encapsulated with another hydrogel 124 to make vehicle 126. In this context, encapsulated means that one of the hydrogels is inside the other, although there may be some portions that are thinly covered or not at all covered by the encapsulating polymer: the encapsulation does not have to be complete. The term substantially completely encapsulated means at least about 90% of a surface area of a hydrogel is covered-up by the encapsulating material. Encapsulation can provide improved unity between the two hydrogels, with the encapsulated hydrogel being unable to be released if there is low adherence or slipping at the interface with the other hydrogel. One or more hydrogels can be encapsulated by an encapsulating hydrogel, with a plurality of the encapsulated hydrogels providing greater mechanical unity and/or increased curvatures or a faster rate of curling when placed into solution. In this instance, hydrogel 122 has a lesser coefficient of elongation relative to hydrogel 124. Hydrogel 124 is prepared to be a xerogel, or as a hydrogel that is less than fully hydrated relative to its equilibrium hydration in a physiological solution, and is placed into a tissue where it imbibes a physiological solution, which is assumed to be aqueous. The inside hydrogel 122 does not elongate as much as outer hydrogel 124; consequently the swollen bipolymer hydrogel 126 adopts a curved shape, e.g., coil 126; or ring shape 126". The term ring is broad and includes portions of a circle, e.g., C-ring, half-ring, or a complete ring.

Figure 7A:
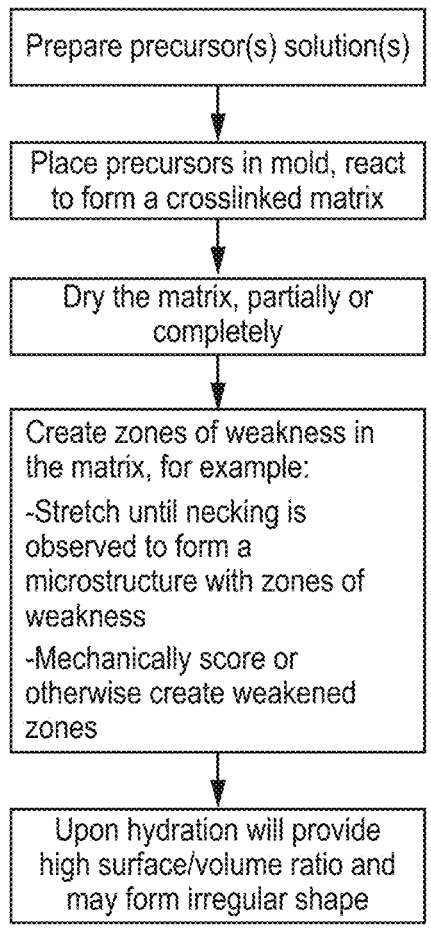
FIGS. 7A-7B set forth processes of making the vehicles of FIG. 5 or 6.

FIG. 7A is a flowchart exemplifying how to make a shape-changing hydrogel material. A precursor (meaning one or more precursors, as may be needed to make a crosslinked matrix) is prepared in a solution (aqueous or organic) and reacted in a mold. The mold may be a tube or other shape. The matrix is dried, with lyophilization being a useful technique. Zones of weakness are directly or indirectly created. When hydrated, the weakness provides for irregular shapes to be formed, or predetermined shapes for zones created with a particular shape as an end goal. In contrast, a hydrogel made without a weak area will tend to change shape uniformly, usually by swelling in all directions unless steps have been taken to make it preferentially swell in certain dimensions, or even to shrink in some dimensions while swelling in other directions. Fibers that have been stretched to a necking point will exhibit shrinkage in length when exposed to aqueous solution or solvents that wet the matrix; necking is discussed in detail below.

Figure 7B:
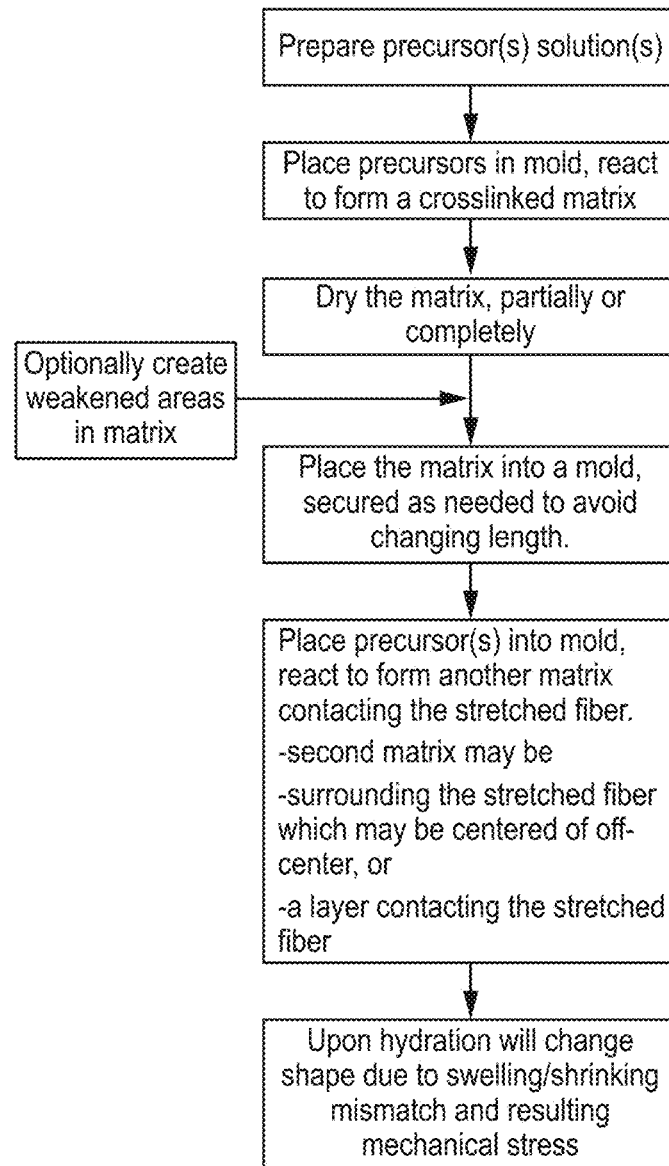

FIG. 7B is a flowchart for a process of making a bipolymer material. Precursors are crosslinked to form a hydrogel or organogel matrix. The resultant matrix is dried. Optionally, it may be treated to create weakened areas. In this embodiment, the matrix (typically a rod or strand) is secured on its ends to prevent its length from decreasing, particularly if it has been stretched, as in this embodiment. A second precursor is introduced into the mold and is crosslinked around the first matrix. The solvent for the second precursor will generally be one that wets the matrix of the first matrix, which will exhibit a tendency to shrink but cannot do so because it is secured at its ends. The interior hydrogel may be in the center of the mold or in contact with a side of the mold. The outer matrix and the inner matrix are chosen to have different swelling and/or shrinking properties. When these are sufficiently different, the resultant bipolymer material will exhibit a complex or precisely engineered shape upon hydration. An example of a complex shape is a shape that, due to an increased effective cross-section, has an increased resistance to movement through fluid, especially viscous fluid such as found in a vitreous humor. Accordingly, a complex shape includes shapes that, relative to a sphere or a rod, have a drag coefficient that is increased by a factor of 1.5 to 100; Artisans will immediately appreciate that all ranges and values between the explicitly stated bounds are contemplated, with, e.g., any of the following being available as an upper or lower limit: 1.5, 2, 3, 5, 10, 20, 25, 50, 75, 90, 100. Artisans will appreciate how to make multipolymer materials, e.g., by making a plurality of rods or strands and encapsulating them in an encapsulating matrix.

Figure 8:
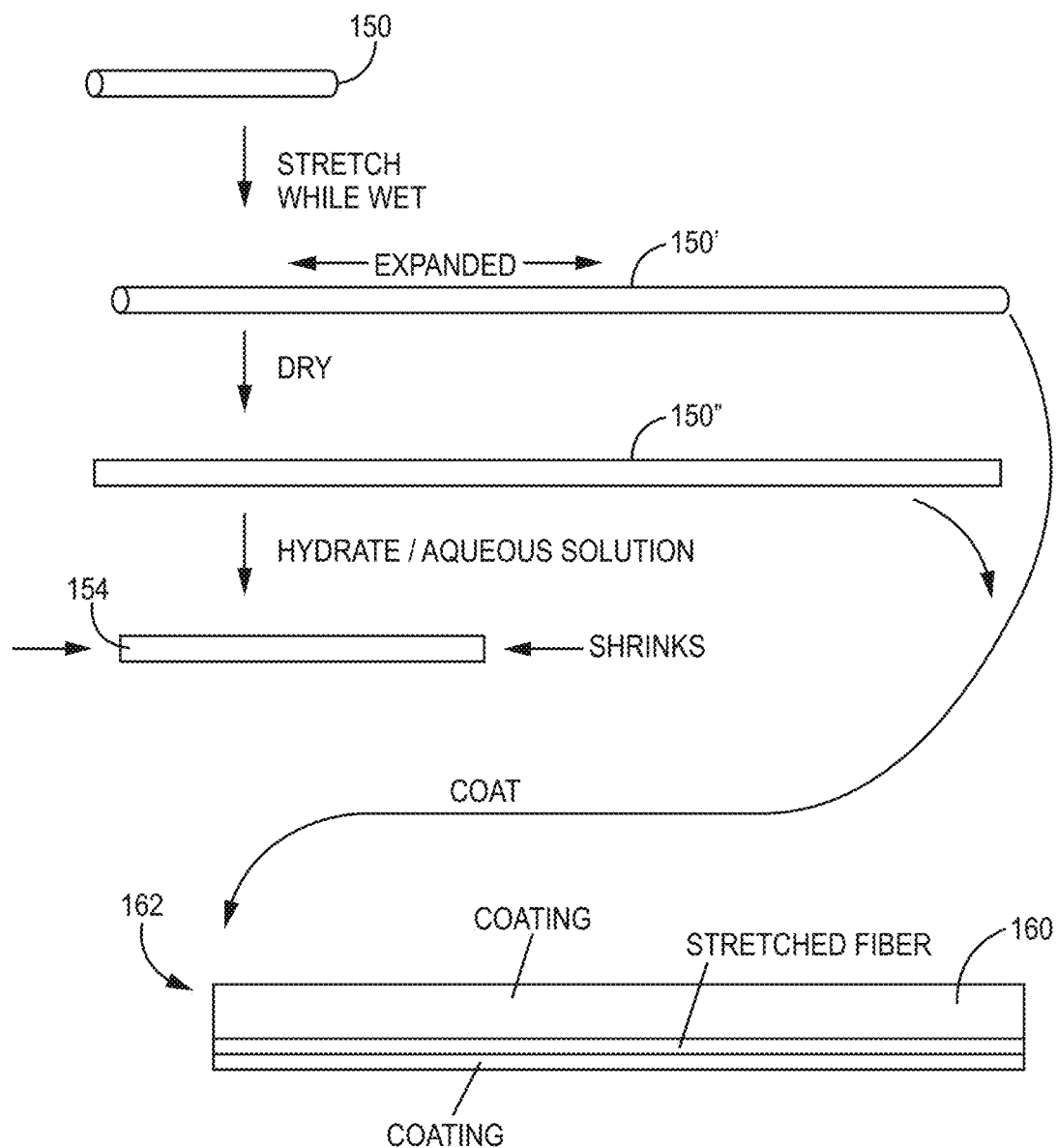
FIG. 8 illustrates a process of making a vehicle as in FIG. 6.

FIG. 8 is an illustration of various embodiments for making a bi- or multipolymer. A precursor may be cross-linked to form matrix 150 that is stretched 150' while it is still wet. This matrix 150' can then coated with another precursor that forms second matrix 160 to make bipolymer vehicle 162 by coating it (a broad term including encapsulation). Alternatively, stretched matrix 150' can be dried and held at a constant length, or otherwise limited during drying to shrinking less than it would otherwise do so, to form dried stretched matrix 150". Matrix 150" can, in turn, be used to make bipolymer vehicle 162. Alternatively, matrix 150" can be rehydrated and allowed to shrink to form hydrated matrix 154, which can be used in a biopolymer or other purposes (not shown). The agent can be in the inner and/or outer hydrogel, either directly in the matrix or in an encapsulated form.

Figure 9:
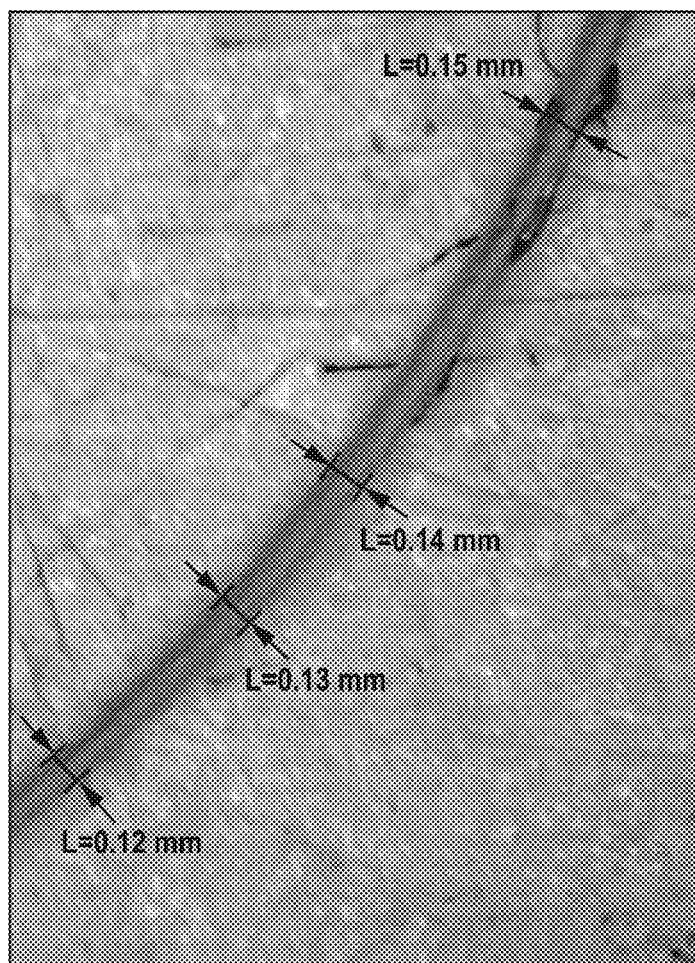
FIG. 9 is a photomicrograph of a dried vehicle comprising a second material disposed as a layer over a first material, prepared as set forth in Example 1; 30× magnification, with diameter dimension measurements.
Figure 10A:
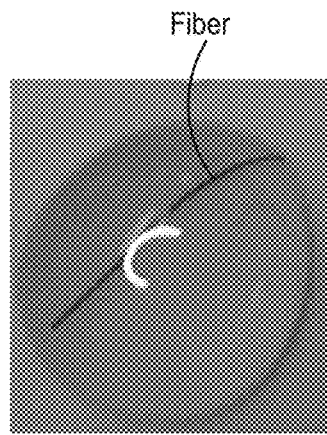
FIGS. 10A-10C depicts three successive images that show the change of the vehicle of FIG. 9 from an initial rod shape to a helical shape in aqueous physiological buffered saline solution.
Figure 10B:
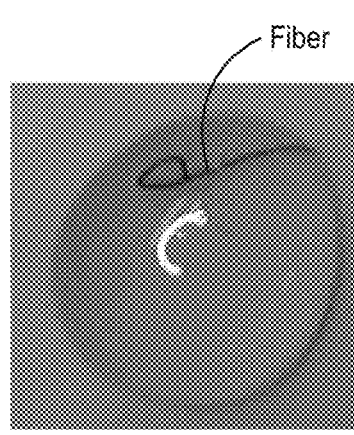
Figure 10C:
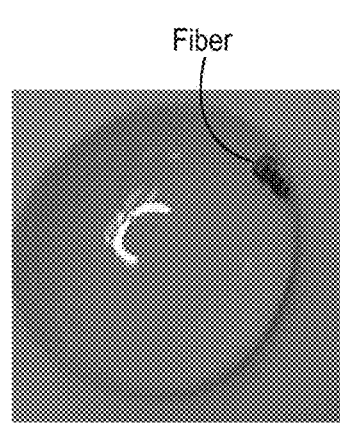
Figure 11A:
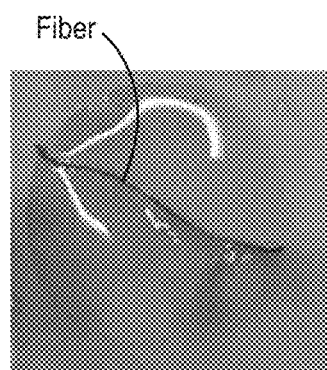
FIGS. 11A-11C depict three successive images that show the change of the vehicle of FIG. 9 from an initial rod shape to a helical shape in a viscous, aqueous physiological buffered saline solution that comprises hyaluronic acid.
Figure 11B:
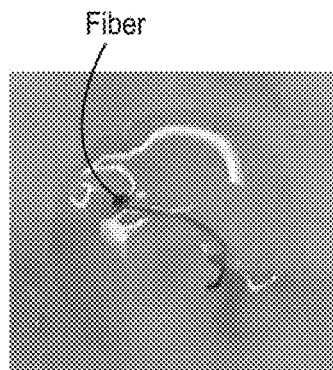
Figure 11C:
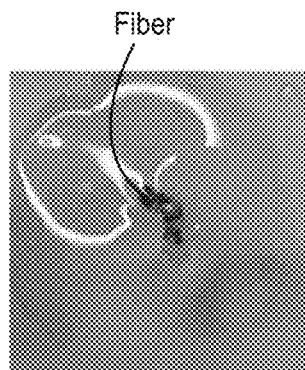
Figure 12A:
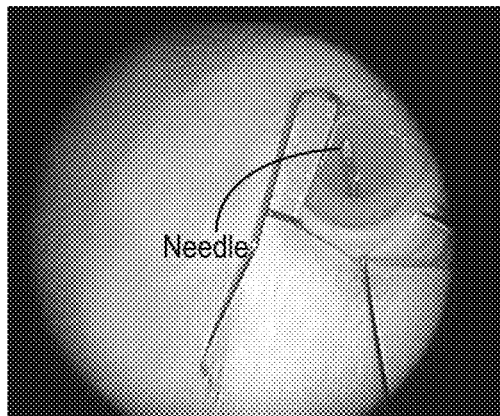
FIGS. 12A-12D depict four successive images that show the change of the shape of a vehicle prepared as described in Example 1 from an initial rod shape to a helical shape in a rabbit eye.
Figure 12B:
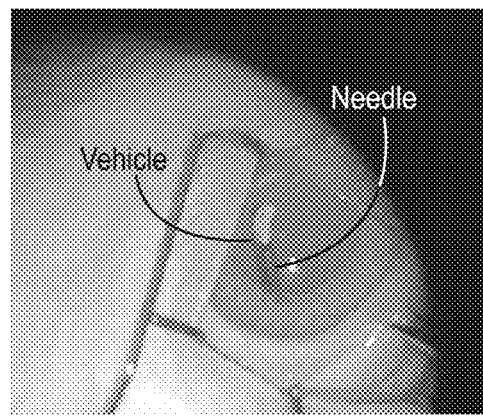
Figure 12C:
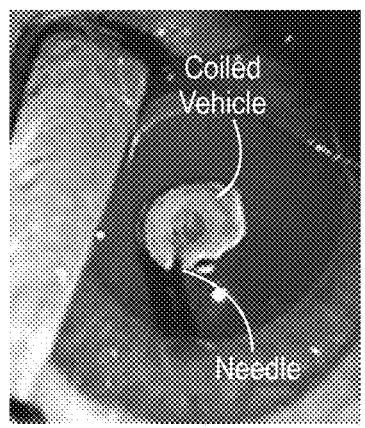
Figure 12D:
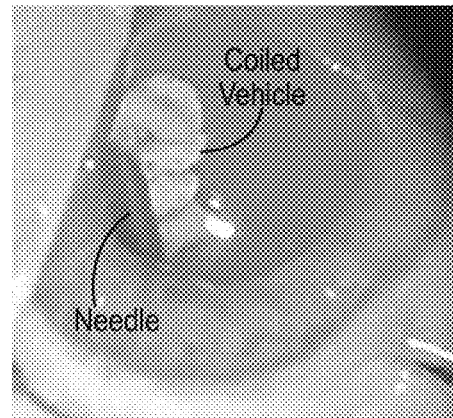
Figure 13A:
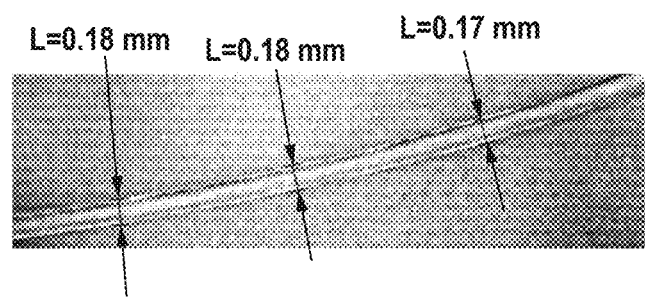
FIG. 13A is a photograph of a vehicle made according to Example 3A.
Figure 13B:
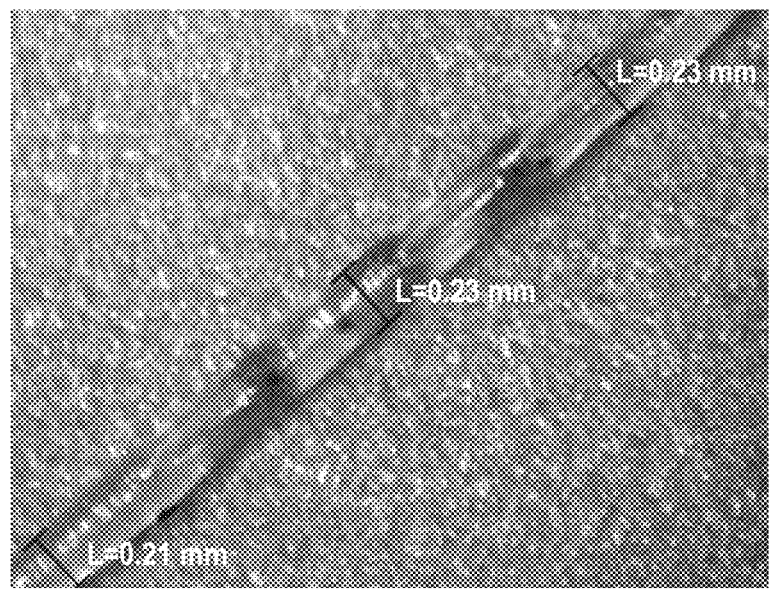
FIG. 13B is a photograph of a vehicle made according to Example 3B.

Example 1 describes the making of a bipolymer fiber that adopts a coiled shape upon hydration. A first solution was made from an electrophilic precursor (a multi-armed polyethylene glycol terminated with succinimidyl glutarate) and second solution was made with an electrophilic precursor (a multiarmed polyethylene glycol terminated with amines). The solutions were mixed and introduced into a tubular mold. The precursors crosslinked to form a matrix that was dried into a fiber shape. The fiber was stretched to about four times its original length and was observed to undergo necking, which is discussed elsewhere herein. The fiber was placed into a long tubular mold with its ends exposed, pulled taut, and the ends were secured. The tubular mold was bent around a curved surface so that the fiber was held to one of the sides of the mold. A mixture of electrophilic and nucleophilic precursors was injected into the mold and allowed to crosslink in contact with the dried fiber. The resultant material was dried and cut into 1 cm lengths, and had a diameter of 0.12-0.15 mm (FIG. 9). The bipolymer vehicle coiled into a helical shape within 10 seconds of exposure to a physiological buffer solution (FIGS. 10A-10C), even in a highly viscous solution (FIGS. 11A-11C). When injected into a rabbit eye, FIGS. 12A-12D, the bipolymer vehicle rapidly coiled as it was ejected from the needle, within about 15 seconds. Examples 3A (FIG. 13A) and 3B (FIGS. 13B-13D) demonstrate further embodiments of the making of a bipolymer vehicle.

Figure 13C:
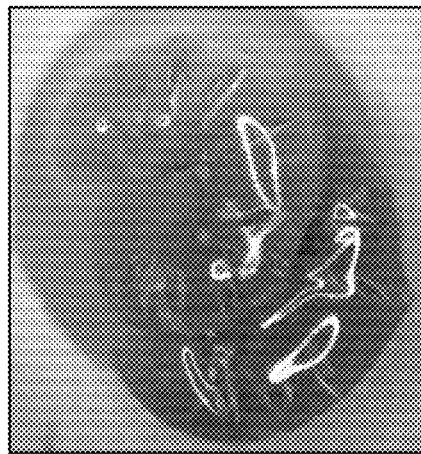
FIGS. 13C-13D are two images of a single coiled fiber made according to Example 3B.
Figure 13D:
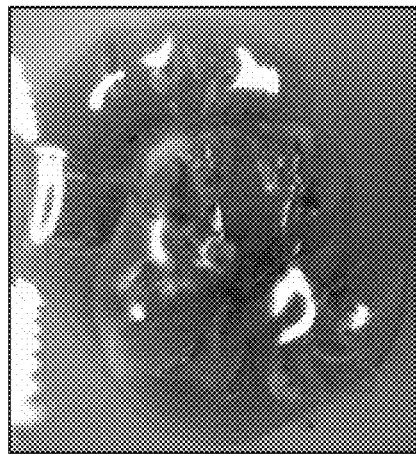
Figure 14A:
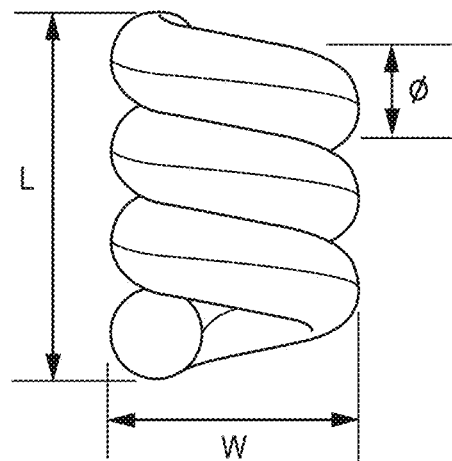
FIGS. 14A-14B are illustrations of the dimensions of a hydrated, coiled fiber made according to Example 6, at t=30 minutes.
Figure 14B:
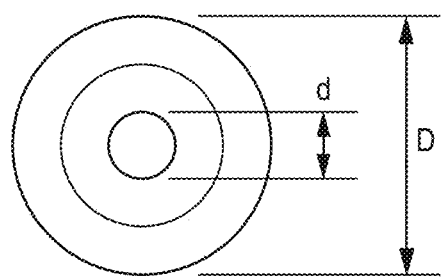
Figure 16A:
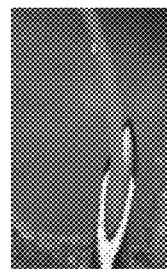
FIGS. 16A-16C are images of a dry fiber depot and a hydrated, coiled fiber depot made by the process of Example 11; before (16A) or after (16B, 16C) hydration.
Figure 16B:
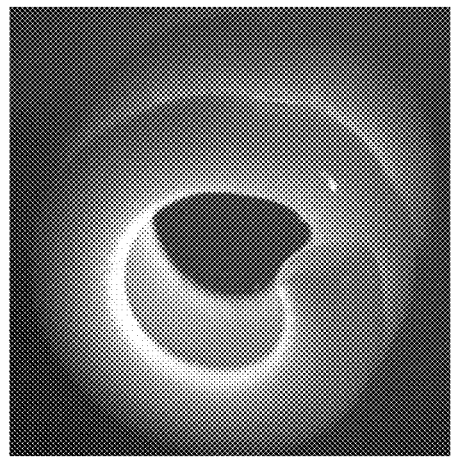
Figure 16C:
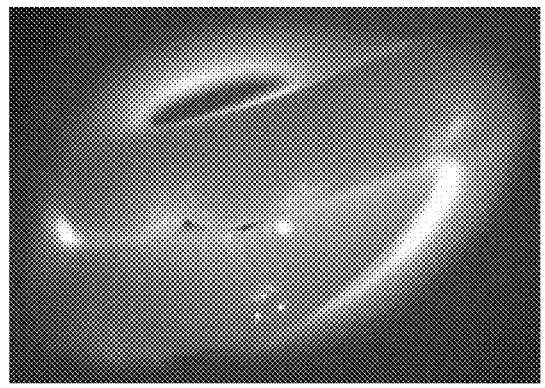
Figure 17A:
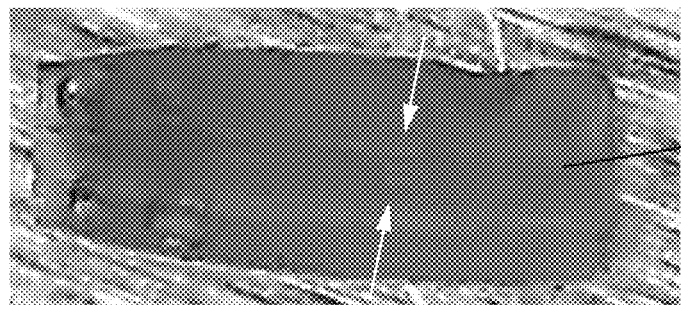
FIGS. 17A-17B are images of a hydrogel depot with a drug-loaded coating in a crescent shape with fast-degrading necked fiber already degraded, leaving an empty column along the length of the fiber, in side view (17A) and end view (17B)
Figure 17B:
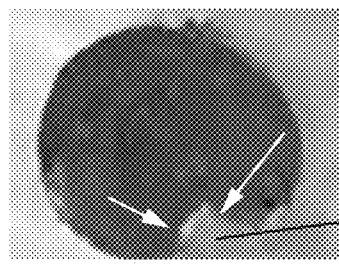
Figure 18A:
FIG. 18A is an image of a dry fiber depot (coating and necked fiber system) loaded into a 27 gauge TW needle.
Figure 18B:
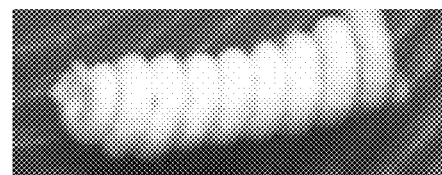
FIG. 18B is an image of a hydrated and coiled fiber depot on a fingertip (agent: axitinib)
Figure 18C:
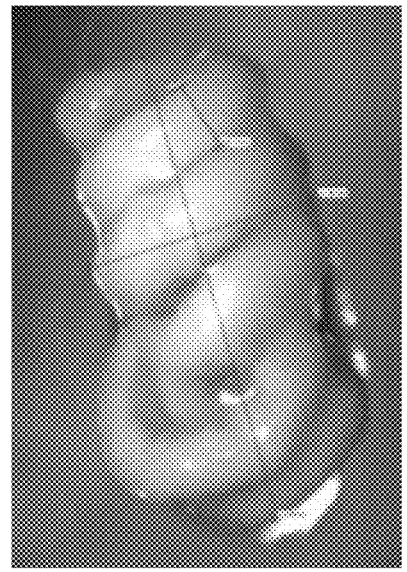
FIGS. 18C-18D are photomicrograph images of hydrated coiled fiber depots (drug: axitinib).
Figure 18D:
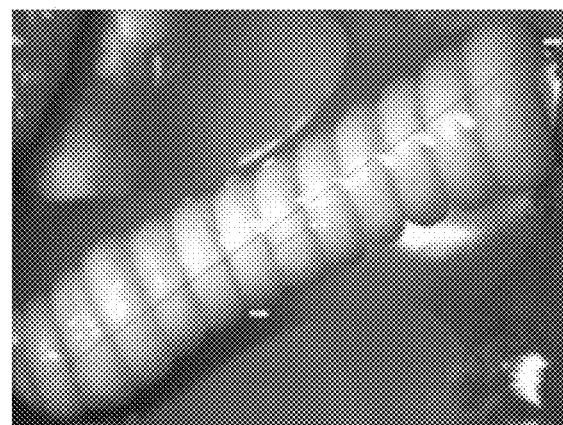

Examples 4-6 were biopolymers made with axitinib or IgG as model agents; the agents were loaded at effective concentrations without comprising the shape-changing properties of the biopolymers. The bipolymer vehicle of Example 6 (FIGS. 13B-13D) comprised fluorescein and its dimensions were measured in detail (FIGS. 14A-14B).

Example 7 described the making of a bipolymer vehicle with a rapidly degrading necked interior hydrogel. The exterior hydrogel comprises the agent to be delivered. The interior hydrogel degrades, resulting in increased exposed surface area once the necked portion has dissolved. Changing the geometry of the necked portion, particularly the diameter, changes the available drug delivery surface area. Example 8 presents a further embodiment, and Example 9 has details for a process of micronizing a therapeutic agent by precipitation. Examples 10 (FIGS. 15A-15F) and 11 detail various methods of making bipolymer vehicles. FIGS. 16A-16B, 17A-17B, and 18A-18D are further images of bipolymer vehicles made by these various processes.

Example 12 reports the results of tests on biopolymers made according to Examples 3A and 3B. It was observed that a hydrogel that was derived from an organogel had a longer persistence in vivo as compared to a hydrogel that was derived from a hydrogel. This result showed that it is possible to use the same precursors in both an interior hydrogel and in an exterior hydrogel of a bipolymer vehicle. The organogel derived hydrogel is believed to last longer due to a higher degree of crosslinking achieved in the organic solvent, which was anhydrous. A bipolymer vehicle can therefore maintain a coiled form until the outer hydrogel is fully degraded. This feature is useful because early degradation of the interior hydrogel allows the outer hydrogel to change into a less compact shape, e.g., uncoil, which is not desirable in a confined space such as a vitreous humor.

Example 13 (FIG. 19) describes a series of bipolymer vehicles made with a varying number of encapsulated hydrogels. It was observed that increasing a number of the interior hydrogels accelerated the rate of coiling. Fast coiling is advantageous for introduction into a sensitive area such as an eye because the coiling will take place quickly and minimize potential harm to the tissue that could be caused by a rapid introduction of slower coiling depots. Example 14 (FIG. 20) describes a series of bipolymer vehicles made with varying diameters of encapsulated hydrogels while an outer dimension of the vehicle was held constant. Larger inner hydrogels provided faster coiling. Coil times were less than 30 seconds; Artisans will immediately appreciate that all ranges and values between the explicitly stated bounds are contemplated, with, e.g., any of the following being available as an upper or lower limit: 30, 25, 20, 15, 10, 5, 4, 3, 2, 1 seconds.

Examples 15 and 16 (FIGS. 21-22) describe use of a plurality of bipolymers to provide a vehicle. Instead of placing a monolithic (only one in number) bipolymer vehicle, a plurality of bipolymer segments are provided. A rod or a long fiber can be cut into multiple segments to enable injection into cavities or spaces that are limited in size. For example, the eye has about a 24 mm inside diameter. Injecting a 60 mm fiber would potentially impinge on the distal retina if it did not coil quickly enough, causing damage to the delicate tissue. The segments can be cut to less than 24 mm and placed end to end in an applicator lumen (e.g. a hypodermic needle). The segments may be designed to slide parallel to each other as they exit the applicator so that they coil into a single mass, due to entanglement. The fiber may be cut on an angle to facilitate a sideways movement relative to the preceding segment as they exit the lumen of the applicator into the eye, so the following segment stops pushing the preceding segment and slides alongside it. Thus, an equal mass of depot can be safely administered. It was observed that the rate of fiber entanglement post injection and also the fiber injection distance decreased as fiber segment length decreased. A decreased fiber injection distance creates a safer injection with lower risks of fiber segments pushing each other (termed fiber training) and contacting the interior walls of the eye. It was further observed that cutting the ends of the fiber at an angle could be used to reduce fiber training, with an angle ranging from more than 30 to less than 60 being useful (perpendicular cut is 0 degrees); Artisans will immediately appreciate that all ranges and values between the explicitly stated bounds are contemplated, with, e.g., any of the following being available as an upper or lower limit: 30, 31, 35, 40, 45, 50, 52.5, 55, 59, 60 degrees. Embodiments include a plurality of vehicles that collectively are administered to a tissue, with the vehicles comprising such an angle and being delivered together in a single injection or other single administration.

Figure 23:
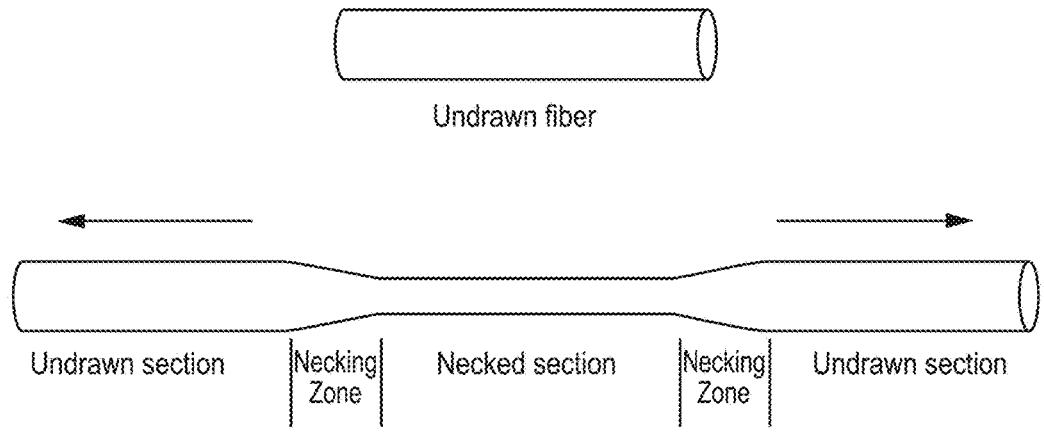
FIG. 23 is an illustration of a necking mechanism for a dry fiber.
Figure 24:
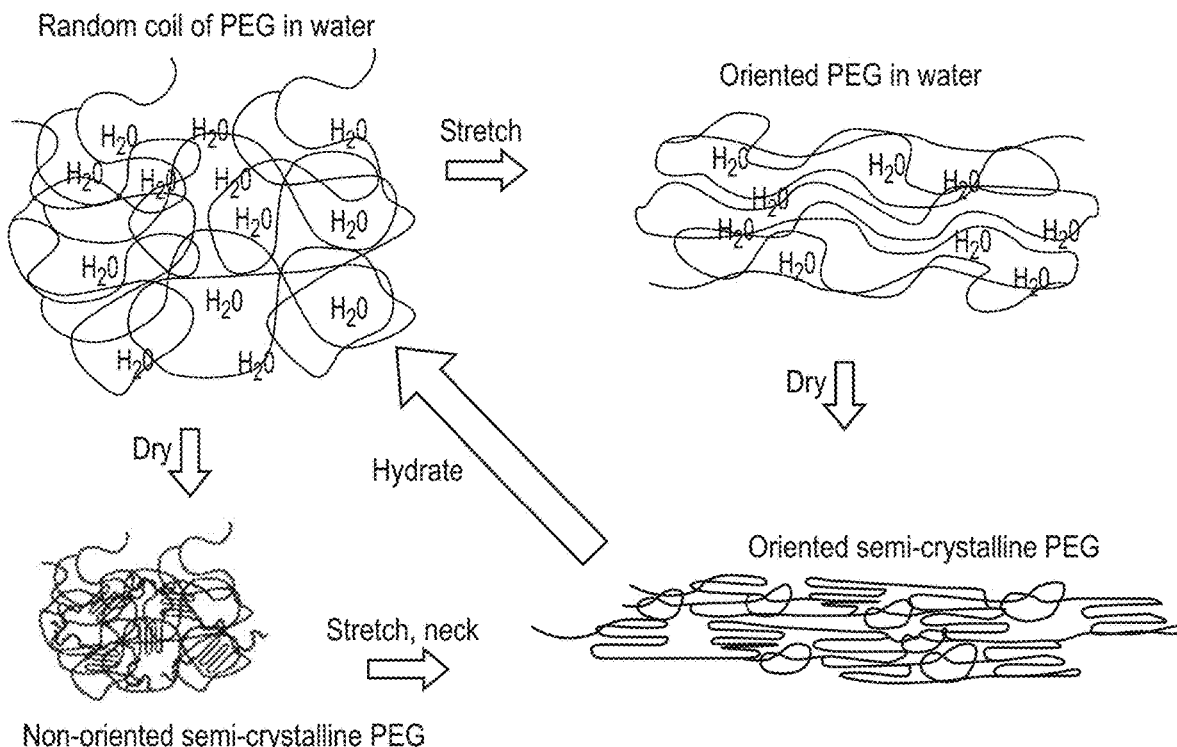
FIG. 24 is an illustration of the role of crystallinity in a necking process. The crystalline regions providing dimensional stability to the depot, until the depot is placed in solvent (e.g. water or body fluid) or heated above the melting point.

FIG. 23 illustrates necking, which is a term that describes plastic deformation of the hydrogel/xerogel/organogel as it is stretched. As the fiber is stretched, it will begin to elongate and become thinner. The matrix is crosslinked, so pulling it longitudinally causes a collapse of the diameter (or other width for a non-circular object). The thinned portion experiences orientation of the matrix. Embodiments include a crosslinked hydrogel/xerogel/organogel matrix of a semicrystalline material that has been pulled in the axial direction to cause necking to occur. The term semicrystalline is known in the polymer arts. FIG. 24 depicts orientation of a semicrystalline matrix. As formed, the matrix is a crosslink of polymers in a random coil configuration. When stretched, the matrix orients along the axis of stretching. If dried, the matrix keeps this shape because of the association of microdomains in the matrix, particularly crystals that form between polymers. For example, a polymeric material that crystallizes or has increased crystallization when stretched will decrease in length when the conditions are changed to allow the crystallinity to decrease. Vehicles (hydrogels or organogels) can be stretched and dried and allowed to crystallize to a semicrystalline, dimensionally stable configuration so that, upon hydration, the vehicles will contract as the crystallized domains decrease. Alternatively, vehicles comprising hydrogels or organogels can be dried to xerogels and allowed to crystallize and then stretched (optionally with heating) to a semicrystalline, dimensionally stable rod, upon hydration, the vehicles will contract as the crystallized domains decrease. Or a crosslinked hydrogel or organogel can be stretched while wet to a specific length and held at that length until the solvent has evaporated leaving the semicrystalline, oriented fiber. Alternatively, the crosslinked hydrogel or organogel can be allowed to dry to an unoriented fiber or rod that is semicrystalline. Upon drawing, the fiber will neck to a characteristic draw ratio that is dependent on the molecular weight between crosslinks. The addition of a therapeutic agent or other material also influences the characteristic necking draw ratio, with experiments showing that effective amounts of the agents can be accommodated without undue disruption of necking structure.

Example 17 describes an in vivo test for delivery of a therapeutic agent from a necked rod (FIGS. 25A-25C) or a coiling bipolymer (FIGS. 26A-26C). The vehicles rapidly hydrated upon placement in the vitreous and delivered more than 4000× an effective amount for six months. The delivery time could readily be adjusted for longer times of delivery of an effective concentration of the agent by increasing persistence of the matrices. Axitinib was chosen as a clinically relevant model for these tests. The delivered amounts are not toxic.

Shape Changing Devices

Drug delivery depots may be created that have a first shape ex vivo and change to a second shape in vivo. An initial thin and elongated shape is useful for placement because it minimizes trauma of placement into the target tissue. The second shape provides advantages such as a more compact shape or a shape with advantages for the targeted space. For instance a change in shape after placement in an ear cavity can aid in retention, or a change of shape after placement in a sinus cavity can aid retention and delivery of drugs. In the context of an eye, a compact shape allows for the device to be out of visual pathway and to resist migration over time. Embodiments include providing a shape and/or a volume change of the vehicle that reduces a tendency of the vehicle to migrate from the site where it is initially placed in a tissue or tissue fluid compared to an object of the shape and dimensions of the vehicle before the shape change. Accordingly, an object that is not straight, is not round, is arbitrarily non-linearly folded, or is coiled can more readily resist migration due to an increased effective cross-section, making it more resistant to movement through fluid, especially viscous fluid such as vitreous humor. Further, using a shape changing vehicle provides for passing the vehicle through an opening and placement at a tissue, with the change in shape and a volume change of the vehicle preventing expulsion of the vehicle through the opening. The opening, for instance, may be a puncture, a puncture made with a needle, an entry wound, or a pre-existing passage. The term passage is a broad term that includes natural pores, passages created by trauma or disease, natural or artificial lumens or voids.

An embodiment of the invention is a vehicle or prosthesis with an initial aspect ratio that changes to a different aspect ratio (as-deployed or as-placed) after deployment. The aspect ratio of a vehicle describes the proportional relationship between its shortest side and its longest side (maximum length). It is commonly expressed as two numbers separated by a colon, as in 1:25. Embodiments include having an aspect ratio before and after placement that is independently selected from 1:1 to 1:100,000; Artisans will immediately appreciate that all ranges and values between the explicitly stated bounds are contemplated, with, e.g., any of the following being available as an upper or lower limit: 1:2, 1:4, 1:10, 1:25, 1:50, 1:100, 1:200, 1:500, 1:1000, 1:2000, 1:3000, 1:5000, 1:10000, 1:50000, 1:80000, 1:90000. Accordingly, embodiments include, for example, an initial aspect ratio of 1:100 and an aspect ratio after placement of 1:50.

The terms vehicle, depot, and prosthesis are used interchangeably herein. A vehicle refers to a substance, usually without therapeutic action, used as a medium to give bulk for the administration of medicines. A hydrogel that contains a drug for release is a vehicle. The term prosthesis similarly refers to a device that is used as a medical aid. The term depot is a drug delivery construct comprising a vehicle or prosthesis and an active pharmaceutical agent.

An embodiment of the invention is a depot or prosthesis comprising a vehicle shaped as a thin rod that curls to a curved shape after placement. The term curled is a broad term that refers to a curved shape, which is a broad term that also includes more specific shapes e.g., a coil, a spiral, a helix, a rolled sheet, a cylinder, or a twisted sheet as well as irregularly curved shapes such as straight rod changed into a randomly curving structure. Embodiments include a vehicle with an initial shape, before placement or after placement or a combination thereof of: a rod, sheet, curled sheet, rolled sheet, cylinder, prism (rectangular, cube, triangular, octagonal, etc.), sphere (perfect, ellipsoidal etc.), cone, curled, coil, curved, etc. The term rod is broad and refers to an object that is longer than it is wide, such as fibers or ribbons; the term is not limited to cylinders, so the cross-sectional shape can be varied. The term coiled, in the context of a coiled vehicle, refers to a series of loops, including loops that change direction. For example, a coiled telephone cord has a series of loops and can sometimes form loops that reverse direction, as in from a left-handed to a right handed helix.

An embodiment of the invention is a depot or prosthesis comprising a vehicle that has a first effective gauge that changes to a larger effective gauge after changing shape in response to the physiological fluid. The effective gauge of a depot or prosthesis is a term that refers to the smallest diameter passage of at least 5 mm in length that the depot or prosthesis can pass through without being deformed. Needles are commonly rated according to a gauge, which is a measure of the largest dimension of an object that could be passed through the needle. The nominal needle gauge rating is not necessarily the true effective gauge of a needle because the needle has a nominal inner diameter and a tolerance. Needle gauges are numerical values that increase as the outer diameter of the needle decreases. The inner diameter of the needle depends on the needle gauge and the wall thickness, often referred to as regular wall, thin wall, extra-thin wall and ultra-thin wall by various manufacturers. In addition, the wall thickness is typically controlled to a tolerance, such that the depot or prosthesis diameter should be no greater than the minimum diameter of the tolerance range of the needle inside diameter. Embodiments include a depot or prosthesis that has a first effective gauge before deployment and a second effective gauge after deployment (after exposure to aqueous solution) independently selected from 0.001 mm to 10 mm; Artisans will immediately appreciate that all ranges and values between the explicitly stated bounds are contemplated, with, e.g., any of the following being available as an upper or lower limit: 0.005, 0.002, 0.003, 0.005, 0.01, 0.02, 0.03, 0.04, 0.05, 0.07, 0.1, 0.15, 0.2, 0.25, 0.3, 0.5, 0.6, 0.8. 1, 1.5, 2, 2.5, 3, 3.5, 4, 4.5 mm. In general the first effective gauge is smaller than the effective gauge after deployment, although a vehicle that changes in the opposite direction may also be made and used. Embodiments also include a depot or prosthesis that can be introduced through a needle having a gauge (referring to customary needle sizing) of 24, 25, 26, 26s, 27, 28, 29, 30, 31, 32, 33, or 34. As is evident, the vehicles may be chosen to have any combination of shape, aspect ratio, effective gauge, or sizing before or after placement and such combinations may be freely mixed and matches as guided by the need to make an operable embodiment. Long rod shapes that shrink in length and increase in width after exposure to aqueous solution are useful in many situations.

An embodiment of the invention is a vehicle that comprises a first material with a first coefficient of elongation in physiological solution and a second material that has a second coefficient of elongation in physiological solution, with first and second coefficients of elongation being different. The terms first material and second material are arbitrary to signify materials that are different in composition and/or properties. The term coefficient of elongation of a material refers to change of length of the material in a dry state that is placed into aqueous solution. The length refers to the most extended dimension of an object. A coefficient of less than 1 means that the material becomes shorter when exposed to water; a coefficient of more than 1 means that the material becomes longer. An embodiment of the invention is a vehicle that comprises a first material that has a first coefficient of swelling in physiological solution and the second material has a second coefficient of swelling in physiological solution, with first and second coefficients of swelling being different. The term coefficient of swelling of a material refers to a change of volume of the material in a dry state that is placed into aqueous solution. A coefficient of less than 1 means that the material becomes smaller in volume when exposed to water; a coefficient of more than 1 means that the material becomes larger in volume. A cross-linked semicrystalline material that has been stretched may have a coefficient of elongation less than 1, but a coefficient of swelling greater than 1. The coefficients are evaluated at physiological temperature.

The Examples provided herein provide multiple working embodiments. An embodiment of making a shape-changing vehicle is to form a layer of a second material around a first, stretched, material. The first material is chosen and stretched so that it becomes shorter when exposed to a physiological solution. The term layer is broad and refers to a complete encapsulation of one material by another, a partial overlay of materials, a continuous contact area between materials, or a joining of materials that contact with each other with or without overlap at all areas or having some zones of discontinuity in an otherwise contacting-relationship.

The first material and the second material may be independently chosen from, for example: a hydrogel, an organogel, a xerogel, polylactic acid (PLA), polyglycolic acid (PGA), a copolymer of PLA and PGA (PLGA), a precursor material as set forth herein, natural, synthetic, or biosynthetic polymers. Natural polymers may include glycosminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof, other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum crosslinked with a polyol such as propylene glycol, poly(hydroxyalkyl methacrylate), poly(electrolyte complexes), poly(vinylacetate) cross-linked with hydrolysable or otherwise degradable bonds, and water-swellable N-vinyl lactams. Other hydrogels include hydrophilic hydrogels known as CARBOPOL®, an acidic carboxy polymer (Carbomer resins are high molecular weight, allylpentaerythritol-crosslinked, acrylic acid-based polymers, modified with C10-C30 alkyl acrylates), polyacrylamides, polyacrylic acid, starch graft copolymers, acrylate polymer, ester cross-linked polyglucan, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids) dextran, or a protein. a macromolecule, a crosslinkable, biodegradable, water-soluble macromer, natural proteins or polysaccharides may be adapted for use with these methods, e.g., collagens, fibrin(ogen)s, albumins, alginates, hyaluronic acid, and heparins a polyethylene glycol-containing precursor. The hydrogels, organogels, and xerogels may comprise one more precursors as set forth below. An embodiment is a PLA fiber, PGA fiber, or a PLGA fiber coated with a hydrogel.

Embodiments include stretching polymeric materials until their structure is characterized by many small defects, such as tears, cracks, voids, or other weakened areas are set forth herein. The term necking, as described herein, refers to such a stretching process. In general, it has been found that it is useful to choose materials for stretching by a large factor, e.g., by a factor of at least two, or 2-10: Artisans will immediately appreciate that all ranges and values between the explicitly stated bounds are contemplated, with, e.g., any of the following being available as an upper or lower limit: 2, 2.5, 3, 3.5, 4, 4.5, 5, 6, 7, 8, 9, 10. An alternative to a necking process is to mechanically or otherwise introduce weakened areas into a material, particularly a rod, without necessarily stretching the material. The material is chosen and/or processed so that, upon exposure to aqueous solution, it swells, contracts, or otherwise changes shape. The weakened areas direct the resultant forces to make a desired shape, e.g., curved, coiled, or as otherwise detailed herein.

An embodiment of a process to make a shape changing material is to stretch a first polymeric material and, while the material is maintained under tension or otherwise in the stretched configuration, make a layer of a second material that contacts the stretched material. The combined bipolymeric material can be dried. The first material and the second material may be independently chosen to be, for example, a hydrogel or an organogel, in which case the dried product may comprise a xerogel. The first polymeric material may be stretched during its formation or after it is formed, e.g., formed by casting, crosslinking, covalent crosslinking, initiation of polymerization, or mixing precursors. The stretching may take place while the material is wet or dry. One or more drying steps may be performed, e.g., after making the first material (Material 1), after stretching Material 1, after forming the second material (Material 2), or after forming the combination bi-material. The process may be adapted to comprise a plurality of polymers, meaning two or more, e.g., 2, 3, 4, 5, etc. Formation, cross-linking, stretching, drying, and so forth may be performed in any order according to the principles outlined herein. The term bipolymeric means at least two polymeric materials unless otherwise specified as being limited to 2 materials.

The Material 2 layer may be on-center (concentric) or off-center (eccentric) on Material 1 (also referred to as a fiber in the case of a rod shape), which will influence the final shape in vivo. For instance, the fiber (Material 1) may be concentric in a surrounding layer (Material 2), may be eccentric, or may have portions not contacting Material 2. The term layer is broad and includes continuous or partial coatings.

Another embodiment of a shape-changing vehicle is a drug delivery depot comprising a plurality of materials joined together that have different coefficients of swelling and/or coefficients of elongation. For instance, a plurality of hydrogel layers (organogel/hydrogel/xerogel) layers may be in contact with each other, made with different swellability and/or stretched to different degrees by a necking or other process to produce different coefficients of change (elongation or swelling). In use, the vehicle is placed at the intended site where it imbibes physiological solution and the mismatch of the joined materials elongation or swelling coefficients creates a curved and/or other shape change. In addition, PLGA fibers, fibers with weakened areas or fiber segments may be used as low elongation elements with a higher or lower elongation coefficient material bonded thereto, with the resultant composite material changing shape in response to a fluid.

A device may comprise two materials joined together that swell differently on exposure to aqueous solution. On exposure to water, the differential in swelling causes them to bend or otherwise change shape, e.g., curving or coiling. For example, a swellable hydrogel comprising hydrophilic materials may be joined with a hydrogel or other material that swells to a lesser extent because it comprises hydrophobic materials, or comprises a lesser proportion of hydrophilic materials. More specifically, these could be, e.g., a first matrix of hydrophilic polymers (polyethylene glycols or other hydrophilic materials set forth herein) joined to a second matrix that comprises hydrophobic polymers (PLURONICs or other hydrophobic materials set forth herein). If other factors are comparable, such as the degree of crosslinking and matrix orientation, then the relatively more hydrophilic material will swell to a greater extent and the device will bend due to forces generated at the interface between the materials.

A vehicle that comprises a first and a second material that are joined together may be made with materials that degrade in vivo at different rates. Embodiments comprising an inner material, e.g., a rod, and a layer in contact with the inner material may be chosen so that one degrades before the other. The remaining material has an increased surface area in vivo, which affects a rate of drug delivery. For instance, embodiments with an inner material that shrinks in water to make the vehicle assume a helical or more compact or alternative shape can employ a rapidly degrading material for the inner material. Thus the remaining material, which may be the material with the drug or other agent to be delivered, may have a surface area that increases by, e.g., a factor from 1.5 to 3. Examples of relative rates of degradation are: from 1 to 10, e.g., a material that degrades 2× or 5× the rate of the other material.

The vehicles are useful as solids. The term solid means firm and stable in shape; not liquid or fluid; supports its own weight on a flat surface without deformation although it may be elastically deformable, meaning that it returns to its original shape after the deforming stress is removed.

Vehicles that change shape can serve as depots for therapeutic agents for ocular drug delivery, drug delivery at a tissue or organ, or to deliver agents at other sites. Therapeutic agents (a term including drugs and also including active pharmaceutical agents (APIs) may be added to the materials before, during, or after formation of the materials. The agents may be added directly, as solids or suspensions or solutes or colloids etc., or as embedded in drug vehicles, e.g., degradable particles. Agents that are micronized, as per examples with axitinib herein, are useful in many situations. Embodiments include agents that are particles, or are in particles, that have a maximum dimension of 0.01 to 100 microns; Artisans will immediately appreciate that all ranges and values between the explicitly stated bounds are contemplated, with, e.g., any of the following being available as an upper or lower limit: 0.01. 0.02. 0.05. 0.1, 0.5, 0.6, 1, 2, 4, 5, 6, 7, 8, 9, 10, 20, 50, 80, 90, 100 microns. The term particle is broad and encompasses spheres, drops, whiskers, and irregular shapes. Small sizes of particles help to avoid making thin materials that have breaks or are easily broken.

Introduction of vehicle may be performed as appropriate to the site of placement and use, e.g., by catheter, injection, with adhesives, in minimally invasive surgical processes, during open surgery, and so forth. One method comprises pushing the depot or prosthesis through a needle with a pusher. For instance, a thin wire with a blunt end sized to pass into the needle can be used in a syringe with a small diameter inner body so that the thin wire serves the role that a plunger would serve in a typical syringe. The term pusher is broad and refers to rods, cylinders, wires, metals, plastics or various other tools or materials for forcing a thin depot or prosthesis out of a needle.

Accordingly, the embodiments referring to a first material and a second material, a plurality of materials, or Material 1 and Material 2, may be chosen independently from the detailed list of materials set forth above or from the list of precursor materials provided below.

Anatomy of the Eye

One site for placement of a vehicle, depot or prosthesis for drug delivery is on, in, or near an eye. The structure of the mammalian eye can be divided into three main layers or tunics: the fibrous tunic, the vascular tunic, and the nervous tunic. The fibrous tunic, also known as the tunica fibrosa oculi, is the outer layer of the eyeball consisting of the cornea and sclera. The sclera is the supporting wall of the eye and gives the eye most of its white color. It is extends from the cornea (the clear front section of the eye) to the optic nerve at the back of the eye. The sclera is a fibrous, elastic and protective tissue, composed of tightly packed collagen fibrils, containing about 70% water.

Overlaying the fibrous tunic is the conjunctiva. The conjunctiva is a membrane that covers the sclera (white part of the eye) and lines the inside of the eyelids. The conjunctiva effectively surrounds, covers, and adheres to the sclera. It is has cellular and connective tissue, is somewhat elastic, and can be removed, teased away, or otherwise taken down to expose a surface area of the sclera. The vascular tunic, also known as the tunica vasculosa oculi, is the middle vascularized layer which includes the iris, ciliary body, and choroid. The choroid contains blood vessels that supply the retinal cells with oxygen and remove the waste products of respiration.

The nervous tunic, also known as the tunica nervosa oculi, is the inner sensory which includes the retina. The retina contains the photosensitive rod and cone cells and associated neurons. The retina is a relatively smooth (but curved) layer. It does have two points at which it is different; the fovea and optic disc. The fovea is a dip in the retina directly opposite the lens, which is densely packed with cone cells. The fovea is part of the macula. The fovea is largely responsible for color vision in humans, and enables high acuity, which is necessary in reading. The optic disc is a point on the retina where the optic nerve pierces the retina to connect to the nerve cells on its inside.

The mammalian eye can also be divided into two main segments: the anterior segment and the posterior segment. The anterior segment consists of an anterior and posterior chamber. The anterior chamber is located in front of the iris and posterior to the corneal endothelium and includes the pupil, iris, ciliary body and aqueous fluid. The posterior chamber is located posterior to the iris and anterior to the vitreous face where the crystalline lens and zonules fibers are positioned between an anterior and posterior capsule in an aqueous environment.

Light enters the eye, passes through the cornea, and into the first of two humors, the aqueous humour. Approximately two-thirds of the total eyes refractive power comes from the cornea which has a fixed curvature. The aqueous humor is a clear mass which connects the cornea with the lens of the eye, helps maintain the convex shape of the cornea (necessary to the convergence of light at the lens) and provides the corneal endothelium with nutrients.

The posterior segment is located posterior to the crystalline lens and in front of the retina. It represents approximately two-thirds of the eye that includes the anterior hyaloid membrane and all structures behind it: the vitreous humor, retina, and optic nerve. On the other side of the lens is the second humour, the vitreous humour, which is bounded on all sides: by the lens, ciliary body, suspensory ligaments and by the retina. It lets light through without refraction, helps maintain the shape of the eye and suspends the delicate lens.

FIG. 1 depicts eye 10 having sclera 12, iris 14, pupil 16, and eyelid 18. FIG. 2 depicts a perspective view of eye 10 with a partial cross-section that depicts lens 20, inferior oblique muscle 21, medial rectus muscle 23, and optic nerve 25. FIG. 3 is a cross-section of eye 10 and depicts cornea 22 that is optically clear and allows light to pass iris 14 and penetrate lens 20. Anterior chamber 24 underlies cornea 22 and posterior chamber 26 lies between iris 14 and lens 20. Ciliary body 28 is connected to lens 20. FIG. 3 depicts a portion of the conjunctiva 30, which overlies the sclera 12. The vitreous body 32 comprises the jelly-like vitreous humor, with hyaloid canal 34 being in the same. Fovea 36 is in the macula, retina 38 overlies choroid 37, and the zonular space is indicated at 42.

Sites for Placement and Use of a Drug Delivery Vehicle

Vehicles may be introduced at various points in, on, or near an eye. One area is topically. Another area is intravitreally. In use, for example a syringe, catheter or other device is used to deliver a vehicle, optionally through a needle, into the eye. Drugs or other therapeutic agents are released from the vehicle to the intra-ocular space. Sites of introduction include: periocular, canaliculus, punctum, lacrimal canal, on the conjunctiva, on the cornea, on a sclera, inside a sclera, on an interior wall of the eye, intraocular, invitreal, on a retina, near a retina but not touching a retina, a distance of 1 to 2000 microns from a retina, suprachoroidal, in the choroid, in a potential space, in a lumen artificially (by a user, with a tool) created to receive the depot or prosthesis, in a chamber of an eye, in the posterior chamber, in contact with vitreous humor, in the hyaline canal, or a combination thereof. An appropriate device may be chosen to deliver the vehicle, depot or prosthesis depending on the intended site of delivery. Some available devices include syringes, catheters, cannulas or trocars, which may have a needle or microneedle, for instance a needle of 27 gauge or smaller inner diameter. The term needle refers to a long, short, micro-length, sharp, or blunt needle and is a broad term that includes metal, plastic, and other materials as may be used on syringes, catheters, cannulas, trocars, and so forth. In some placement methods, a retractor is used to hold back the eyelids, and a user would create a small buttonhole in the conjunctiva about 5-6 mm from the inferior/nasal limbus and dissect the conjunctiva down through Tenon's capsule; to the bare sclera. Then, a blunt cannula (e.g., 15 mm in length) is inserted through the opening and the vehicle, depot or prosthesis is placed. The cannula is removed and the conjunctiva is closed with a cauterization device.

Vehicles may be placed at a site that is a tissue. The term tissue is broad and includes organs, potential spaces, a tissue compartment, which is a bodily space filled with fluid or gas, e.g. an eye, ear or other body cavity. Shape changing drug delivery vehicle of the various shapes, sizes, effective gauge, aspect ratios, and as otherwise described herein may be placed in or on a patient at various sites, e.g. with minimally invasive applications or processes through small existing openings or small needle holes to create space filling drug delivery depots. Examples of sites are: Vitreous humor or aqueous humor, Canaliculus and ampulla, Paranasal sinuses, Joint capsules (e.g. knee, hip, etc.), Lumpectomy site, Biopsy site, Tumor core, Ear canal, Vaginal, Bladder, Esophageal, Bronchial, Abscesses, e.g. Dental, AV malformation sites, Vascular aneurysms or dissections, potential spaces, artificially created spaces or potential spaces, pessary, buccal, anal, uretheral, nasal, breast, iatrogenic, cancer, organs, luminal spaces, natural lumen, vascular, aneurysm.

The vehicles, depots or prostheses may be sized so that, for example, they occupy some or all of the site where they are placed. Thus a sinus site could be partially occupied. In the case of sinus, bronchial, or other sites that can be accessed via tortuous paths, the change of shape is helpful to make placement or threading through passages feasible, and the change of shape provides for adequate placement and coverage at the indeed site. The change of shape—to a helix or coil for example, provides a means of securing the depot within the cavity or organ or other site of placement by making the depot too large in cross-section to pass through the opening through which it was introduced. In addition, the open spaces within said coil or helix provides a route for fluid or gas flow, this leaving normal fluid or gas movement undisturbed or minimally disturbed. Thus, the depot may be used to deliver a therapeutic agent to the cavity or organ or other site where it is deposited or to downstream tissues where depot-contacting fluid or gas carries the therapeutic agent released from the depot.

The materials described herein may be used to deliver drugs or other therapeutic agents (e.g., imaging agents or markers) to eyes or tissues nearby. Some of the disease states are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other conditions are further discussed elsewhere herein.

Examples of downstream delivery are deposition of the depot into a ventricle of the brain for delivery of therapeutic agents to the cerebrospinal fluid (CSF), which would distribute the therapeutic agent to brain and spinal tissues without impeding CSF circulation. Another example is deposition into the bronchial system in the lung for distribution of therapeutic to distal lung tissues without blocking air circulation. Another example is placement in, at, or near the renal artery to deliver the therapeutic agent to the kidney without impeding blood flow. Another example would be placement in the stomach for delivery to the stomach or to intestinal sites. Other examples are: in a bladder for delivery to the inside of the bladder and/or ureter, with the material changing shape after placement in the bladder; in a sinus for delivery and distribution through nasal/sinus areas by flow of mucus.

Precursor Materials

The materials for the vehicle may be organogel, hydrogels, or xerogels, which, when exposed to aqueous solution, are hydrogels. Hydrogels are made in aqueous solution and organogels are made in organic solvents. Xerogels are dried organogels or hydrogels. Accordingly, hydrogels and organogels are made by processes that have many similarities. Hydrogels and organogels are made from precursors. Precursors are chosen in consideration of the properties that are desired for the resultant organogel or hydrogel. There are various suitable precursors for use in making the same. The term precursor refers to those molecules crosslinked to form the hydrogel or organogel matrix. While other materials might be present in the hydrogel, such as therapeutic agents or fillers, they are not precursors. The term matrix is applicable for organogels, xerogels, and hydrogels. Such matrices include matrices hydratable to have a water content of more than about 20% w/w; Artisans will immediately appreciate that all ranges and values between the explicitly stated bounds are contemplated, with any of the following being available as an upper or lower limit: 20%, 99%, 80%, 95%, at least 50%, and so forth, with the percentages being w/w and the solvent being water for hydrogels. The matrices may be formed by crosslinking water soluble molecules to form networks of essentially infinite molecular weight. Hydrogels with high water contents are typically soft, pliable materials. Hydrogels and drug delivery systems as described in U.S. Publication Nos. 2009/0017097, 2011/0142936 and 2012/0071865 may be adapted for use with the materials and methods herein by following the guidance provided herein; these references are hereby incorporated herein by reference for all purposes and in case of conflict, the instant specification is controlling.

The matrices may be formed from natural, synthetic, or biosynthetic polymers. Natural polymers may include glycosminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof. In general, the glycosaminoglycans are extracted from a natural source and purified and derivatized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum crosslinked with a polyol such as propylene glycol, and the like, also form hydrogels upon contact with aqueous surroundings.

The matrices may be biostable or biodegradable. Examples of biostable hydrophilic polymeric materials are poly(hydroxyalkyl methacrylate), poly(electrolyte complexes), poly(vinylacetate) cross-linked with hydrolysable or otherwise degradable bonds, and water-swellable N-vinyl lactams. Other hydrogels include hydrophilic hydrogels known as CARBOPOL®, an acidic carboxy polymer (Carbomer resins are high molecular weight, allylpentaerythritol-crosslinked, acrylic acid-based polymers, modified with C10-C30 alkyl acrylates), polyacrylamides, polyacrylic acid, starch graft copolymers, acrylate polymer, ester cross-linked polyglucan. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No. 4,207,893 to Michaels, all of which are incorporated herein by reference, with the present specification controlling in case of conflict.

The matrices may be made from precursors. The precursors are crosslinked with each other. Crosslinks can be formed by covalent bonds or physical bonds. Examples of physical bonds are ionic bonds, hydrophobic association of precursor molecule segments, and crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form matrices and/or polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein. Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule. Some precursors react by a step growth mechanism, and are polymers formed by the stepwise reaction between functional groups of monomers. Most step growth polymers are also classified as condensation polymers, but not all step growth polymers release condensates. Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons. The precursors may thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which is hereby incorporated by reference herein in its entirety to the extent it does not contradict what is explicitly disclosed herein.

To form covalently crosslinked matrices, the precursors must be covalently crosslinked together. In general, polymeric precursors are polymers that will be joined to other polymeric precursors at two or more points, with each point being a linkage to the same or different polymers. Precursors with at least two reactive centers (for example, in free radical polymerization) can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. A hydrophilic molecule, e.g., a precursor or precursor portion, has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic. As is customary in these arts, the term PEG is used to refer to PEO with or without hydroxyl end groups.

A precursor may also be a macromolecule (or macromer), which is a molecule having a molecular weight in the range of a thousand to many millions. The hydrogel may be made with at least one of the precursors as a small molecule of about 1000 Da or less (alternatively: 2000 Da or less). The macromolecule, when reacted in combination with a small molecule (of about 1000 Da or less/200 Da or less), is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000. There are certain advantage to having a small molecule, such as diffusivity for completion of reactions.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic precursors are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Alternatively, natural proteins or polysaccharides may be adapted for use with these methods, e.g., collagens, fibrin (ogen)s, albumins, alginates, hyaluronic acid, and heparins. These natural molecules may further include chemical derivitization, e.g., synthetic polymer decorations. The natural molecule may be crosslinked via its native nucleophiles or after it is derivatized with functional groups, e.g., as in U.S. Pat. Nos. 5,304,595, 5,324,775, 6,371,975, and 7,129,210, each of which is hereby incorporated by reference to the extent it does not contradict what is explicitly disclosed herein. Natural refers to a molecule found in nature. Natural polymers, for example proteins or glycosaminoglycans, e.g., collagen, fibrinogen, albumin, and fibrin, may be crosslinked using reactive precursor species with electrophilic functional groups. Natural polymers normally found in the body are proteolytically degraded by proteases present in the body. Such polymers may be reacted via functional groups such as amines, thiols, or carboxyls on their amino acids or derivatized to have activatable functional groups. While natural polymers may be used in hydrogels, their time to gelation and ultimate mechanical properties must be controlled by appropriate introduction of additional functional groups and selection of suitable reaction conditions, e.g., pH.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TETRONIC. A hydrophobic molecule or a hydrophobic portion of a copolymer or the like is one that is sufficiently hydrophobic to cause the molecule (e.g., polymer or copolymer) to aggregate to form micelles or microphases involving the hydrophobic domains in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade. Embodiments of the invention include choosing a low-solubility agent and choosing a precursor that comprises hydrophobic and hydrophilic portions. The hydrophobic/hydrophilic precursor may comprise one or more functional groups: nucleophiles or electrophiles. The hydrophilic portion, the hydrophobic portion, or both, may be chosen to receive such functional groups. Examples of such agents are, in general, TKIs. Low-solubility means no more than 200 μg/ml soluble in water, the water being pure water, and the drug being essentially pure or a salt. Artisans will immediately appreciate that all ranges and values between the explicitly stated bounds are contemplated, with any of the following being available as an upper or lower limit: 200, 150, 100, 50, 25, 20, e.g., less than 100 or less than 50 μg/ml soluble in water.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

The matrices can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content.

Precursors may be dendrimers, e.g., as in U.S. Publication Nos. 2004/0086479 and 2004/0131582 and PCT Publication Nos. WO07005249, WO07001926 and WO06031358, or the U.S. counterparts thereof; dendrimers may also be useful as multifunctional precursors, e.g., as in U.S. Publication Nos. 2004/0131582 and 2004/0086479 and PCT Publication No. WO06031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, non-fibrin, non-fibrinogen, and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some matrices are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group. Molecular weights are abbreviated in thousands using the symbol k, e.g., with 15K meaning 15,000 molecular weight, i.e., 15,000 Daltons. NH2 refers to an amine termination. SG refers to succinimidyl glutarate. SS refers to succinimidyl succinate. SAP refers to succinimidyl adipate. SAZ refers to succinimidyl azelate. SS, SG, SAP and SAZ are succinimidyl esters that have an ester group that degrades by hydrolysis in water. Hydrolytically degradable or water-degradable thus refers to a material that would spontaneously degrade in vitro in an excess of water without any enzymes or cells present to mediate the degradation. A time for degradation refers to effective disappearance of the material as judged by the naked eye. Trilysine (also abbreviated LLL) is a synthetic tripeptide. PEG and/or hydrogels, as well as compositions that comprise the same, may be provided in a form that is pharmaceutically acceptable, meaning that it is highly purified and free of contaminants, e.g., pyrogens.

Hydrogel Structures

The hydrogel's structure and the material composition of the hydrogel's precursors determine its properties. Precursor factors include properties such as biocompatibility, water solubility, hydrophilicity, molecular weight, arm length, number of arms, functional groups, distance between crosslinks, degradability, and the like. The choice of reaction conditions (as a hydrogel or organogel, choice of buffers, pH, precursors, and so forth) also effects the hydrogel's structure and properties, including choices of solvents, reaction schemes, reactant concentrations, solids content, and the like. There can be a variety of ways to achieve certain properties, or combination of properties. On the other hand some properties are in tension with each other, for instance brittleness may increase as a distance between crosslinks or solids content increases. Strength may be increased by increasing the number of crosslinks but swelling may thereby be reduced. Artisans will appreciate that the same materials may be used to make matrices with a great range of structures that will have highly distinct mechanical properties and performance, such that the achievement of a particular property should not be merely assumed based on the general types of precursors that are involved.

The spacing between molecular strands of the hydrogel (the matrix) affects several hydrogel properties, including a rate of diffusion of molecules. The crosslinking density can be controlled by the choice of the overall molecular weight of the precursor(s) used as crosslinker(s) and other precursor(s) and the number of functional groups available per precursor molecule. A lower molecular weight between crosslinks such as 200 will give much higher crosslinking density as compared to a higher molecular weight between crosslinks such as 500,000; artisans will immediately appreciate that all ranges and values within this range are contemplated and supported, e.g., 200 to 250,000, 500 to 400,000, 5,000, 10,000, 20,000, 30,000, 40,000, 50,000, 60,000, 70,000, 80,000, 90,000, 100,000, and so forth. The crosslinking density also may be controlled by the overall percent solids of the crosslinker and functional polymer solutions. Yet another method to control crosslink density is by adjusting the stoichiometry of nucleophilic functional groups to electrophilic functional groups. A one to one ratio leads to the highest crosslink density. Precursors with longer distances between crosslinkable sites form gels that are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 2,000 to 100,000; artisans will immediately appreciate that all the ranges and values within the explicitly stated ranges are contemplated, e.g. 5,000 to 35,000. The solids content of the hydrogel can affect its mechanical properties and biocompatibility and reflects a balance between competing requirements. A relatively low solids content is useful, e.g., between about 2.5% to about 20%, including all ranges and values there between, e.g., about 2.5% to about 10%, about 5% to about 15%, or less than about 15%.

Reaction kinetics are generally controlled in light of the particular functional groups unless an external initiator or chain transfer agent is required, in which case triggering the initiator or manipulating the transfer agent can be a controlling step. In some embodiments, the molecular weights of the precursors are used to affect reaction times. Precursors with lower molecular weights tend to speed the reaction, so that some embodiments have at least one precursor with a molecular weight of at least 5,000 to 50,000 or 150,000 Daltons. Preferably the crosslinking reaction leading to gelation occurs within about 2 to about 10 or to about 30 minutes; artisans will immediately appreciate that all the ranges and values within the explicitly stated ranges are contemplated, e.g., at least 120 seconds, or between 180 to 600 seconds. Gelation time is measured by applying the precursors to a flat surface and determining the time at which there is substantially no flow down the surface when it is titled at an angle of about 60 degrees (i.e., a steep angle, close to perpendicular).

The matrices may be low-swelling, as measurable by the hydrogel having a weight increasing no more than about 0% to about 10% or to about 50% upon exposure to a physiological solution for twenty-four hours relative to a weight of the hydrogel at the time of formation. One embodiment for reducing swelling is to increase the number of crosslinks, bearing in mind, however, that crosslinks can increase rigidity or brittleness. Another embodiment is to reduce the average chain distance between crosslinks. Another embodiment is to use precursors with many arms, as explained below. Another embodiment to reduce swelling is to control the degree of hydrophilicity, with less hydrophilic materials tending to swell less; for instance, highly hydrophilic materials such as PEOs can be combined with less hydrophilic materials such as PPO or even hydrophobic groups such as alkyls.

Another embodiment to reduce or control swelling is to choose precursors that have a high degree of solvation at the time of crosslinking but subsequently become less solvated and having a radius of solvation that effectively shrinks; in other words, the precursor is spread-out in solution when crosslinked but later contracts. Changes to pH, temperature, solids concentration, and solvent environment can cause such changes; moreover, an increase in the number of branches (with other factors being held effectively constant) will tend to also have this effect. The number of arms are believed to sterically hinder each other so that they spread-out before crosslinking, but these steric effects are offset by other factors after polymerization. In some embodiments, precursors have a plurality of similar charges so as to achieve these effects, e.g., a plurality of functional groups having a negative charge, or a plurality of arms each having a positive charge, or each arm having a functional group of similar charges before crosslinking or other reaction.

Hydrogels described herein can include hydrogels that swell minimally after deposition. Such medical low-swellable hydrogels may have a weight upon polymerization that increases no more than, e.g., about 50%, about 10%, about 5%, about 0% by weight upon exposure to a physiological solution, or that shrink (decrease in weight and volume), e.g., by at least about 5%, at least about 10%, or more. Artisans will immediately appreciate that all ranges and values within or otherwise relating to these explicitly articulated limits are disclosed herein. Unless otherwise indicated, swelling of a hydrogel relates to its change in volume (or weight) between the time of its formation when crosslinking is effectively complete and the time after being placed in vitro a physiological solution in an unconstrained state for twenty-four hours, at which point it may be reasonably assumed to have achieved its equilibrium swelling state. % swelling=[(Weight at equilibrium swelling−Weight at initial formation)/Weight at initial formation]*100. The weight of the hydrogel includes the weight of the solution in the hydrogel.

Functional Groups

The precursors for covalent crosslinking have functional groups that react with each other to form the material via covalent bonds, either outside a patient, or in situ. The functional groups generally are polymerizable, a broad category that encompasses free radical, addition, and condensation polymerization and also groups for electrophile-nucleophile reactions. Various aspects of polymerization reactions are discussed in the precursors section herein.

Thus in some embodiments, precursors have a polymerizable group that is activated by photoinitiation or redox systems as used in the polymerization arts, or electrophilic functional groups, for instance: carbodiimidazole, sulfonyl chloride, chlorocarbonates, N-hydroxysuccinimidyl ester, succinimidyl ester or sulfasuccinimidyl esters, or as in U.S. Pat. Nos. 5,410,016 or 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7). Buffers may also be included in the hydrogels introduced into a body.

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di- or multifunctional poly(ethylene glycol) can be used.

One embodiment has reactive precursor species with 2 to 16 nucleophilic functional groups each and reactive precursor species with 2 to 16 electrophilic functional groups each; artisans will immediately appreciate that all the ranges and values within the explicitly stated ranges are contemplated, for instance 2, 3, 4, 5, 6, 7, 8, 9, 10, 11, 12, 13, 14, 15, or 16 groups.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1, 4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Initiating Systems

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2, 2-dimethoxy-2-phenyl acetophenone groups, other acetophenone derivatives, thioxanthone groups, benzophenone groups, and camphorquinone groups. Examples of thermally reactive initiators include 4, 4' azobis (4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Visualization Agents

A visualization agent may be used in a xerogel/organogel/hydrogel; it reflects or emits light at a wavelength detectable to a human eye so that a user applying the hydrogel could observe the object when it contains an effective amount of the agent. Agents that require a machine aid for imaging are referred to as imaging agents herein, and examples include: radioopaque contrast agents and ultrasound contrast agents.

Some biocompatible visualization agents are FD&C BLUE #1, FD&C BLUE #2, and methylene blue. These agents, if used, are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. Visualization agents may be covalently linked to the molecular network of the xerogel/hydrogel, thus preserving visualization after application to a patient until the hydrogel hydrolyzes to dissolution. Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. Reactive visualization agents such as NHS-fluorescein can be used to incorporate the visualization agent into the molecular network of the xerogel/hydrogel. The visualization agent may be present with either reactive precursor species, e.g., a crosslinker or functional polymer solution. The preferred colored substance may or may not become chemically bound to the hydrogel.

Biodegradation

An hydrogel may be formed so that, upon hydration in physiological solution, a hydrogel is formed that is water-degradable, as measurable by the hydrogel losing its mechanical strength and eventually dissipating in vitro in an excess of water by hydrolytic degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in tissues. The hydrogels, however, may exclude such materials, and may be free of polyanhydrides, anhydride bonds, and/or free of precursors that degrade into acid or diacids, and/or free of PLA, PLGA, PLA/PLGA.

For example, electrophilic groups such as SG (N-hydroxysuccinimidyl glutarate), SS (N-hydroxysuccinimidyl succinate), SC (N-hydroxysuccinimidyl carbonate), SAP (N-hydroxysuccinimidyl adipate) or SAZ (N-hydroxysuccinimidyl azelate) may be used and have esteric linkages that are hydrolytically labile. More linear hydrophobic linkages such as pimelate, suberate, azelate or sebacate linkages may also be used, with these linkages being less degradable than succinate, glutarate or adipate linkages. Branched, cyclic or other hydrophobic linkages may also be used. Polyethylene glycols and other precursors may be prepared with these groups. The crosslinked hydrogel degradation may proceed by the water-driven hydrolysis of the biodegradable segment when water-degradable materials are used. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment. If polyglycolate is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to many months, using a degradable segment. Some embodiments include precursors that are free of adjacent ester groups and/or have no more than one ester group per arm on one or more of the precursors: control of the number and position of the esters can assist in uniform degradation of the hydrogel.

A biodegradable linkage in the organogel and/or xerogel and/or hydrogel and/or precursor may be water-degradable or enzymatically degradable. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

If it is desired that a biocompatible crosslinked matrix be biodegradable or absorbable, one or more precursors having biodegradable linkages (or just one biodegradable linkage, for example an ester) present in between the functional groups may be used. The biodegradable linkage optionally also may serve as the water soluble core of one or more of the precursors used to make the matrix. For each approach, biodegradable linkages may be chosen such that the resulting biodegradable biocompatible crosslinked polymer will degrade or be absorbed in a desired period of time.

Bipolymeric vehicles may be chosen with hydrogels having different rates of degradation. The materials have a plurality of hydrogels in layers, e.g., one or more inner hydrogels with a layer of an outer hydrogel on them. For instance, one or more rods arranged in parallel or as strands (twisted, braided) inside a hydrogel layer. The various hydrogels may be chosen to have different degradation rates. Degradation of an interior hydrogel can be advantageous to accelerate relative to another inner hydrogel or outer hydrogel to provide for a greater surface area of the drug, provided, however, that its degradation does not cause the other layer to lose a curved shape that is desired to avoid harm to sensitive tissues. Delay of degradaton of an inner hydrogel relative to other hydrogels can be advantageous to maintain a curved shape, e.g., to keep an intraocular vehicle coiled or in a compact shape, until some or all of the other layers degrade. Accordingly one of, or a plurality of, inner hydrogels can be independently chosen to have a degradation that is greater than, or less than, other hydrogels and/or an outermost hydrogel layer. Thus one or more differential degradation rates may provide for the vehicle to maintain an initial shape (e.g., coil shape) for a period of time between 1-365 days (all ranges contemplated: 1, 2, 7, 14, 21, 30 days, 1, 2, 3, 4, 5, 6, 7, 8, 9, 10, 11, 12 months). This property provides for the shape to be maintained until advanced stages of the degradation process. And the differential degradation rates may be used to determine the ability to unfurl the coil or other compact shape at particular stages of the degradation process. Moreover, in the case wherein multiple hydrogels/rods/strands are surrounded by a second material, they may be independently selected to have a range coefficients of elongation or swelling such that complex shape changes upon exposure to physiological fluid can be engineered. The various rates may be controlled by hydrolytic and/or enzymatic degradation times to control shape changes during the degradation process.

Drugs or Other Therapeutic Agents for Delivery

Therapeutic agents are known for many purposes. These include, for example, agents for treating conditions that may result from inflammatory or abnormal vascular conditions, retinal vein occlusion, geographic atrophy, retinitis pigmentosa, retinoblastoma, etc. For cancer, agents may be, e.g., anti-cancer drugs, anti-VEGFs, or drugs known for use in cancer treatment.

Therapeutic agents may be those that are, e.g., antiangiogenic, anti-VEGF, anti-VEGF protein, anti-VEGF aptamer, anti-VEGF antibody, anti-VEGF antibody fragment, anti-VEGF single chain antibody fragment, blocks VEGFR1, blocks VEGFR2, blocks VEGFR3, anti-PDGF, anti-PDGF protein, anti-PDGF aptamer, anti-PDGF antibody, anti-PDGF antibody fragment, anti-PDGF single chain antibody fragment, anti-ang2, anti-ang2 protein, anti-ang2 aptamer, anti-ang2 antibody, anti-ang2 antibody fragment, anti-ang2 single chain antibody fragment, anti-angiogenesis, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinib (GLEEVAC) gefinitib (IRESSA), toceranib (PALLADIA), Erlotinib (TARCEVA), Lapatinib (TYKERB) Nilotinib, Bosutinib Neratinib, lapatinib, Vatalanib, dasatinib, erlotinib, gefitinib, imatinib, lapatinib, lestaurtinib, nilotinib, semaxanib, toceranib, vandetanib.

The therapeutic agent may comprise a macromolecule, for example an antibody, single chain antibody fragment, or other antibody fragment. The therapeutic macromolecule may comprise a VEGF inhibitor, for example ranibizumab, the active ingredient in the commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ (ranibizumab), Avastin™ (bevacizumab), Macugen™ (pegaptanib). Platelet derived growth factor (PDGF) inhibitors may also be delivered, e.g. Fovista™, an anti-PGDF aptamer.

The therapeutic agent may comprise small molecules such as of a steroid or corticosteroid and analogues thereof. For example, the therapeutic corticosteroid may comprise one or more of trimacinalone, trimacinalone acetonide, dexamethasone, dexamethasone acetate, fluocinolone, fluocinolone acetate, loteprednol etabonate, or analogues thereof. Alternatively or in combination, the small molecules of therapeutic agent may comprise a tyrosine kinase inhibitor.

The therapeutic agent may comprise an antiangiogenic or anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™), sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™ Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; Regeneron™ (VEGF Trap) or complement inhibitor (POT-4).

The therapeutic agent may comprise a kinase inhibitor such as one or more of bevacizumab (monoclonal antibody), BIBW 2992 (small molecule targeting EGFR/Erb2), cetuximab (monoclonal antibody), imatinib (small molecule), trastuzumab (monoclonal antibody), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/VEGFR2, small molecule commercially available from Esai, Co.)

Therapeutic agents may include various classes of drugs. Drugs include, for instance, steroids, non-steroidal anti-inflammatory drugs (NSAIDS), anti-cancer drugs, antibiotics, an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). Therapeutic agents include classes of drugs including steroids, NSAIDS, antibiotics, pain relievers, inhibitors of vascular endothelial growth factor (VEGF), chemotherapeutics, antiviral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

Therapeutic agents may include a protein or other water soluble biologics. These include peptides and proteins. The term peptide, as used herein, refers to peptides of any size, e.g., at least 1000 Da molecular weight, or from 100-200,000 molecular weight; Artisans will immediately appreciate that all ranges and values between the explicitly stated bounds are contemplated, with, e.g., any of the following being available as an upper or lower limit: 100, 200, 300, 400, 500, 1000, 5,000, 10,000, 20,000, 30,000, 40,000, 50,000, 60,000, 80,000, 100,000, 150,000, 200,000. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers.

The therapeutic agents may be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure—open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure—open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of therapeutic agents for delivery include those that specifically bind a target peptide in vivo to prevent the interaction of the target peptide with its natural receptor or other ligands. AVASTIN, for instance, is an antibody that binds VEGF. Also known are fusion proteins that include at least a portion of a VEGF receptor to trap VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non-specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Oxifloxacin is the active ingredient in VIGAMOX, which is a fluoroquinolone approved for use to treat or prevent ophthalmic bacterial infections. Dosage is typically one-drop of a 0.5% solution that is administered 3 times a day for a period of one-week or more. VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis. Permeation agents are agents and may also be included in a gel, hydrogel, organogel, xerogel, and biomaterials as described herein. These are agents that assist in permeation of a drug into an intended tissue. Permeation agents may be chosen as needed for the tissue, e.g., permeation agents for skin, permeation agents for an eardrum, and permeation agents for an eye.

Controlled Release

TKIs, proteins, and other agents may be controllably released. A first technique is to use a hydrogel to control a rate of release, with the agent being entrapped in the hydrogel until the hydrogel erodes. A second technique puts the agent in a particle that controls the rate of release. The particle has to erode to release the agent, or it is made of a material that limits diffusion of the agent from the particle, or the particle comprises a release rate agent, with the agent being chosen to slow-down release of the agent from the particle. A third technique uses a solid agent or concentrated liquid agent that is inside a hydrogel; the hydrogel matrix can be made to limit diffusion of fluid so that the agent is slow to enter solution because the turn-over of fluid next to the agent is slow. A fourth technique uses a hydrogel as rate limiting barrier to control a rate of release; the hydrogel allows diffusion of the agent out of the hydrogel without necessarily having to be eroded for release to take place. These and other techniques may be applied to controllably release an agent. The size and solubility of the agent, its charge, melting point, hydrophobicity or hydrophilicity, and other physical characteristics can affect the choice of techniques. The techniques can be used together, for instance, a hydrogel that limits a rate of diffusion in combination with particles that control release.

Embodiments include agents that are particles, or are in particles, that have a maximum dimension of 0.01 to 100 microns; Artisans will immediately appreciate that all ranges and values between the explicitly stated bounds are contemplated, with, e.g., any of the following being available as an upper or lower limit: 0.01. 0.02. 0.05. 0.1, 0.5, 0.6, 1, 2, 4, 5, 6, 7, 8, 9, 10, 20, 50, 80, 90, 100 microns. The term particle is broad and encompasses spheres, drops, whiskers, and irregular shapes. Particles include powders or drops of agents that are insoluble in aqueous solution or that have a low water solubility, meaning a water solubility in the range of about 0.001 to about 0.5 mg/ml at 20° C. Agents that are micronized, as per the example with Axitinib herein, are useful in many situations. The particles, in some embodiments, are made with low water soluble lipophilic materials that have a molecular weight of no more than about 2000. An embodiment of the system involves a hydrophilic hydrogel comprising dispersed lipophilic particles that contain a therapeutic agent. The particles may be made with molecules that hydrophobic and/or hydrophilic agents may be used.

Certain embodiments of the invention are accomplished by providing compositions and methods to control the release of relatively low molecular weight therapeutic species using hydrogels. A therapeutic agent first is dispersed or dissolved within one or more relatively hydrophobic rate modifying agents to form a mixture. The mixture may be formed into particles or microparticles, which are then entrapped within a bioabsorbable hydrogel matrix so as to release the water soluble therapeutic agents in a controlled fashion. Alternatively, the microparticles may be formed in situ during crosslinking of the hydrogel.

In another method, hydrogel microspheres are formed from polymerizable macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Pre-formed microparticles containing the water soluble therapeutic agent may be dispersed in the polymerizable phase, or formed in situ, to form an emulsion. Polymerization and crosslinking of the emulsion and the immiscible phase is initiated in a controlled fashion after dispersal of the polymerizable phase into appropriately sized microspheres, thus entrapping the microparticles in the hydrogel microspheres. Visualization agents may be included, for instance, in the microspheres, microparticles, and/or microdroplets.

Embodiments of the invention include compositions and methods for forming composite hydrogel-based matrices and microspheres having entrapped therapeutic compounds. In one embodiment, a bioactive agent is entrapped in microparticles having a hydrophobic nature (also termed hydrophobic microdomains), to retard leakage of the entrapped agent. In some cases, the composite materials that have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase). The oil phase entraps the drug and provides a barrier to release by slow partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent. Visualization agents may be included, for instance, in the gel matrix or the microdomains.

In one embodiment, a microemulsion of a hydrophobic phase and an aqueous solution of a water soluble molecular compound, such as a protein, peptide or other water soluble chemical is prepared. The emulsion is of the "water-in-oil" type (with oil as the continuous phase) as opposed to an "oil-in-water" system (where water is the continuous phase). Other aspects of drug delivery are found in U.S. Pat. Nos. 6,632,457; 6,379,373; and 6,514,534, each of which are hereby incorporated by reference.

Controlled rates of drug delivery also may be obtained by degradable, covalent attachment of the agents to the crosslinked hydrogel network. The nature of the covalent attachment can be controlled to enable control of the release rate from hours to weeks or years. By using a composite made from linkages with a range of hydrolysis times, a controlled release profile may be extended for longer durations. Polymers that include ester linkages may also be included to provide a desired degradation rate of a hydrogel, of a particle, or an attachment linkage, with groups being added or subtracted near the esters to increase or decrease the rate of degradation. Thus it is possible to construct a hydrogel with a desired degradation profile, from a few days to many months, using a degradable segment. If polyglycolate is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to many months, using a degradable segment.

Embodiments of the invention include a prosthesis that controllably releases an amount of an agent over a period of time from 1 day to 5 years; Artisans will immediately appreciate that all ranges and values between the explicitly stated bounds are contemplated, with, e.g., any of the following being available as an upper or lower limit: 1, 2, 3, 4, 5, 6, 7, 8, 9, 10, 11, 12, 13, 14, 15, 16, 17, 18, 19, 20, 21, 22, 23, 24 months, 1, 1.5, 2, 2.5, 3, 3.5, 4. 4, 5, 5 years. The amount of the agent released in the period of time may vary from, e.g., 10% to 100% w/w; Artisans will immediately appreciate that all ranges and values between the explicitly stated bounds are contemplated, with, e.g., any of the following being available as an upper or lower limit: 10, 20, 30, 40, 50, 60, 70 80, 90, 95, 99, 100 percent w/w of the agent is released. For example, applying these values, a plot of a cumulative release of an agent versus tine may be used to show a release of 50% or 80% w/w of an agent is reached at a time that falls within 1-24 months: e.g., 1, 2, 3, 4, 5, 6, 7, 8, 9, 10, 11, 12, 13, 14, 15, 16, 17, 18, 19, 20, 21, 22, 23, 24 months. During the time of release, the released concentration may be provided to a tissue, e.g., an eye or a retina, in an effective amount, meaning at least the IC50 of effectiveness (inhibition for an inhibiting agent, activating for an activating agent).

Kits or Systems

Kits may be made that comprise one or more components set forth herein. For instance, the kit may have an applicator and a shape-changing vehicle. The kits are manufactured using medically acceptable conditions and contain components that have sterility, purity and preparation that is pharmaceutically acceptable. Solvents/solutions or diluents may be provided in the kit or separately. The kit may include syringes and/or needles for mixing and/or delivery. Instructions for carrying out one or methods set forth herein may be provided.

EXAMPLES

Some precursors are referred to by a nomenclature of naxxKpppfff, where n is the number of arms, xx is the molecular weight (MW), ppp is the polymer, and fff is the functional end group. Thus 8a15KPEGSAP refers to an 8-armed Polyethylene glycol (PEG) with a MW of 15,000 g/mol=15K PEG. Succinimidyl adipate is: SAP. Succinimidyl glutarate is SG.

Examples—Coiling Bi-Polymeric Fibers

Example 1—Coiling Hydrogel Bi-Polymeric Fiber

Fiber Formation:
Buffer 1: Sodium phosphate dibasic (240 mg) was dissolved in deionized (DI) water and made up to 10 mL (24 mg/mL).
Buffer 2: Sodium phosphate monobasic (462.4 mg) was dissolved in deionized (DI) water and made up to 50 mL (9.25 mg/mL).
Syringe 1: Polyethylene glycol (PEG), MW=20 kDa, 4 arms (initiated with pentaerythritol), each arm end-capped with succimimidyl glutarate (4a20 k PEG SG, 16.7 mg) was weighed into a 1 mL, polyethylene (PE) syringe (BD) and dissolved in 108.4 mg of Buffer 2.
Syringe 2: Polyethylene glycol (PEG), MW=20 kDa, 8 arms (initiated with hexaglycerol), each arm end-capped with amine (8a20 k PEG $NH_2$, 8.3 mg) was weighed into a 1 mL, PE syringe (BD) and dissolved in 116.7 mg of Buffer 1.

The contents of syringe 1 and syringe 2 were mixed and injected into four segments of silicone tubing, each approximately 25 cm long, having an inner diameter of approximately 0.51 mm (Dow Corning Silastic, catalogue #508-002) using a 21G needle (BD). After gelation was confirmed, each tube was then transferred into a 37° C. chamber (Binder Oven, model #ED-115 UL) under a nitrogen sweep to dry for about 9 days.

Each dried strand was gently stretched by manually pulling gently on both ends, causing necking, to form an oriented fiber along its full length. The final draw ratio was about 4 times the original length. The necked fiber was pulled into a length of polyethylene tubing having an inner diameter of approximately 0.58 mm (Intramedic, catalogue #427411) and the tubing was cut to a length approximately 3 cm shorter than the fiber. A 1.5 cm segment remained exposed outside of each end of the tubing, and each end of the taut fiber was taped to the side of a 1 liter glass beaker using laboratory tape. The curvature of the beaker was used to maintain the fiber tight against the inside wall of the tube.
Second Layer:
Syringe 3: 2.5 mg of 8a20 k PEG $NH_2$ was weighed into a 1 mL PE syringe and dissolved in 122.5 mg of the buffer 1 and a trace amount of Lissamine Green B for visualization.
Syringe 4: Polyethylene glycol (PEG), MW=40 kDa, 4 arms (initiated with pentaerythritol), each arm end-capped with succimimidyl adipate (4a20 k PEG SAP, 10 mg) was weighed into a 1 mL PE syringe (BD) and dissolved in 115 mg of Buffer 2.

The contents of the syringes 3 and 4 were mixed and then injected through a 25G BD needle into one end of the polyethylene tubing containing the fiber, filling the lumen to coat the fiber while the fiber was held in tension, and the coating was allowed to gel. After gelation of the coating, the sample, still attached to the beaker, was transferred into the 37° C. chamber (Binder Oven, model #ED-115 UL) under a nitrogen sweep, where it remained for approximately 3.5 days. The tubing was cut to approximately 1cm segments and the fiber carefully removed from each segment. The diameter of coated fiber measured between 0.12 mm to 0.14 mm.
Hydration and Coiling in PBS and HA/PBS Solutions:
A small amount of phosphate buffered saline (PBS) solution was heated to approximately 37° C. in a plastic weigh boat on a hot plate. A coated fiber segment was then placed in a second weigh boat. Using a 3 mL transfer pipette, a few droplets of the PBS were added to the fiber. The fiber rapidly retracted into a uniform helical coil in less than 15 seconds. This hydration was video recorded and digitally photographed, see FIGS. 10A-10C.

A small plastic weigh boat was placed on a hot plate, and several droplets of 2.0% sodium hyaluronate (MW=850 KDa) (HA) solution in PBS were added to the weigh boat. The viscosity of the HA/PBS solution was intended to simulate rabbit vitreous humor. The solution was heated to approximately 37° C. A coated fiber segment was placed into this viscous solution at 37° C., and again coiled in less than 15 seconds into a uniform helical shape, indicating the increase in viscosity did not significantly retard the coil formation. This hydration was video recorded and digitally photographed, see FIGS. 11A-11C.

Example 2—Fluorescein Conjugated Hydrogel Bi-Polymeric Coil Examples

Two additional hydrogel formulations were used to create coiling bi-polymeric fibers.
Buffer 1: Sodium phosphate monobasic (904.4 mg) was dissolved in deionized (DI) water and made up to 100 mL (9 mg/mL).
Buffer 2: Sodium phosphate dibasic (2.4301 g) was dissolved in deionized (DI) water and made up to 100 mL (24.3 mg/mL).
Amine Solution: Polyethylene glycol (PEG), MW=20 kDa, 8 arms (initiated with hexaglycerol), each arm end-capped with amine (8a20 k PEG $NH_2$, 715.9 mg) and NHS-Fluorescein (15.0 mg) were dissolved in Buffer 2 and made up to 10 mL. Resulting solution was held overnight, with the vessel wrapped in foil to minimize light exposure.

Example 2A

Fiber Formation:
Syringe 1A: Polyethylene glycol (PEG), MW=20 kDa, 4 arms (initiated with pentaerythritol), each arm end-capped with succinimidyl glutarate (4a20 k PEG SG, 166.2 mg) was dissolved in 1.157 mL of Buffer 1. Transferred resulting solution (125 µL) into a 1 mL polyethylene (PE) syringe (BD).
Syringe 2A: Amine solution was transferred (125 µL) into a 1 mL PE syringe (BD).
The contents of Syringe 1A and Syringe 2A were mixed and injected into four segments of Dow Corning Silastic silicone tubing (cat. #508-002), each approximately 25 cm long, having an inner diameter of approximately 0.51 mm using a 21G needle. After gelation was confirmed, each tube was then transferred into a 37° C. chamber (Binder Oven, model #ED-115 UL) under a nitrogen sweep to dry for about 3 days.

The dried strand was gently stretched by manually pulling gently on both ends, causing necking, to form an oriented fiber along its full length. The final draw ratio was about 4 times the original length. The necked fiber was pulled into a length of polyethylene tubing (cat. #427411) having an inner diameter of approximately 0.58 mm and the tubing was cut to a length approximately 3 cm shorter than the fiber. A 1.5 cm segment remained exposed outside of each end of the tubing, and each end of the taut fiber was taped to the side of an aluminum weigh boat using laboratory tape. The curvature of the weigh boat was used to maintain the fiber tight against the inside wall of the tube.

Second Layer:

Syringe 3A: Polyethylene glycol (PEG), MW=40 kDa, 4 arms (initiated with pentaerythritol), each arm end-capped with succinimidyl adipate (4a40 k PEG SAP, 101.3 mg) was dissolved in 1.15 mL of Buffer 1. Resulting solution was transferred (125 µL) into a 1 mL polyethylene (PE) syringe (BD).

Syringe 4A: The Amine Solution (5 mL) was diluted using Buffer 2 and made up to 10 mL. Resulting solution was transferred (125 µL) into a 1 mL PE syringe (BD).

The contents of the syringes 3A and 4A were mixed and injected into one end of the polyethylene tubing containing the fiber, filling the lumen to coat the fiber while the fiber was held in tension, and the coating was allowed to gel. After gelation of the coating, the sample, still attached to the weigh boat, was transferred into the 37° C. chamber under a nitrogen sweep, where it remained for approximately 7 days.

After drying, the coated strand was cut away from the weigh boat. The polyethylene tubing was cut into segments approximately 12 mm in length, and the resulting segments of coated fibers were removed from the tubing. The coated fiber segments were placed in a vial and capped for storage.

Example 2B

Syringe 1B: Polyethylene glycol (PEG), MW=20 kDa, 4 arms (initiated with pentaerythritol), each arm end-capped with succinimidyl adipate (4a20 k PEG SAP, 1.774 mg) was dissolved in 1.157 mL of Buffer 1. Transferred resulting solution (125 µL) into a 1 mL polyethylene (PE) syringe (BD).

Syringe 2B: Amine solution was transferred (125 µL) into a 1 mL PE syringe (BD).

The contents of Syringe 1B and Syringe 2B were mixed and injected into four segments of silicone tubing, each approximately 25 cm long, having an inner diameter of approximately 0.51 mm using a 21G needle. After gelation was confirmed, each tube was then transferred into a 37° C. chamber under a nitrogen sweep to dry for about 3 days.

The dried strand was gently stretched by manually pulling gently on both ends, causing necking, to form an oriented fiber along its full length. The final draw ratio was about 4 times the original length. The necked fiber was pulled into a length of polyethylene tubing having an inner diameter of approximately 0.58 mm and the tubing was cut to a length approximately 3 cm shorter than the fiber. A 1.5 cm segment remained exposed outside of each end of the tubing, and each end of the taut fiber was taped to the side of an aluminum weigh boat using laboratory tape. The curvature of the weigh boat was used to maintain the fiber tight against the inside wall of the tube.

Syringe 3B: Weighed 4a40 k PEG SAP (20.1 mg) into a 1 mL PE syringe (BD) and dissolved in 105 µL of Buffer 1.

Syringe 4B: Amine solution was transferred (125 µL) into a 1 mL PE syringe (BD).

The contents of the syringes 3B and 4B were mixed and injected into one end of the polyethylene tubing containing the fiber, filling the lumen to coat the fiber while the fiber was held in tension, and the coating was allowed to gel. After gelation of the coating, the sample, still attached to the weigh boat, was transferred into the 37° C. chamber under a nitrogen sweep, where it remained for approximately 7 days.

After drying, the coated strand was cut away from the weigh boat. The polyethylene tubing was cut into segments approximately 12 mm in length, and the resulting segments of coated fibers were removed from the tubing. The coated fiber segments were placed in a vial and capped for storage.

Example 3—Fluorescein Conjugated Organogel Bi-Polymeric Coil Examples

Example 3A

Fiber Formation:

Syringe 1A: Polyethylene glycol (PEG), MW=20 kDa, 4 arms (initiated with pentaerythritol), each arm end-capped with succinimidyl glutarate (4a20 k PEG SG, 202.4 mg) was dissolved in 1.39 mL Dimethyl Carbonate (DMC) in a 10 mL vial. Vial was immediately stoppered to seal. Resulting solution was transferred (125 µL) into a 1 mL polyethylene (PE) syringe (BD).

Syringe 2A: Polyethylene glycol (PEG), MW=20 kDa, 8 arms (initiated with hexaglycerol), each arm end-capped with amine (8a20 k PEG $NH_2$, 159.7 mg) and NHS-Fluorescein (3.4 mg) were dissolved in DMC (2.08 mL) in a 10 mL vial. Vial was immediately stoppered to seal. Resulting solution was held overnight, then transferred (125 µL) into a 1 mL PE syringe (BD).

The contents of Syringe 1A and Syringe 2A were mixed and injected into four segments of silicone tubing, each approximately 25 cm long, having an inner diameter of approximately 0.51 mm using a 21G needle. After gelation was confirmed, each tube was then transferred into a 37° C. chamber under a nitrogen sweep to dry overnight.

Each dried strand was gently stretched by manually pulling gently on both ends, causing necking, to form an oriented fiber along its full length. The final draw ratio was about 4 times the original length. The necked fiber was pulled into a length of polyethylene tubing having an inner diameter of approximately 0.58 mm and the tubing was cut to a length approximately 3 cm shorter than the fiber. A 1.5 cm segment remained exposed outside of each end of the tubing, and each end of the taut fiber was taped to the side of an aluminum weigh boat using laboratory tape. The curvature of the weigh boat was used to maintain the fiber tight against the inside wall of the tube.

Second Layer:

Syringe 3A: Weighed Polyethylene glycol (PEG), MW=40 kDa, 4 arms (initiated with pentaerythritol), each arm end-capped with succinimidyl adipate (4a40 k PEG SAP, 201.8 mg) and dissolved in 2.3 mL of DMC in a 10 mL vial. Vial was immediately stoppered to seal. Resulting solution was transferred (125 µL) into a 1 mL PE syringe (BD).

Syringe 4A: Transferred same solution as used for Syringe2 (62.5 µL) into a 1 mL PE syringe (BD). Added DMC (62.5 µL) to the syringe to dilute.

The contents of the syringes 3A and 4A were mixed and injected into one end of the polyethylene tubing containing the fiber, filling the lumen to coat the fiber while the fiber was held in tension, and the coating was allowed to gel. After gelation of the coating, the sample, still attached to the weigh boat, was transferred into the 37° C. chamber under a nitrogen sweep, where it remained overnight.

After drying, the coated strand was cut away from the weigh boat. The polyethylene tubing was cut into segments approximately 12 mm in length, and the resulting segments of coated fibers were removed from the tubing. The coated fiber segments were placed in a 10 mL vial and capped for storage. The diameter of the segments was measured to be between 0.16 mm-0.18 mm. An image of the dried fiber is presented in FIG. 13A.

Example 3B

Fiber Formation:

Syringe 1B: Polyethylene glycol (PEG), MW=20 kDa, 4 arms (initiated with pentaerythritol), each arm end-capped with succinimidyl adipate (4a20 k PEG SAP, 203.4 mg) was dissolved in 1.4 mL Dimethyl Carbonate (DMC) in a 10 mL vial. Vial was immediately stoppered to seal. Resulting solution was transferred (125 µL) into a 1 mL polyethylene (PE) syringe (BD).

Syringe 2 B: Polyethylene glycol (PEG), MW=20 kDa, 8 arms (initiated with hexaglycerol), each arm end-capped with amine (8a20 k PEG $NH_2$, 200 mg) and NHS-Fluorescein (4.1 mg) were dissolved in DMC (2.6 mL) in a 10 mL vial. Vial was immediately stoppered to seal. Resulting solution was held overnight, then transferred (125 µL) into a 1 mL PE syringe (BD).

The contents of Syringe 1B and Syringe 2B were mixed and injected into four segments of silicone tubing, each approximately 25 cm long, having an inner diameter of approximately 0.51 mm using a 21G needle. After gelation was confirmed, each tube was then transferred into a 37° C. chamber under a nitrogen sweep to dry overnight.

Each dried strand was gently stretched by manually pulling gently on both ends, causing necking, to form an oriented fiber along its full length. The final draw ratio was about 4 times the original length. The necked fiber was pulled into a length of polyethylene tubing having an inner diameter of approximately 0.58 mm and the tubing was cut to a length approximately 3 cm shorter than the fiber. A 1.5 cm segment remained exposed outside of each end of the tubing, and each end of the taut fiber was taped to the side of an aluminum weigh boat using laboratory tape. The curvature of the weigh boat was used to maintain the fiber tight against the inside wall of the tube.

Second Layer:

Syringe 3B: Transferred same solution used in Syringe 1B (125 µL) into a 1 mL PE syringe (BD).

Syringe 4B: Transferred same solution used in Syringe 2B (125 µL) into a 1 mL PE syringe (BD).

The contents of the syringes 3B and 4B were mixed and injected into one end of the polyethylene tubing containing the fiber, filling the lumen to coat the fiber while the fiber was held in tension, and the coating was allowed to gel. After gelation of the coating, the sample, still attached to the weigh boat, was transferred into the 37° C. chamber under a nitrogen sweep, where it remained overnight.

After drying, the coated strand was cut away from the weigh boat. The polyethylene tubing was cut into segments approximately 12 mm in length, and the resulting segments of coated fibers were removed from the tubing. The coated fiber segments were placed in a 10 mL vial and capped for storage. The diameter of the segments was measured to be between 0.21 mm-0.24 mm. An image of the dried fiber is presented in FIG. 13B.

Hydration and Coiling:

A small plastic weigh boat was placed on a hot plate, and several droplets of 2.0% sodium hyaluronate (MW=850 KDa) (HA) solution in PBS were added to the weigh boat. The viscosity of the HA/PBS solution was intended to simulate rabbit vitreous humor. The solution was heated to approximately 37° C. A coated fiber segment from Example 3A was placed into this viscous solution at 37° C., and coiled in less than 15 seconds into a helical shape.

Similarly, several droplets of 2.0% HA solution in PBS were added to a second weigh boat and heated to approximately 37° C. and a coated fiber segment from Example 3B was placed into the solution. This sample also coiled in less than 15 seconds. FIGS. 13C and 13D are photographs of the fiber taken from different perspectives.

Example 4—Coiling Hydrogel Fibers Containing Axitinib

Fiber Formation:

Buffer 1: Sodium phosphate dibasic (240 mg) was dissolved in deionized (DI) water and made up to 10 mL (24 mg/mL).

Buffer 2: Sodium phosphate monobasic (462.4 mg) was dissolved in deionized (DI) water and made up to 50 mL (9.25 mg/mL).

Syringe 1: Polyethylene glycol (PEG), MW=20 KDa, 4 arms (initiated with pentaerythritol), each arm end-capped with succimimidyl adipate (4a20 k PEG SAP, 16.7 mg) was weighed into a 1 mL, polyethylene (PE) syringe (BD) and dissolved in 108.4 mg of Buffer 2.

Syringe 2: Polyethylene glycol (PEG), MW=20 KDa, 8 arms (initiated with hexaglycerol), each arm end-capped with amine (8a20 k PEG $NH_2$, 8.3 mg) was weighed into a 1 mL, PE syringe (BD) and dissolved in 116.7 mg of Buffer 1.

The contents of syringe 1 and syringe 2 were mixed and injected into four segments of silicone tubing, each approximately 25 cm long, having an inner diameter of approximately 0.51 mm using a 21G needle. After gelation was confirmed, each tube was then transferred into a 37° C. chamber under a nitrogen sweep to dry for about 9 days. Each dried strand was gently stretched by manually pulling gently on both ends, causing necking, to form an oriented fiber along its full length. The final draw ratio was 4.5.

The necked fiber was pulled into a length of polyethylene tubing having an inner diameter of approximately 0.58 mm and the tubing was cut to a length approximately 3 cm shorter than the fiber. A 1.5 cm segment remained exposed outside of each end of the tubing, and each end of the taut fiber was taped to the side of a 140 mm aluminum weigh boat using laboratory tape. The curvature of the weigh boat was used to maintain the fiber's tautness against the inside wall of the tube.

Second Layer with Drug:

Syringe 3: 9.0 mg of 8a20 k PEG $NH_2$ was weighed into a 1 mL PE syringe and dissolved in 126 mg of the buffer 1.

Syringe 4: 18.0 mg of Polyethylene glycol (PEG), MW=20 KDa, 4 arms (initiated with pentaerythritol), each arm end-capped with succimimidyl adipate (4a20 k PEG SAP) was weighed into a 1 mL PE syringe and dissolved in 117 mg of Buffer 2.

Syringe 5: 30 mg of micronized Axitinib was weighed into a capped syringe.

The contents of the syringes 3 and 5 were mixed vigorously using a luer to luer connector. The contents of these syringes were then quantitatively transferred into one syringe, capped, and sonicated for 5 minutes to disperse all agglomerates. The contents of this syringe were then mixed with syringe 4 and injected into one end of the polyethylene tubing containing the fiber, filling the lumen to coat the fiber while the fiber was held in tension, and the coating was allowed to gel. After gelation of the coating, the sample, still attached to the weight boat, was transferred into the 37° C. chamber under a nitrogen sweep, where it remained for approximately 3.5 days. The tubing was cut to approximately 1cm segments and the fiber carefully removed from each segment. The diameter of coated fiber measured between 0.12 mm to 0.14 mm.

Example 5—Coiling Organogel Fibers Containing Bovine IgG

Fiber Formation:

Buffer 1: Sodium phosphate dibasic (240 mg) was dissolved in deionized (DI) water and made up to 10 mL (24 mg/mL).

Buffer 2: Sodium phosphate monobasic (462.4 mg) was dissolved in deionized (DI) water and made up to 50 mL (9.25 mg/mL).

Syringe 1: Polyethylene glycol (PEG), MW=20 KDa, 4 arms (initiated with pentaerythritol), each arm end-capped with succimimidyl adipate (4a20 k PEG SAP, 16.7 mg) was weighed into a 1 mL, polyethylene (PE) syringe (BD) and dissolved in 108.4 mg of Buffer 2.

Syringe 2: Polyethylene glycol (PEG), MW=20 KDa, 8 arms (initiated with hexaglycerol), each arm end-capped with amine (8a20 k PEG $NH_2$, 8.3 mg) was weighed into a 1 mL, PE syringe (BD) and dissolved in 116.7 mg of Buffer 1.

The contents of syringe 1 and syringe 2 were mixed and injected into four segments of silicone tubing, each approximately 25 cm long, having an inner diameter of approximately 0.51 mm using a 21G needle. After gelation was confirmed, each tube was then transferred into a 37° C. chamber under a nitrogen sweep to dry for about 9 days. Each dried strand was gently stretched by manually pulling gently on both ends, causing necking, to form an oriented fiber along its full length. The final draw ratio was 4.5.

The necked fiber was pulled into a length of polyethylene tubing having an inner diameter of approximately 0.58 mm and the tubing was cut to a length approximately 3 cm shorter than the fiber. A 1.5 cm segment remained exposed outside of each end of the tubing, and each end of the taut fiber was taped to the side of a 140 mm aluminum weigh boat using laboratory tape. The curvature of the weigh boat was used to maintain the fiber's tautness against the inside wall of the tube.

Second Layer with Drug:

Syringe 3: 9.0 mg of 8a20 k PEG $NH_2$ was weighed into a 1 mL PE syringe and dissolved in 126 mg of the Dimethyl carbonate.

Syringe 4: 18.0 mg of Polyethylene glycol (PEG), MW=20 KDa, 4 arms (initiated with pentaerythritol), each arm end-capped with succimimidyl adipate (4a20 k PEG SAP) was weighed into a 1 mL PE syringe and dissolved in 117 mg of Dimethyl carbonate.

Syringe 5: 30 mg of micronized Axitinib (see Micronization of Axitinib by Precipitation) was weighed into a capped syringe.

The contents of the syringes 3 and 5 were mixed vigorously using a luer to luer connector. The contents of these syringes were then quantitatively transferred into one syringe, capped, and sonicated for 5 minutes to disperse all agglomerates. The contents of this syringe were then mixed with syringe 4 and injected into one end of the polyethylene tubing containing the fiber, filling the lumen to coat the fiber while the fiber was held in tension, and the coating was allowed to gel. After gelation of the coating, the sample, still attached to the weight boat, was transferred into the 37° C. chamber under a nitrogen sweep, where it remained for overnight. The tubing was cut to approximately 1 cm segments and the fiber carefully removed from each segment. The diameter of coated fiber measured between 0.12 mm to 0.14 mm.

Example 6—Dimensions and Persistence of Coiling Bi-Polymeric Fibers Containing Bovine IgG Samples each consisted of coiling fiber comprised of a necked strand of Polyethylene glycol (PEG), MW=15 kDa, 8 arms (initiated with pentaerythritol), each arm end-capped with succinimidyl adipate (8a15 k PEG SAP, 4%), Polyethylene glycol (PEG), MW=20 kDa, 8 arms (initiated with hexaglycerol), each arm end-capped with amine (8a20 k PEG $NH_2$, 5.9%), and NHS-Fluorescein (0.1%), and a coating of 8a15 k PEG SAP (4%), 8a20 k PEG $NH_2$(5.9%), NHS-Fluorescein(0.1%), and Bovine IgG (10%). Details provided above are not repeated.

Fibers were cut to approximately 10 mm lengths. Fiber diameters were measured to be between 0.25 mm-0.30 mm. Several droplets of Phosphate Buffered Saline (PBS) solution (pH 7.4) were deposited into four small weigh boats and heated to approximately 37° C. on a hot plate. Each fiber sample was hydrated in a weigh boat of PBS solution for approximately 30 minutes. Samples rapidly coiled into helical coils upon hydration. After 30 minutes, each sample was measured to characterize the hydrated coil dimensions. FIGS. 14A-14B depicts the dimensions measures, and measured values are provided in the following table:

Dimensions Measured For Each Hydrated Coil At t=30 Minutes. (Note that W and D are the same).

| L | Ø | d | D |
|---|---|---|---|
| 1.8 mm-2.1 mm | 0.57 mm-0.70 mm | 0.34 mm-0.65 mm | 1.5 mm-2.2 mm |

Following dimensional measurements, each coil was placed into a 10 mL vial filled with Tris Buffered Saline (TBS) solution (pH 8.51) and transferred into a 37° C. chamber. Coils were observed periodically over the course of storage at 37° C. and remained in a coiled shape for between 7 to 8 days, at which time the coils began to unravel. The remnants of these coils began to break apart between 8 and 9 days of storage in TBS pH 8.51 at 37° C.

Example 7—Coiling Hydrogel Fiber Containing Fast Degrading Necked Fiber

Using a rapidly degrading necked fiber results in increased exposed surface area once the necked portion has dissolved. Changing the geometry of the necked portion, particularly diameter, will directly affect the amount of increased surface area exposed once the necked fiber degrades.

Fiber Formation:

Buffer 1: Sodium phosphate dibasic (240 mg) was dissolved in deionized (DI) water and made up to 10 mL (24 mg/mL).

Buffer 2: Sodium phosphate monobasic (462.4 mg) was dissolved in deionized (DI) water and made up to 50 mL (9.25 mg/mL).

Syringe 1: Polyethylene glycol (PEG), MW=20 KDa, 4 arms (initiated with pentaerythritol), each arm end-capped with succimimidyl succinate (8a15 k PEG SS, 5.4 mg) was weighed into a 1 mL, polyethylene (PE) syringe (BD) and dissolved in 119.6 mg of Buffer 2.

Syringe 2: Polyethylene glycol (PEG), MW=20 KDa, 8 arms (initiated with hexaglycerol), each arm end-capped with amine (8a20 k PEG $NH_2$, 7.1 mg) was weighed into a 1 mL, PE syringe (BD) and dissolved in 117.9 mg of Buffer 1.

The contents of syringe 1 and syringe 2 were mixed and injected into four segments of silicone tubing, each approximately 25 cm long, having an inner diameter of approximately 0.51 mm using a 21G needle. After gelation was confirmed, each tube was then transferred into a 37° C. chamber under a nitrogen sweep to dry for about 9 days. Each dried strand was gently stretched by manually pulling gently on both ends, causing necking, to form an oriented fiber along its full length. The final draw ratio was 4.5.

The necked fiber was pulled into a length of polyethylene tubing having an inner diameter of approximately 0.58 mm and the tubing was cut to a length approximately 3 cm shorter than the fiber. A 1.5 cm segment remained exposed outside of each end of the tubing, and each end of the taut fiber was taped to the side of a 140 mm aluminum weigh boat using laboratory tape. The curvature of the weigh boat was used to maintain the fiber's tautness against the inside wall of the tube.

Second Layer with Drug:

Syringe 3: 9.0 mg of 8a20 k PEG $NH_2$ was weighed into a 1 mL PE syringe and dissolved in 126 mg of the buffer 1.

Syringe 4: 18.0 mg of Polyethylene glycol (PEG), MW=20 KDa, 4 arms (initiated with pentaerythritol), each arm end-capped with succimimidyl adipate (4a20 k PEG SAP) was weighed into a 1 mL PE syringe and dissolved in 117 mg of buffer 2.

Syringe 5: 30 mg of micronized Axitinib (see Micronization of Axitinib by Precipitation) was weighed into a capped syringe.

The contents of the syringes 3 and 5 were mixed vigorously using a luer to luer connector. The contents of these syringes were then quantitatively transferred into one syringe, capped, and sonicated for 5 minutes to disperse all agglomerates. The contents of this syringe were then mixed with syringe 4 and injected into one end of the polyethylene tubing containing the fiber, filling the lumen to coat the fiber while the fiber was held in tension, and the coating was allowed to gel. After gelation of the coating, the sample, still attached to the weight boat, was transferred into the 37° C. chamber under a nitrogen sweep, where it remained for overnight. The tubing was cut to approximately 1 cm segments and the fiber carefully removed from each segment. The diameter of coated fiber measured between 0.12 mm to 0.14 mm.

Example 8—Coiling Organogel Fiber Containing Fast Degrading Necked Fiber

Fiber Formation:

Buffer 1: Sodium phosphate dibasic (240 mg) was dissolved in deionized (DI) water and made up to 10 mL (24 mg/mL).

Buffer 2: Sodium phosphate monobasic (462.4 mg) was dissolved in deionized (DI) water and made up to 50 mL (9.25 mg/mL).

Syringe 1: Polyethylene glycol (PEG), MW=20 KDa, 4 arms (initiated with pentaerythritol), each arm end-capped with succimimidyl succinate (8a15 k PEG SS, 5.4 mg) was weighed into a 1 mL, polyethylene (PE) syringe (BD) and dissolved in 119.6 mg of Buffer 2.

Syringe 2: Polyethylene glycol (PEG), MW=20 KDa, 8 arms (initiated with hexaglycerol), each arm end-capped with amine (8a20 k PEG $NH_2$, 7.1 mg) was weighed into a 1 mL, PE syringe (BD) and dissolved in 117.9 mg of Buffer 1.

The contents of syringe 1 and syringe 2 were mixed and injected into four segments of silicone tubing, each approximately 25 cm long, having an inner diameter of approximately 0.51 mm using a 21G needle. After gelation was confirmed, each tube was then transferred into a 37° C. chamber under a nitrogen sweep to dry for about 9 days. Each dried strand was gently stretched by manually pulling gently on both ends, causing necking, to form an oriented fiber along its full length. The final draw ratio was 4.5.

The necked fiber was pulled into a length of polyethylene tubing having an inner diameter of approximately 0.58 mm and the tubing was cut to a length approximately 3 cm shorter than the fiber. A 1.5 cm segment remained exposed outside of each end of the tubing, and each end of the taut fiber was taped to the side of a 140 mm aluminum weigh boat using laboratory tape. The curvature of the weigh boat was used to maintain the fiber's tautness against the inside wall of the tube.

Second Layer with Drug:

Syringe 3: 9.0 mg of 8a20 k PEG $NH_2$ was weighed into a 1 mL PE syringe and dissolved in 126 mg of the Dimethyl carbonate.

Syringe 4: 18.0 mg of Polyethylene glycol (PEG), MW=20 KDa, 4 arms (initiated with pentaerythritol), each arm end-capped with succimimidyl adipate (4a20 k PEG SAP) was weighed into a 1 mL PE syringe and dissolved in 117 mg of Dimethyl carbonate.

Syringe 5: 30 mg of micronized Axitinib (by precipitation) was weighed into a capped syringe.

The contents of the syringes 3 and 5 were mixed vigorously using a luer to luer connector. The contents of these syringes were then quantitatively transferred into one syringe, capped, and sonicated for 5 minutes to disperse all agglomerates. The contents of this syringe were then mixed with syringe 4 and injected into one end of the polyethylene tubing containing the fiber, filling the lumen to coat the fiber while the fiber was held in tension, and the coating was allowed to gel. After gelation of the coating, the sample, still attached to the weight boat, was transferred into the 37° C. chamber under a nitrogen sweep, where it remained for overnight. The tubing was cut to approximately 1 cm segments and the fiber carefully removed from each segment. The diameter of coated fiber measured between 0.12 mm to 0.14 mm.

Example 9—Micronization of Axitinib by Precipitation

Axitinib Micronization:

195 mg of Axitinib (manufactured by LGM Pharma, GMP grade) was dissolved into 110 mL of Ethanol (Sigma Aldrich) in a glass serum vial, capped and crimped (1.77 mg Axitinib/mL ethanol). This vial was then wrapped in aluminum foil to protect the solution from light, and sonicated for 20 minutes until completely dissolved. Solution was then aspirated into two 60 mL polyethylene (PE) luer-lok syringes (BD) wrapped in aluminum foil.

Axitinib Precipitation:

1800 mL of sterile Water For Injection (WFI) was measured into a 2 L beaker and placed on a stir plate stirring at 600 RPM with a stir bar, creating a large WFI vortex in the center of the beaker. One 60 mL BD syringe containing axitinib in ethanol was placed on a syringe pump which had been clamped above the WFI beaker. A hypodermic needle (21G, BD) was connected to the syringe and aimed directly into the center of the vortex for dispensation of the axitinib solution. The syringe pump was then run at 7.5 mL/min in order to add the axitinib solution dropwise to the WFI to precipitate micronized Axitinib.

Axitinib Suspension Filtration and Collection:

After micronization, the Axitinib suspended in 5.7% ethanol/94.3% WFI was filtered through a 0.2 um vacuum filter (Thermo Scientific) and rinsed 3× with 100 mL of WFI. After filtration, Axitinib powder was collected from the filter using a spatula, and vacuum dried overnight in a 10 mL serum vial to remove all excess solvent.

Particle Size Analysis:

Particle size was analyzed using a Beckman Coulter LS 120 Particle Size Analyzer. Samples were sonicated for 15 minutes in Deionized water before analysis. On average the particle size distribution is such: d10=0.773 um, d50=2.605 um, d90=6.535 um.

Example 10—Illustrated Description of Processes Used to Make Coiling Bi-Polymeric Fibers 1. Formulate PEG solutions (aqueous or organic), and transfer into syringes (PEG Ester solution in one syringe, FIG. 15B PEG Amine solution in a separate syringe. Can also include an Active Pharmaceutical Agent (API), either in a third syringe or in one or both of the PEG syringes.
2. Mix contents of each syringe together and inject into small ID tubing, (in this Example, 0.51 mm ID).
3. Allow to crosslink, then dry inside the tubing (may use heat, inert gas sweep, vacuum, or a combination of any of these) to form a fiber, see FIG. 15A.
4. Remove Dried fiber from the tubing, FIG. 15B. 5. Stretch/neck the dry fiber. Fiber holds the thinner, elongated shape, FIGS. 15C-15E, with stretched fiber shown in FIG. 15F.
6. Thread fiber into small inner diameter polyethylene tube, with ends of fiber exposed outside of the tube.
7. Wrap tube and fiber around a curved surface. Fix both ends of the fiber such that it is held taught around the inner surface of the tubing curve.
8. Prepare hydrogel precursor solutions and mix (same process as Steps 1 and 2). Inject the hydrogel into the polyethylene tubing containing the stretched fiber.
9. Allow to crosslink, then dry inside the tubing (same methods as Step 3).
10. Once dry, remove from tubing and cut to desired length.

Example 11—Alternative Process for Necking, Coating, and Drying Coiling BiPolymer Fibers 1. Cast hydrogel or organogel and dry as previously disclosed or by similar method. Maximum length of strand cast will be dependent on the rate of crosslinking (gel time) vs tube length and inner diameter.
2. Fixture or clamp tubing to hold straight. This may be done using a block that is as long, or longer than the tubing length, with a semi-circular grove through the length of the block that snugly fits around the tubing, or another similar method. Cut away end of tubing and grasp dried strand.
3. Pull out to expose the fiber end from the tubing. Thread the end of the fiber through the looped/hooked end of a ligature, wire, or other similar device. Use this device to thread the fiber through a die or other tool to draw down the diameter while stretching the fiber.
   a. Tool design to uniformly neck the fiber without imparting enough drag due to friction to cause sufficient resistance to tear the fiber. Gradual taper, smooth surfaces in contact with fiber.
4. Continue to thread necked fiber into the tubing that will be used to cast the coating gel.
   a. Tubing may be continuous length, or a series of shorter segments. Gel will be cast into each individual length of tubing, and segment length will be determined by the gel time of the coating gel.
5. Remove ligature/wire device and connect the necked fiber to a large cylindrical drum. Rotate the drum to uptake the tubing and necked fiber onto the drum surface. Once completely wrapped around the drum, connect the free end to the drum, holding the fiber wrapped tightly and taut.
   a. Additional support of the tubing may be required, and can use grooves formed into the surface of the drum, features to clamp/hold the tubing against the drum, or other means.
6. Cast gel into tube segment(s). Dry while held taut onto the drum.

Example 12: Fiber Component Formed from Organogel

Bipolymer fibers formed from organogel (Example 3A or 3B) were further tested for degradation and found to last longer in vivo before full degradation compared to the same compositions made in aqueous solution. The difference in persistence was enough to provide for effectively complete dissolution of the aqueous-based polymer while the organogel-derived hydrogel was still persistent.

Example 13: Use of Multiple Fibers Yields Faster Coiling Rate

Fiber Formation

Syringe 1: Targeted 40 mg of Polyethylene glycol (PEG), MW=20 KDa, 4 arms (initiated with pentaerythritol), each arm end-capped with succinimidyl azelate (4a20 k PEG SAZ) was weighed into a 1 mL PE syringe and dissolved in 360 mg of Dimethyl carbonate.

Syringe 2: Targeted 20 mg of Polyethylene glycol (PEG), MW=20 KDa, 8 arms (initiated with hexaglycerol), each arm end-capped with an amine (8a20 k PEG $NH_2$) was weighed into a 1 mL PE syringe and dissolved in 380 mg of Dimethyl carbonate.

The contents of syringe 1 and syringe 2 were mixed and injected into polyurethane tubing, each approximately 5 m long, having an inner diameter of approximately 0.20 mm using a 31G cannula. After gelation was confirmed, each tube was then transferred into a 37° C. chamber under a nitrogen sweep to dry for about 1 day. Each dried strand segment of approximately 10 cm length was gently stretched by manually pulling gently on both ends, causing necking, to form an oriented fiber along its full length. The final draw ratio was 5.

Each necked fiber (done with 1, 2, 3, 5, 7, or 9 fibers) was pulled into a length of polyurethane tubing having an inner diameter of approximately 0.508 mm and the tubing was cut to 25 cm in length. A 2.5 cm segment of each fiber remained exposed outside of each end of the tubing, and each end of the taut fiber was taped to the side of a 140 mm aluminum weigh boat using laboratory tape. The curvature of the weigh boat was used to maintain the fiber's tautness against the inside wall of the tube.

Second Layer with Drug:

Syringe 3: Targeted 16.8 mg of 8a20 k PEG $NH_2$ was weighed into a 1 mL PE syringe and dissolved in 130.25 mg of the Dimethyl carbonate.

Syringe 4: Targeted 8.0 mg of Polyethylene glycol (PEG), MW=15 KDa, 8 arms (initiated with pentaerythritol), each arm end-capped with succimimidyl adipate (8a15 k PEG SAP) and 7.1 mg of Polyethylene glycol (PEG), MW=20 KDa, 4 arms (initiated with pentaerythritol), each arm end-capped with succimimidyl adipate (4a20 k PEG SAP) were each weighed into the same 1 mL PE syringe and dissolved in 131.9 mg of Dimethyl carbonate.

Spray-dried powder: Bovine IgG (Sigma Aldrich) was spray-dried using a Buchi B290 spray-drier to form particles with a median diameter of approximately 7.5 microns. The spray-dried powder composition was approximately 70% IgG, 28% sucrose and 2% buffer salts.

Syringe 5: Targeted 106 mg of spray-dried Bovine IgG was weighed into a capped syringe.

The contents of the syringes 3 and 5 were mixed vigorously using a luer to luer connector. The contents of these syringes were then quantitatively transferred into one syringe, capped, and sonicated for 15 minutes to disperse all agglomerates under cold conditions (8-15° C.). The contents of this syringe were then mixed with syringe 4 and injected into one end of the polyurethane tubing containing the fiber, filling the lumen to coat the fiber while the fiber was held in tension, and the coating was allowed to gel. After gelation of the coating, the sample, still attached to the weight boat, was transferred into the 37° C. chamber under a nitrogen sweep, where it remained for 5 days. The tubing was cut to approximately 2.54 cm segments and the fiber carefully removed from each segment. The diameter of coated fiber ranged from 0.31 to 0.35 mm.

Coil rate determined by injecting 2.54 cm segment into 37° C. 2.0% sodium hyaluronate (MW=850 KDa) (HA) solution in PBS over a 2 second period and the time was recorded for the segment to achieve a coiled shape. Results are shown in FIG. 19.

Example 14: Use of Larger Fibers Yields Faster Coiling Rate

Fiber Formation:

Syringe 1: Targeted 40 mg of Polyethylene glycol (PEG), MW=20 KDa, 4 arms (initiated with pentaerythritol), each arm end-capped with succinimidyl azelate (4a20 k PEG SAZ) was weighed into a 1 mL PE syringe and dissolved in 360 mg of Dimethyl carbonate.

Syringe 2: Targeted 20 mg of Polyethylene glycol (PEG), MW=20 KDa, 8 arms (initiated with hexaglycerol), each arm end-capped with an amine (8a20 k PEG $NH_2$) was weighed into a 1 mL PE syringe and dissolved in 380 mg of Dimethyl carbonate.

The contents of syringe 1 and syringe 2 were mixed and injected into a volume appropriate length of polyurethane tubing, having an inner diameters of each 0.203, 0.35, and 0.508 mm using an appropriately sized cannula. After gelation was confirmed, each tube was then transferred into a 37° C. chamber under a nitrogen sweep to dry for about 2 days. Each dried strand segment of approximately 10 cm length was gently stretched by manually pulling gently on both ends, causing necking, to form an oriented fiber along its full length. The final draw ratio was 5.

A necked fiber was pulled into a length of polyurethane tubing having an inner diameter of approximately 0.508 mm and the tubing was cut to 25 cm in length. A 2.5 cm segment of each fiber remained exposed outside of each end of the tubing, and each end of the taut fiber was taped to the side of a 140 mm aluminum weigh boat using laboratory tape. The curvature of the weigh boat was used to maintain the fiber's tautness against the inside wall of the tube.

Second Layer with Drug:

Syringe 3: Targeted 16.0 mg of 8a20 k PEG $NH_2$ was weighed into a 1 mL PE syringe and dissolved in 149.5 mg of the Dimethyl carbonate.

Syringe 4: Targeted 9.0 mg of Polyethylene glycol (PEG), MW=15 KDa, 8 arms (initiated with pentaerythritol), each arm end-capped with succimimidyl adipate (8a15 k PEG SAP) and 8.0 mg of Polyethylene glycol (PEG), MW=20 KDa, 4 arms (initiated with pentaerythritol), each arm end-capped with succimimidyl adipate (4a20 k PEG SAP) were each weighed into the same 1 mL PE syringe and dissolved in 148.5 mg of Dimethyl carbonate.

Syringe 5: Targeted 119 mg of spray dried Bovine IgG was weighed into a capped syringe.

The contents of the syringes 3 and 5 were mixed vigorously using a luer to luer connector. The contents of these syringes were then quantitatively transferred into one syringe, capped, and sonicated for 15 minutes to disperse all agglomerates under cold conditions (8-15° C.). The contents of this syringe were then mixed with syringe 4 and injected into one end of the polyurethane tubing containing the fiber, filling the lumen to coat the fiber while the fiber was held in tension, and the coating was allowed to gel. After gelation of the coating, the sample, still attached to the weight boat, was transferred into the 37° C. chamber under a nitrogen sweep, where it remained for 4 days. The tubing was cut to approximately 2.54 cm segments and the fiber carefully removed from each segment. The diameter of coated fibers were 0.33 mm.

Figure 20:
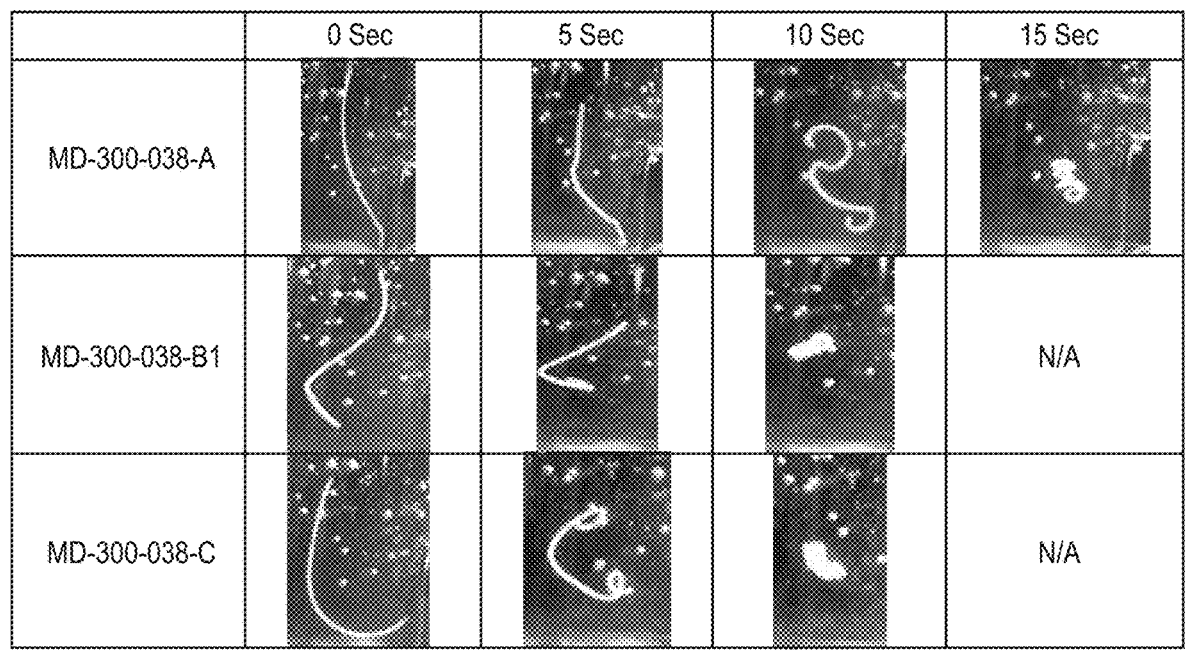
FIG. 20 provides results of an experiment set forth in Example 14, with vehicles of various diameters correlated to a time required to form the coil shape depot containing bovine IgG.

Coil rate determined by injecting 2.54 cm segment into 37° C. 2.0% sodium hyaluronate (MW=850 KDa) (HA) solution in PBS over a 2 second period and the time was recorded for the segment to achieve a coiled shape. Results are shown in FIG. 20.

Example 15: Multiple Segments that Entangle Upon Hydration Induced Coiling

Fiber Formation:

Syringe 1: Targeted 45 mg of Polyethylene glycol (PEG), MW=20 KDa, 4 arms (initiated with pentaerythritol), each arm end-capped with succinimidyl azelate (4a20 k PEG SAZ) was weighed into a 1 mL PE syringe and dissolved in 405 mg of Dimethyl carbonate.

Syringe 2: Targeted 22.5 mg of Polyethylene glycol (PEG), MW=20 KDa, 8 arms (initiated with hexaglycerol), each arm end-capped with an amine (8a20 k PEG NH$_2$) was weighed into a 1 mL PE syringe and dissolved in 427.5 mg of Dimethyl carbonate.

The contents of syringe 1 and syringe 2 were mixed and injected into polyurethane tubing, each approximately 5 m long, having an inner diameter of approximately 0.35 mm using a 27G cannula. After gelation was confirmed, each tube was then transferred into a 37° C. chamber under a nitrogen sweep to dry for about 2 days. Each dried strand segment of approximately 15 cm length was gently stretched by manually pulling gently on both ends, causing necking, to form an oriented fiber along its full length. The final draw ratio was 5.

Two necked fibers were pulled into a length of polyurethane tubing having an inner diameter of approximately 0.508 mm and the tubing was cut to 25 cm in length. A 2.5 cm segment of each fiber remained exposed outside of each end of the tubing, and each end of the taut fiber was taped to the side of a 140 mm aluminum weigh boat using laboratory tape. The curvature of the weigh boat was used to maintain the fiber's tautness against the inside wall of the tube.

Second Layer with Drug:

Syringe 3: Targeted 14.25 mg of 8a20 k PEG NH$_2$ was weighed into a 1 mL PE syringe and dissolved in 132.8 mg of the Dimethyl carbonate.

Syringe 4: Targeted 8.0 mg of Polyethylene glycol (PEG), MW=15 KDa, 8 arms (initiated with pentaerythritol), each arm end-capped with succimimidyl adipate (8a15 k PEG SAP) and 7.1 mg of Polyethylene glycol (PEG), MW=20 KDa, 4 arms (initiated with pentaerythritol), each arm end-capped with succimimidyl adipate (4a20 k PEG SAP) were each weighed into the same 1 mL PE syringe and dissolved in 131.9 mg of Dimethyl carbonate.

Syringe 5: Targeted 106 mg of spray dried Bovine IgG was weighed into a capped syringe.

The contents of the syringes 3 and 5 were mixed vigorously using a luer to luer connector. The contents of these syringes were then quantitatively transferred into one syringe, capped, and sonicated for 15 minutes to disperse all agglomerates under cold conditions (8-15° C.). The contents of this syringe were then mixed with syringe 4 and injected into one end of the polyurethane tubing containing the fiber, filling the lumen to coat the fiber while the fiber was held in tension, and the coating was allowed to gel. After gelation of the coating, the sample, still attached to the weight boat, was transferred into the 37° C. chamber under a nitrogen sweep, where it remained for 4 days. The tubing was cut to either 15 or 12 mm segments at either 30, 45, 52.5, or 60° angles (0° angle would be a perpendicular cut along the tubing). The diameter of coated fiber ranged from 0.33 to 0.35 mm.

Fiber injection distance, the maximum distance the fiber could potentially reach during injection, was evaluated by injecting various segment numbers and lengths totaling to 60 mm that are parallel loaded into a needle into 37° C. 2.0% sodium hyaluronate (MW=850 KDa) (HA) solution in PBS and recording videos. A hoop of wire is used to approximate the OD of a human eye as a visualization aid for some of the injections. Results are shown in FIG. 21.

Example 16: Angle Cut of Multiple Segments

Fiber Formation:

Syringe 1: Targeted 45 mg of Polyethylene glycol (PEG), MW=20 KDa, 4 arms (initiated with pentaerythritol), each arm end-capped with succinimidyl azelate (4a20 k PEG SAZ) was weighed into a 1 mL PE syringe and dissolved in 405 mg of Dimethyl carbonate.

Syringe 2: Targeted 22.5 mg of Polyethylene glycol (PEG), MW=20 KDa, 8 arms (initiated with hexaglycerol), each arm end-capped with an amine (8a20 k PEG NH$_2$) was weighed into a 1 mL PE syringe and dissolved in 427.5 mg of Dimethyl carbonate.

The contents of syringe 1 and syringe 2 were mixed and injected into polyurethane tubing, each approximately 5 m long, having an inner diameter of approximately 0.35 mm using a 27G cannula. After gelation was confirmed, each tube was then transferred into a 37° C. chamber under a nitrogen sweep to dry for about 2 days. Each dried strand segment of approximately 15 cm length was gently stretched by manually pulling gently on both ends, causing necking, to form an oriented fiber along its full length. The final draw ratio was 5.

Two necked fibers were pulled into a length of polyurethane tubing having an inner diameter of approximately 0.508 mm and the tubing was cut to 25 cm in length. A 2.5 cm segment of each fiber remained exposed outside of each end of the tubing, and each end of the taut fiber was taped to the side of a 140 mm aluminum weigh boat using laboratory tape. The curvature of the weigh boat was used to maintain the fiber's tautness against the inside wall of the tube.

Second Layer with Drug:

Syringe 3: Targeted 16.0 mg of 8a20 k PEG NH$_2$ was weighed into a 1 mL PE syringe and dissolved in 149.5 mg of the Dimethyl carbonate.

Syringe 4: Targeted 9.0 mg of Polyethylene glycol (PEG), MW=15 KDa, 8 arms (initiated with pentaerythritol), each arm end-capped with succimimidyl adipate (8a15 k PEG SAP) and 8.0 mg of Polyethylene glycol (PEG), MW=20 KDa, 4 arms (initiated with pentaerythritol), each arm end-capped with succimimidyl adipate (4a20 k PEG SAP) were each weighed into the same 1 mL PE syringe and dissolved in 148.5 mg of Dimethyl carbonate.

Syringe 5: Targeted 119 mg of spray dried Bovine IgG was weighed into a capped syringe.

The contents of the syringes 3 and 5 were mixed vigorously using a luer to luer connector. The contents of these syringes were then quantitatively transferred into one syringe, capped, and sonicated for 15 minutes to disperse all agglomerates under cold conditions (8-15° C.). The contents of this syringe were then mixed with syringe 4 and injected into one end of the polyurethane tubing containing the fiber, filling the lumen to coat the fiber while the fiber was held in tension, and the coating was allowed to gel. After gelation of the coating, the sample, still attached to the weight boat, was transferred into the 37° C. chamber under a nitrogen sweep, where it remained for 5 days. The tubing was cut to either 15 or 12 mm segments at either 30, 45, 52.5, or 60° angles (0° angle would be a perpendicular cut along the tubing). The diameter of coated fiber ranged from 0.33 to 0.35 mm.

Fiber training, the phenomenon where one segment pushes its preceding segment during injection increasing the maximum distance a fiber travels from the injection needle tip, was evaluated by injecting various length segments parallel loaded into a needle into 37° C. 2.0% sodium hyaluronate (MW=850 KDa) (HA) solution in PBS and recording videos. A hoop of wire is used to approximate the OD of a human eye as a visualization aid. Results are shown in FIG. 22.

Example 17

Example: Necked and Coiled Fibers—Formulation and In Vivo Delivery of Axitinib

Formulation 1: Necked Fiber Preparation
Buffer Preparation:

Buffer 1: 600.0 mg of Sodium phosphate dibasic was weighed into a 25 mL volumetric flask, and brought to volume with deionized water. Preparation was then stirred until dibasic appears to be fully in solution. The result is a 24 mg/mL dibasic solution.

Buffer 2: 225.0 mg of Sodium phosphate monobasic was weighed into a 25 mL volumetric flask, and brought to volume with deionized water. Preparation was then stirred until monobasic appears to be fully in solution. The result is a 9 mg/mL monobasic solution.

Fiber Casting with Drug Loaded Hydrogel:

Syringe 3: Polyethylene glycol (PEG), MW=20 KDa, 8 arms, each arm end-capped with amine (8a20 k PEG $NH_2$, 12.0 mg) was weighed into a 1 mL glass syringe (Cadence) and dissolved in 228.0 µL of Buffer 1.

Syringe 4: Polyethylene glycol (PEG), MW=20 KDa, 4 arms (initiated with pentaerythritol), each arm end-capped with succimimidyl azelate (4a20 k PEG SAZ, 24.0 mg) was weighed into a 1 mL glass syringe and dissolved in 216.0 µL of Buffer 2.

Syringe 5: 53.3 mg of Shilpa manufactured Axitinib was weighed into a capped 1 mL glass syringe.

The contents of the syringes 3 and 5 were mixed vigorously using a luer to luer connector. The contents of these syringes were then quantitatively transferred into one syringe, capped, and sonicated for 5 minutes to disperse all agglomerates. The contents of this syringe were then mixed with syringe 4 and injected into one end of a 4 ft segment polyurethane tubing with an inner diameter of 0.76 mm with a 21G 1.5" needle (Becton Dickinson) Gel time was approximately 2.5 minutes. Segments were then transferred to a saturated aqueous environment to cure for approximately 60 minutes. After curing, segments were cut to 12 inches and placed in a nitrogen sweep at room temperature and allowed to dry for about 48 hours. Once dry, fibers were removed from the tubing. Each dried strand was gently stretched by manually pulling gently on both ends, causing necking, to form an oriented fiber along its full length (initial length 254 mm, final length 762 mm). The final draw ratio was 3.0.

Formulation 2: Coiled Fiber Preparation
Buffer Preparation:

Prebuffer 1: 600.0 mg of Sodium phosphate dibasic was dissolved in 25 mL deionized water.

Prebuffer 2: 225.0 mg of Sodium phosphate monobasic was dissolved in 25 mL deionized water.

Fiber element 1 (E1); formation of a necked fiber for use as the fiber backbone: Syringe 1: The precursor polymer from Example 1 (4a50 kPEG AZA, 30.0 mg) was weighed into a 1 mL, polyethylene (PE) syringe (BD) and dissolved in 145.1 µL of dimethyl carbonate (DMC).

Syringe 2: Polyethylene glycol (PEG), MW=20 KDa, 4 arms, each arm end-capped with succinimidyl carbonate (4a20 k PEG SC, 12.0 mg) was weighed into a 1 mL, PE syringe (BD) and dissolved in 163.1 µL of DMC.

The contents of syringe 1 and syringe 2 were mixed and injected into one 46 cm length of polyurethane tubing (80 A durometer), having an inner diameter of approximately 0.20 mm using a 30G needle. After gelation was confirmed (about 15 seconds), the tubing containing the gel was cut into 101 mm segments and each segment was then transferred into a chamber holding a saturated dimethyl chloride (DMC) environment for about 15 minutes. Segments were transferred to a 37° C. chamber under a nitrogen sweep to dry for about 24 hours. Each dried strand was gently stretched by manually pulling gently on both ends, causing necking, to form an oriented fiber along its full length (initial length 26 mm, final length 164 mm). The final draw ratio was 6.3.

The effective draw ratio was reduced by shrinking the necked fiber using heat to melt the PEG crystalline regions. To do this step, the 164 mm necked fiber was inserted into a length of PTFE tubing having an inner diameter of approximately 0.802 mm and a length of 150 mm, and was then adhered to the outer curved surface of an aluminum weigh boat to keep the ends of the fiber firmly secured at a length of 164 mm, leaving slack in the dry necked fiber between the fixation points on either side of the tubing. The entire weigh boat was then placed into a 40° C. chamber under nitrogen sweep to shrink back the necked fiber using heat to the predetermined length of 164 mm. Once the fiber was taught at a length of 164 mm (overnight), the weigh boat was removed from the oven for the next step.

Fiber Element 2 (E2): Coating with Drug Loaded Hydrogel:

Syringe 3: Polyethylene glycol (PEG), MW=20 KDa, 8 arms, each arm end-capped with amine (8a20 k PEG $NH_2$, 12.0 mg) was weighed into a 1 mL glass syringe (Cadence) and dissolved in 228.0 µL of Prebuffer 1.

Syringe 4: Polyethylene glycol (PEG), MW=20 KDa, 4 arms (initiated with pentaerythritol), each arm end-capped with succimimidyl azelate (4a20 k PEG SAZ, 24.0 mg) was weighed into a 1 mL glass syringe and dissolved in 216.0 µL of Prebuffer 2.

Syringe 5: 53.3 mg of axitinib was weighed into a capped 1 mL glass syringe.

The contents of the syringes 3 and 5 were mixed vigorously using a luer to luer connector. The contents of these syringes were transferred into one syringe, capped, and placed in a sonication bath for 5 minutes to disperse agglomerated particles. The contents of this syringe were then mixed with syringe 4 and injected into the PTFE tubing containing the fiber, filling the lumen to coat the E1 fiber while the fiber was still held in tension, and the coating was allowed to gel (gel time ~2.5 min). After gelation, the sample, still attached to the weight boat, was transferred into a chamber holding a saturated water environment for about 70 minutes. Then the sample while still attached to the weight boat was transferred into the 37° C. chamber under a nitrogen sweep for approximately 7 days to dry.

Fiber Injection:

Fibers were cut to 20 mm lengths and loaded into a 27G UTW 1" needle (JBP). The needles were then luer locked to a 50 uL Hamilton glass syringe with a 0.010" diameter push rod (2.0" long) in the barrel. This push rod would successfully deploy the fiber as the plunger was depressed in the barrel of the syringe. The fibers would then either coil upon hydration (Coiled fiber formulation 2), or shrink and fatten (Necked Fiber formulation 1).

Study Design:

The tolerability, pharmacokinetics, and pharmacodynamics of the formulations from examples 1 and 2 were evaluated in Dutch belted rabbits through 6 months. 112 eyes of naïve Dutch belted rabbits (n=66) were bilaterally dosed with either a necked fiber or a coiled fiber and were sacrificed at 1, 3 and 6 months to test for biocompatibility or pharmacokinetics.

In Vivo Drug Release:

Drug release from the fibers over time in vivo was characterized over time by two different methods. The first method was qualitative in nature. Infrared fundus images were collected bi-weekly over a 6 month period, with the intent of imaging the coiled fiber in the vitreous. Over time, the fiber becomes more translucent and porous, indicating drug solubilizing out of the hydrogel matrix and being delivered to the target tissues. Additionally, the hydrogel depots themselves begin to shrink in size as the hydrogel degraded and releases drug. Drug release over time was also characterized in a more quantitative method by analyzing the explanted depots at terminal time points (1, 3 and 6 months) by LC-MS/MS (liquid chromatography with dual mass spectroscopy). The results show a declining quantity of drug in the depots over time throughout the study.

In Vivo Drug Delivery:

Drug delivery to the tissues over time was captured quantitatively by performing tissue concentration analysis at several time points over the 6 month period (1, 3 and 6 months). Eyes at each time point were enucleated and flash frozen using liquid nitrogen. While frozen, eyes were dissected; the vitreous humor was removed and collected, then the retina and choroid were collected in that order. The vitreous humor was then allowed to thaw, and the fiber depots were removed from the sample. All tissues were then homogenized and the drug was extracted using a methanol media. Samples were tested against a stock standard curve by LC-MS/MS using stock axitinib. This analysis showed an increasing concentration of axitinib in these target tissues (>313 ng drug/g of target tissues at all time points) over the duration of the 6 month study. Based on the half-life and clearance rates of axitinib, these tissue concentrations could have only been possible with the constant and sustained delivery of axitinib from the delivery device.

TABLE 17-1

Drug remaining in explanted depots by LC-MS/MS from both formulations at 1, 3, and 6 months showing a progression of drug release from the depots over time

|  | 1 month | 3 month | 6 month |
| --- | --- | --- | --- |
| Axitinib remaining in Necked (μg) | 238 | 67 | 55 |
| Axitinib remaining in Coiled (μg) | 290 | 120 | 110 |

Table 17-2 showing the ng axitinib/g tissue and subsequent calculated values of the compiled pharmokinetic (PK) data for the OTX-TKI Necked Fiber (Formulation 1). These values over time show an increasing concentration of axitinib in the tissues thus demonstrating continued release of drug from the fiber depot over the 6 month period. The amount of axitinib, ng, per gram, of tissue, g, is shown for each of the choroid, retina, vitrous humor (VH), remaining in the vehicle (depot), aqueous humor (AH), and plasma are listed. The concentration in the retina is also listed as a multiple of the $IC_{50}$ for effectiveness (half of maximal effectiveness), e.g., 6934× the required $IC_{50}$ at week 4; this data is also expressed in log format with the standard deviation.

| Weeks | Choroid | Retina | VH | Depot | AH | Plasma |
| --- | --- | --- | --- | --- | --- | --- |
|  | ng/g |  |  |  |  |  |
| 4 | 313 | 536 | 476 | 238 | 3.66125 | <LLOQ |
| 12 | 1061 | 456 | 585 | 66.85 | <LLOQ | <LLOQ |
| 26 | 1675 | 8312 | 4609 | 55 | <LLOQ | <LLOQ |
|  | nM |  |  |  |  |  |
| 4 | 809 | 1387 | 1233 | 614 | 9 | <LLOQ |
| 12 | 2744 | 1181 | 1512 | 173 | <LLOQ | <LLOQ |
| 26 | 4333 | 21507 | 11924 | 142 | <LLOQ | <LLOQ |

| Weeks | Retina |
| --- | --- |
| $xIC_{50}$ | |
| 4 | 6934 |
| 12 | 5904 |
| 26 | 107533 |
| LOG $xIC_{50}$ | |
| 4 | 3.8 |
| 12 | 3.8 |
| 26 | 5.0 |
| LOG $xIC_{50}$ Standard Dev | |
| 4 | 0.29 |
| 12 | 0.26 |
| 26 | 0.78 |

Table 17-3 showing the ng axitinib/g tissue and subsequent calculated values of the compiled PK data for the OTX-TKI Coiled Fiber (Formulation 2). These values over time show an increasing concentration of axitinib in the tissues thus demonstrating continued release of drug from the fiber depot over the 6 month period. Abbreviations as described above.

| Weeks | Choroid | Retina | VH | Depot | AH | Plasma |
| --- | --- | --- | --- | --- | --- | --- |
|  | ng/g |  |  |  |  |  |
| 4 | 591 | 356 | 513 | 290 | 0.064288 | <LLOQ |
| 12 | 3436 | 2293 | 1589 | 120.6 | <LLOQ | <LLOQ |
| 26 | 4690 | 5494 | 9907 | 110 | <LLOQ | <LLOQ |
|  | nM |  |  |  |  |  |
| 4 | 1529 | 921 | 1328 | 751 | 0 | <LLOQ |
| 12 | 8890 | 5933 | 4112 | 312 | <LLOQ | <LLOQ |
| 26 | 12135 | 14215 | 25632 | 284 | <LLOQ | <LLOQ |

| Weeks | Retina |
| --- | --- |
| $xIC_{50}$ | |
| 4 | 4605 |
| 12 | 29664 |
| 26 | 71076 |
| LOG $xIC_{50}$ | |
| 4 | 3.7 |
| 12 | 4.5 |
| 26 | 4.9 |
| LOG $xIC_{50}$ Standard Dev | |
| 4 | 0.381949 |
| 12 | 0.702367 |
| 26 | 0.570677 |

Many embodiments have been set forth herein. In general, components of the embodiments may be mixed-and-matched with each other as guided for the need to make functional embodiments. For instance, aspect ratios, gauge sizes, diameters, coil times, precursors, functional groups, hydrogel structures, degradation times, relative degradation times, swelling and elongation coefficients, therapeutic agents, agent loading processes, weakening techniques, necking techniques, bipolymer and multipolymer vehicle designs, sites of delivery, delivery methods, and other features set forth herein may be independently chosen as guided by this Application and the skill of the art to make and use the embodiments set forth herein. Patent application, patents, journal articles, and publications set forth herein are hereby incorporated by reference herein; in case of conflict, the instant specification controls.

Further Disclosure

1. A method of drug delivery comprising introducing a solid shape-changing vehicle containing a drug into a tissue, the vehicle changing shape in response to a physiological fluid of the tissue and providing a controlled release of a therapeutic agent.
2. The method of 1 wherein the vehicle also changes in volume in response to a physiological fluid of the tissue. The method of 1 wherein the vehicle has a first effective gauge that changes to a larger effective gauge after changing shape in response to the physiological fluid.
3. The method of 1 or 2 wherein the vehicle, in response to the physiological fluid, decreases in length, increases in width, and increases in volume.
4. The method of any of 1-3 wherein the vehicle is passed through an opening and placed at the tissue, with the change in shape and a volume change of the vehicle preventing expulsion of the vehicle through the opening.
5. The method of 4 wherein the opening is a puncture, a puncture made with a needle, an entry wound, or a pre-existing passage.
6. The method of any of 1-5 wherein a shape and/or a volume change of the vehicle reduces the tendency of the vehicle to migrate from the site where it is initially placed compared to the shape and dimensions of the vehicle before the shape change.
7. The method of any of 1-6 wherein the vehicle, before introduction into the tissue, is a rod having an aspect ratio of at least 1:10.
8. The method of 7 wherein the rod is straight prior to introduction into the tissue.
9. The method of any of 1-8 wherein the vehicle curls into a curved shape in response to the fluid.
10. The method of any of 1-5 wherein the vehicle is a rod that, in response to the fluid, coils.
11. The method of any of 1-6 wherein the vehicle, before the introduction, is passable through a hypodermic needle (for example, 27 gauge) of at least 5 mm in length.
12. The method of any of 1-11 wherein the vehicle is biodegradable.
13. The method of 12 wherein the vehicle is biodegradable as a result of the spontaneous hydrolysis of water-labile bonds upon exposure to the physiological fluid.
14. The method of 12 wherein the vehicle does not have water-labile bonds and is biodegradable in response to local cellular and/or enzymatic activity at the site of implantation.
15. The method of any of 1-14 wherein the vehicle is a xerogel that forms a hydrogel when exposed to the physiological fluid.
16. The method of any of 1-15 wherein the vehicle comprises a weakened area that provides for the vehicle to curve when exposed to the fluid.
17. The method of 16 wherein the weakened area comprises a notch that is a result of a stretching process or created with tools for cutting or removing material to make the weakened area(s).
18. The method of any of 1-17 wherein the vehicle comprises a first and a second material that are joined together.
19. The method of 14 wherein the first material has a first coefficient of elongation in physiological solution and the second material has a second coefficient of elongation in physiological solution, with first and second coefficients of elongation being different.
20. The method of 19 wherein the first material has a first coefficient of swelling in physiological solution and the second material has a second coefficient of swelling in physiological solution, with first and second coefficients of swelling being different.
21. The method of 19 or 20 wherein the vehicle comprises a layer of the second material on the first material.
22. The method of 19 or 20 wherein the vehicle comprises a layer of the second material that surrounds the first material.
23. The method of 22 wherein the first material comprises at least one rod or at least one strand, with the rod or the strand being surrounded by the first material.
24. The method of 23 wherein the at least one rod or the at least one stand have a coefficient of elongation that is not the same as the coefficient of elongation. As a result, shape changes upon exposure to physiological fluid are provided, including complex shape changes. A coefficient of elongation may be independently selected for each of the rods or strands.
25. The method of claim 24 wherein the at least one rod or the at least one strand surrounded by the second material have a rate of degradation that is not the same a rate of degradation of the second material. As a result, further shape changes may be provided during the degradation process.
26. The method of any of 18-25 wherein the first material is a rod encapsulated by the first material.
27. The method of any of 19-25 wherein the first coefficient (elongation or swelling) and the second coefficient (elongation or swelling) are independently selected to be less than one or more than one.
28. The method of any of 18-27 wherein the first material or the second material also encapsulates or otherwise holds a drug.
29. The method of any of 18-28 wherein the first material and/or the second material has a coefficient of elongation and/or a coefficient of swelling that ranges from 0.05 to 0.5.
30. The method of any of 18-28 wherein the first coefficient (elongation or swelling) and the second coefficient (elongation or swelling) are independently selected to be in a range from 0.01 to 100.
31. The method of any of 18-28 wherein the first material and the second material degrade at different rates, or one of the materials is non-degradable and the second material is degradable.
32. The method of 31 wherein the first material and the second material are chosen to degrade at a rate independently selected from 2 days to 5 years. Artisans will immediately appreciate that all ranges and values between the explicitly stated bounds are contemplated, with, e.g., any of the following being available as an upper or lower limit: 3, 4, 5, 6, 7 days, 1, 2, 3, 4, 5, 10, 15, 20, 25, 30, 35, 40, 45, 50, 52 weeks, 1, 1.5, 2, 2.5, 3, 3.5, 4, 4.5, 5 years.
33. The method of 31 wherein the first material degrades at a rate that is from 1.5× to 10× faster than the second material or vice versa.

34. The method of claim any of 31-33 wherein the differential degradation rates provide for the vehicle to maintain an initial shape (e.g., coil shape) for a period of time between 2-365 days (all ranges contemplated). This property provides for the shape to be maintained until advanced stages of the degradation process.
35. The method of any of 31-33 wherein the differential degradation rates determine the ability to unfurl a coil or other compact shape at particular stages of the degradation process.
36. The method of claim 33 wherein the first material comprises multiple hydrogels (e.g., rods, strands) surrounded by the second material
37. The method of claim 36 wherein the multiple strands surrounded by the second material have a range coefficients of elongation such that complex shape changes upon exposure to physiological fluid can be engineered.
38. The method of claim 36 wherein the multiple strands surrounded by the second material have a range of hydrolytic or enzymatic degradation times to control shape changes during the degradation process.
39. The method of any of 1-38 wherein the therapeutic agent has a solubility in aqueous solution of no more than 10 micrograms per milliliter.
40. The method of any of 1-38 wherein the therapeutic agent is a protein with MW greater than 1000 Da.
41. The method of any of 1-38 wherein the therapeutic agent is encapsulated in a microparticle.
42. The method of any of 1-41 wherein the therapeutic agent comprises an anti-angiogenic agent or other agent set forth herein.
43. The method of any of 1-41 wherein the therapeutic agent comprises a tyrosine kinase inhibitor.
44. The method of any of 1-41 wherein the therapeutic agent comprises an anti-VEGF protein or antibody or aptamer.
45. The method of any of 1-41 wherein the therapeutic agent comprises an anti-PDGF protein or antibody or aptamer.
46. The method of any of 1-41 wherein the therapeutic agent comprises an anti-Ang2 protein or antibody or aptamer.
47. The method of any of 1-46 wherein the tissue is a potential space that is natural or is created for deposition of the vehicle.
48. The method of any of 1-46 wherein the vehicle is introduced at, in, or near an eye, into the conjunctiva, on the cornea, on a sclera, inside a sclera, on an interior wall of the eye, intraocular, in the vitreous humor, on a retina, near a retina but not touching a retina, a distance of 1 to 2000 microns from a retina, suprachoroidal, in the choroidal, in a potential space, in a lumen artificially (by a user, with a tool) created to receive the vehicle, in a chamber of an eye, in the posterior chamber, in contact with vitreous humor, in the hyaline canal, or a combination thereof.
49. The method of any of 1-46 wherein the vehicle is introduced at, in, or near a vitreous humor or aqueous humor, Canaliculus, ampulla, Paranasal sinus, Joint capsules (e.g. knee, hip, etc.), Lumpectomy site, Biopsy site, Tumor core, Ear canal, Vaginal, Bladder, Esophageal, Bronchial, Abscesses, e.g. Dental, AV malformation sites, Vascular aneurysms or dissections, potential spaces, artificially created spaces or potential spaces, pessary, buccal, anal, urethral, nasal, breast, iatrogenic, cancer, organs, luminal spaces, natural lumen, vascular, aneurysm.
50. The method of any of claims 1-49 wherein the vehicle is a rod that has an end that is cut at an angle of 30-60 degrees relative to a perpendicular cross-section.
51. The method of 50 further comprising introducing a plurality of the vehicles through a single needle or catheter.
52. The method of 51 wherein the vehicles contact each other in the single needle or catheter and are released into the site where they independently change shape, e.g., coil or form helices.
53. A device for drug delivery comprising a therapeutic agent disposed in a vehicle that changes shape in response to a physiological fluid and provides a controlled release of a therapeutic agent.
54. The device of 53 wherein the vehicle comprises a rod with an aspect ratio of at least 1:10.
55. The device of 53 or 54 wherein the vehicle has a first effective gauge that changes to a larger effective gauge after changing shape in response to the physiological fluid.
56. The device of any of 50-55 wherein the vehicle in response to the physiological fluid, decreases in length and increases in width.
57. The device of any of 50-56 wherein the device, before introduction into the eye, is a rod having an aspect ratio of at least 1:10.
58. The device of any of 50-33 wherein the device curls into a curved shape response to the fluid.
59. The device of any of 50-34 wherein the vehicle is a rod that, in response to the fluid, coils.
60. The device of any of 50-35 wherein the vehicle, before the introduction, is passable through a 27 gauge thin wall needle of at least 5 mm in length.
61. The device of any of 50-36 wherein the vehicle is biodegradable.
62. The device of 61 wherein the vehicle is biodegradable as a result of the spontaneous hydrolysis of water-labile bonds upon exposure to the physiological fluid.
63. The device of 61 wherein the vehicle does not have water-labile bonds and is biodegradable in response to local cellular and/or enzymatic activity at the site of implantation.
64. The device of any of 50-63 wherein the vehicle is a xerogel that forms a hydrogel when exposed to the physiological fluid.
65. The device of any of 50-64 wherein the vehicle comprises a weakened area that provides for the vehicle to curve when exposed to the fluid.
66. The device of 65 wherein the weakened area comprises a score, a notch, or a tear, with any of the same being a result of a stretching process or created with tools for cutting or removing material to make the weakened area(s).
67. The device of any of 50-66 wherein the vehicle comprises a first and a second material that are joined together.
68. The device of 67 wherein the first material has a first coefficient of elongation in physiological solution and the second material has a second coefficient of elongation in physiological solution, with first and second coefficients of elongation being different.
69. The device of 67 wherein the first material has a first coefficient of swelling in physiological solution and the second material has a second coefficient of swelling in physiological solution, with first and second coefficients of swelling being different.

70. The device of 68 or 69 wherein the vehicle comprises a layer of the first material on the second material.
71. The device of 68 or 69 wherein the vehicle comprises a layer of the second material that surrounds the first material.
72. The device of 71 wherein the first material is a rod encapsulated by the first material.
73. The device of any of 68-72 wherein the first coefficient (elongation or swelling) and the second coefficient (elongation or swelling) are independently selected to be less than one or more than one.
74. The device of any of 68-72 wherein the first material and/or second material has a coefficient of change that ranges from 0.05 to 0.5.
75. The device of any of 68-72 wherein the first coefficient (elongation or swelling) and the second coefficient (elongation or swelling) are independently selected to be in a range from 0.01 to 100.
76. The device of any of 68-75 wherein the first material comprises multiple strands surrounded by the second material
77. The device of any of 68-75 wherein the multiple strands surrounded by the second material have a range coefficients of elongation such that complex shape changes upon exposure to physiological fluid can be engineered.
78. The device of any of 68-75 wherein the multiple strands surrounded by the second material have a range of hydrolytic or enzymatic degradation times to control shape changes during the degradation process.
79. The device of any of 50-75 wherein the therapeutic agent has a solubility in aqueous solution of no more than 10 micrograms per milliliter.
80. The method of any of 50-79 wherein the therapeutic agent is a protein with MW greater than 1000 Da
81. The method of any of 50-80 wherein the therapeutic agent is encapsulated in a microparticle.
82. The device of any of 50-79 wherein the therapeutic agent comprises an anti-angiogenic agent or other agent set forth herein.
83. The device of any of 50-82 wherein the therapeutic agent comprises a tyrosine kinase inhibitor.
84. The device of any of 50-53 wherein the therapeutic agent comprises a anti-VEGF protein or antibody or aptamer.
85. The device of any of 50-53 wherein the therapeutic agent comprises a anti-PDGF protein or antibody or aptamer.
86. The device of any of 50-53 wherein the therapeutic agent comprises a anti-Ang2 protein or antibody or aptamer.
87. A device or a use of a device of any of 50-86 wherein the vehicle is introduced at, in, or near an eye, into the conjunctiva, on the cornea, on a sclera, inside a sclera, on an interior wall of the eye, intraocular, intravitreal, on a retina, near a retina but not touching a retina, a distance of 1 to 2000 microns from a retina, suprachoroidal, in the choroidal, in a potential space, in a lumen artificially (by a user, with a tool) created to receive the vehicle, in a chamber of an eye, in the posterior chamber, in contact with vitreous humor, in the hyaline canal, or a combination thereof.
88. The device of any of 50-86 wherein the vehicle is introduced at, in, or near a vitreous humor or aqueous humor, Canaliculus, ampulla, Paranasal sinus, Joint capsules (e.g. knee, hip, etc.), Lumpectomy site, Biopsy site, Tumor core, Ear canal, Vaginal, Bladder, Esophageal, Bronchial, Abscesses, e.g. Dental, AV malformation sites, Vascular aneurysms or dissections, potential spaces, artificially created spaces or potential spaces, pessary, buccal, anal, uretheral, nasal, breast, iatrogenic, cancer, organs, luminal spaces, natural lumen, vascular, aneurysm.
89. A process of making a medical vehicle that changes shape upon exposure to aqueous solution comprising
    stretching a polymeric material and drying it in the stretched configuration,
    joining two materials together that have different coefficients of elongation, or
    joining two materials together that have different coefficients of coefficients of swelling.
90. The process of 89 comprising preparing the vehicle by stretching a material while wet and allowing the material to dry in the stretched position.
91. A process of making a solid medical vehicle that changes shape upon exposure to aqueous solution comprising
    crosslinking a first polymeric material
    stretching the first polymeric material to a stretched configuration and, while the material is maintained under tension or otherwise in the stretched configuration, making a layer of a second crosslinked material that contacts the stretched material,
    herein the first material is chosen to decrease in length after exposure to aqueous solution while it is in the stretched configuration.
92. The process of 91 further comprising forming the first polymeric material and drying the material before and/or during and/or after stretching the material.
93. The process of 91 or 92 further comprising, after forming the layer, drying the combined materials.
94. The process of any of 91-93 wherein the first material and the second material are independently chosen to be a hydrogel or an organogel.
95. The process of any of 91-94 wherein the material is stretched by a factor between 2 and 10.
96. The process of any of 91-95 wherein the stretching of the material comprises forming zones of weakness in the material that result in a coiling of the vehicle upon exposure to physiological solution.
97. A process of making a solid medical vehicle that changes shape upon exposure to aqueous solution comprising
    crosslinking a first polymeric material with a first swelling coefficient.
    crosslinking a layer of a second polymeric material that contacts the first material with the second polymeric material having a second swelling coefficient that is lower than the first swelling coefficient,
    wherein the first material changes in length to a lesser extent than the second material after exposure to aqueous solution.
98. The process of 97 wherein the first material increases in length after exposure to aqueous solution.
99. The process of 97 wherein the first material decreases in length after exposure to aqueous solution.
100. The process of any of 97-99 wherein the second material increases in length; alternatively, wherein the second material decreases in length.
101. The process of any of 97-100 wherein the layers are formed within a mold, e.g., a tubular mold, and the first polymeric material and the second polymeric material are introduced into the mold separately.

102. The process of any of 97-101 wherein the layers are formed within a mold, e.g. a tubular mold, and the first polymeric material and the second polymeric material are introduced into the mold simultaneously.

103. The process of 102, wherein the introduction is performed utilizing laminar flow to minimize mixing of the first polymeric material with the second polymeric material.

104. The process of any of 101-103 wherein the mold has a complex shape.

105. The process of any of 101-104 wherein, after at least partial crosslinking in the mold, or after crosslinking, the crosslinked vehicle is further shaped by stretching.

106. The process of 105 wherein the shaping is performed while the materials are a melt or while the materials are swollen in a solvent.

107. The process of 106 wherein the materials are cooled or dried to achieve a final shape, e.g., a fiber.

The invention claimed is:

1. A method of ocular delivery of a therapeutic agent to a patient comprising introducing a device for drug delivery to an ocular placement site, wherein the device comprises a therapeutic agent disposed in a solid vehicle that comprises a first xerogel and a second xerogel, wherein the first xerogel is a rod and the second xerogel is a layer on the first xerogel, wherein the first xerogel and the second xerogel differentially swell and/or elongate to change the rod into a curve shape in response to a physiological fluid of the ocular placement site, wherein the solid vehicle provides a controlled release of the therapeutic agent.

2. The method of claim 1 wherein the ocular placement site comprises in an eye, into a conjunctiva, on a cornea, on a sclera, inside a sclera, on an interior wall of an eye, intraocular, intravitreal, on a retina, near a retina but not touching a retina, suprachoroidal, in the choroid, in a lumen created to receive the solid vehicle, in a chamber of an eye, in the posterior chamber, in contact with vitreous humor, in the hyaline canal, in a vitreous humor, in an aqueous humor, or at a tissue.

3. The method of claim 1 wherein the rod comprises a fiber, a ribbon, a cylindrical rod, or a braided strand.

4. The method of claim 1 wherein the solid vehicle has an aspect ratio of at least 1:10.

5. The method of claim 1 wherein the curve shape comprises a coil, a spiral, or a helix.

6. The method of claim 5 with the solid vehicle forming the coil within 30 seconds of introducing.

7. The method of claim 1 wherein the first xerogel has a first coefficient of elongation and/or a first coefficient of swelling in aqueous solution and the second xerogel has a second coefficient of elongation and/or a second coefficient of swelling in aqueous solution, with the first and the second coefficients being different.

8. The method of claim 1 wherein the first xerogel has a first coefficient of elongation in aqueous solution and the second xerogel has a second coefficient of elongation in aqueous solution, wherein the first coefficient of elongation is less than 1 and the second coefficient of elongation is at least 1.

9. The method of claim 7 wherein the first coefficient of elongation is from 0.1 to 0.5 and the second coefficient of elongation is from 1 to 10.

10. The method of claim 7 wherein the first coefficient of swelling is from 1.0 to 2.0 and the second coefficient of swelling is from 2.0 to 10.

11. The method of claim 1 wherein the solid vehicle is biodegradable.

12. The method of claim 1 wherein the first xerogel and the second xerogel at the ocular placement site degrade at a rate independently selected from 2 days to 5 years.

13. The method of claim 1 wherein the first xerogel comprises at least a first crosslinked polymer and the second xerogel comprises at least a second crosslinked polymer.

14. The method of claim 1 wherein the first xerogel and the second xerogel are independently selected from the group consisting of natural, synthetic, and biosynthetic polymers.

15. The method of claim 1 wherein the first xerogel and the second xerogel are joined by covalent bonds.

16. The method of claim 1 wherein introducing comprises deploying the solid vehicle from an applicator.

17. The method of claim 1 wherein the therapeutic agent has a solubility in aqueous solution of no more than 10 micrograms per milliliter, is a protein with MW greater than 1000 Da, or is encapsulated in a microparticle.

18. The method of claim 1 wherein the therapeutic agent comprises an anti-angiogenic agent, a tyrosine kinase inhibitor, an anti-VEGF agent, an anti-PDGF agent, an anti-Ang2 agent, a steroid, an NSAID, an anti-cancer drug, an antibody, an antibody fragment, a steroid, a corticosteroid, a PDGF inhibitor, a visualization agent, or combinations thereof.

19. The method of claim 1 wherein the therapeutic agent comprises one or more of trimacinalone, trimacinalone acetonide, dexamethasone, dexamethasone acetate, fluocinolone, fluocinolone acetate, loteprednol etabonate, or analogues thereof.

20. The method of claim 1 wherein the therapeutic agent is for treatment of an eye disease or an eye condition.

* * * * *

UNITED STATES PATENT AND TRADEMARK OFFICE
CERTIFICATE OF CORRECTION

PATENT NO. : 11,938,223 B2
APPLICATION NO. : 17/859820
DATED : March 26, 2024
INVENTOR(S) : Jarrett et al.

It is certified that error appears in the above-identified patent and that said Letters Patent is hereby corrected as shown below:

In the Claims

In Column 62, Claim 19, Line 44, delete "trimacinalone, trimacinalone" and insert -- triamcinolone, triamcinolone --, therefor.

Signed and Sealed this
Twelfth Day of November, 2024

Katherine Kelly Vidal
*Director of the United States Patent and Trademark Office*